(12) United States Patent
Angibaud et al.

(10) Patent No.: US 8,404,713 B2
(45) Date of Patent: Mar. 26, 2013

(54) QUINOLINONE DERIVATIVES AS PARP INHIBITORS

(75) Inventors: Patrick René Angibaud, Fontaine-Bellenger (FR); Laurence Françoise Bernadette Marconnet-Decrane, Tassin-la-Demi Lune (FR); Jorge Eduardo Vialard, Brussels (BE); Laurence Anne Mevellec, Louviers (FR); Christophe Meyer, Les Authieux sur le Port Saint Ouen (FR); Pierre-Henri Storck, Ramsgate (GB)

(73) Assignee: Janssen Pharmaceutica NV, Beerse (BE)

( * ) Notice: Subject to any disclaimer, the term of this patent is extended or adjusted under 35 U.S.C. 154(b) by 347 days.

(21) Appl. No.: 12/681,790

(22) PCT Filed: Oct. 22, 2008

(86) PCT No.: PCT/EP2008/064243
§ 371 (c)(1),
(2), (4) Date: Apr. 6, 2010

(87) PCT Pub. No.: WO2009/053373
PCT Pub. Date: Apr. 30, 2009

(65) Prior Publication Data
US 2010/0222348 A1   Sep. 2, 2010

(30) Foreign Application Priority Data
Oct. 26, 2007   (EP) ..................................... 07119417

(51) Int. Cl.
A61K 31/04 (2006.01)
C07D 215/38 (2006.01)
(52) U.S. Cl. ........................................ 514/312; 546/159
(58) Field of Classification Search .................. 546/159; 514/312
See application file for complete search history.

(56) References Cited

U.S. PATENT DOCUMENTS

| | | | |
|---|---|---|---|
| 3,274,194 A | 9/1966 | Hayao et al. | |
| 3,753,988 A | 8/1973 | Rodway et al. | |
| 3,919,425 A | 11/1975 | Vidrio | |
| 4,335,127 A | 6/1982 | Vandenberk et al. | |
| 5,028,606 A | 7/1991 | Venet et al. | |
| 5,118,684 A | 6/1992 | Sugimoto et al. | |
| 5,151,421 A | 9/1992 | Venet et al. | |
| 5,177,075 A | 1/1993 | Suto et al. | |
| 5,231,184 A | 7/1993 | Stokbroekx et al. | |
| 5,304,560 A | 4/1994 | Shimazaki et al. | |
| 5,374,637 A | 12/1994 | Van Daele et al. | |
| 6,583,144 B2 | 6/2003 | Ohkura et al. | |
| 6,635,642 B1 | 10/2003 | Jackson et al. | |
| 7,115,630 B2 | 10/2006 | Mabire et al. | |
| 7,928,104 B2 * | 4/2011 | Mabire et al. | 514/249 |

| | | |
|---|---|---|
| 2002/0002174 A1 | 1/2002 | Nieduzak et al. |
| 2003/0130505 A1 | 7/2003 | Zhi et al. |
| 2003/0225268 A1 | 12/2003 | Bunnelle et al. |
| 2004/0077667 A1 | 4/2004 | Matsuoka et al. |
| 2004/0176361 A1 | 9/2004 | Fujio et al. |
| 2008/0039480 A1 | 2/2008 | Kennis et al. |
| 2008/0269234 A1 | 10/2008 | Gandhi et al. |
| 2009/0048259 A1 | 2/2009 | Austin et al. |
| 2009/0292121 A1 | 11/2009 | Morioka et al. |

FOREIGN PATENT DOCUMENTS

| | | |
|---|---|---|
| DE | 1006423 | 4/1957 |
| DE | 2258561 A | 6/1973 |
| EP | 0013612 B1 | 11/1983 |
| EP | 156433 | 10/1985 |
| EP | 391462 A1 | 10/1990 |
| EP | 0638567 | 2/1995 |
| EP | 0371564 B1 | 7/1995 |
| EP | 0669919 B1 | 9/1995 |
| EP | 1026160 A1 | 8/2000 |
| EP | 0885190 B1 | 5/2003 |
| EP | 1355888 | 10/2008 |
| FR | 2436781 | 5/1980 |
| GB | 732581 A | 6/1955 |
| GB | 1062357 | 3/1967 |
| JP | 59-076082 | 4/1984 |
| JP | 60-120872 | 6/1985 |
| JP | 60-226862 | 11/1985 |
| JP | 62-234065 | 10/1987 |
| JP | 10007572 | 1/1998 |
| JP | 10-330377 | 12/1998 |
| JP | 2002-515072 | 3/1999 |
| JP | 2000-505100 | 4/2000 |
| JP | 2000191659 | 7/2000 |
| JP | 2002-535409 | 8/2000 |
| JP | 2002284699 | 10/2002 |

(Continued)

OTHER PUBLICATIONS

Amé, J-C., et al. "The PARP Superfamily", BioEssays vol. 26 pp. 882-893 (2004).

(Continued)

*Primary Examiner* — D M Seaman

(57) ABSTRACT

Compounds of formula (I):

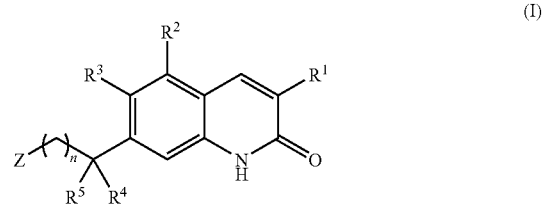

wherein $R^1$, $R^2$, $R^3$, $R^4$, $R^5$, Z and n have defined meanings, the N-oxide forms, the pharmaceutically acceptable addition salts, the quaternary ammonium salts and the stereochemically isomeric forms thereof, and their use for the treatment of PARP-mediated disorders.

14 Claims, No Drawings

FOREIGN PATENT DOCUMENTS

| | | |
|---|---|---|
| WO | WO 91/12006 A2 | 8/1991 |
| WO | WO 9322309 A1 | 11/1993 |
| WO | WO 94/19342 A1 | 9/1994 |
| WO | WO 95/24379 A1 | 9/1995 |
| WO | WO 98/11128 A1 | 3/1998 |
| WO | WO 99/11649 A2 | 3/1999 |
| WO | WO 99/29687 A1 | 6/1999 |
| WO | WO 00/44755 A1 | 8/2000 |
| WO | WO 02/28837 A1 | 4/2002 |
| WO | WO 02/36599 A1 | 5/2002 |
| WO | WO 02/48117 A1 | 6/2002 |
| WO | WO 03/015785 A1 | 2/2003 |
| WO | WO 03/039460 A2 | 5/2003 |
| WO | WO 03/055865 A1 | 7/2003 |
| WO | WO 03/080581 A1 | 10/2003 |
| WO | WO 03/082350 A2 | 10/2003 |
| WO | WO 03/101985 A1 | 12/2003 |
| WO | WO 2005/004801 A2 | 1/2005 |
| WO | 2005/054209 * | 6/2005 |
| WO | WO 2005/054199 A1 | 6/2005 |
| WO | WO 2005/054201 A1 | 6/2005 |
| WO | WO 2005/054209 A1 | 6/2005 |
| WO | WO 2005/054210 A1 | 6/2005 |
| WO | WO 2005/058843 A1 | 6/2005 |
| WO | WO 2005/097750 A1 | 10/2005 |
| WO | WO 2005/117876 A1 | 12/2005 |
| WO | WO 2006/003146 A1 | 1/2006 |
| WO | WO 2006/003147 A1 | 1/2006 |
| WO | WO 2006/003148 A1 | 1/2006 |
| WO | WO 2006/003150 A1 | 1/2006 |
| WO | WO 2006/089177 A2 | 8/2006 |
| WO | WO 2007/025009 A2 | 3/2007 |
| WO | WO 2007/087684 A1 | 8/2007 |
| WO | WO 2007/095628 A1 | 8/2007 |
| WO | WO 2008/107478 A1 | 9/2008 |
| ZA | 72/8536 A | 11/1972 |

OTHER PUBLICATIONS

Horvath, E., et al. Poly(ADP-Ribose) Polymerase as a Drug Target for Cardiovascular Disease and Cancer: An Update, Drug News Perspective, vol. 20 (3), p. 171 (2007).

Li, J-H., et al. "PARP Inhibitors", IDrugs, vol. 4(7), pp. 804-812 (2001).

Nguewa, P., et al. "Poly(ADP-Ribose) Polymerases: Homology, Structural Domains and Functions. Novel Therapeutical Applications", Biophysics & Molecular Biology, vol. 88 pp. 143-172 (2005).

Tentori, L., et al. "Poly(ADP-Ribose) Polymerase (PARP) Inhibition or PARP-1 Gene Deletion Reduces Angiogenesis", European Journal of Cancer, vol. 43, pp. 2124-2133 (2007).

Weltin, D., et al. "Effect of 6(5H)-Phenanthridinone, an Inhibitor of Poly(ADP-Ribose) Polymerase, on Cultured Tumor Cells", Oncology Research, vol. 6, No. 9, pp. 399-403 (1994).

International Search Report PCT/EP2008/064243, mailed Mar. 30, 2009.

Albert, J.M., et al., "Inhibition of Poly(ADP-Ribose) Polyerase Enhances Cell Death and Improves Tumor Growth Delay in Irradiated Lung Cancer MODels", Clin Cancer Res, (2007), vol. 13, No. 10, pp. 3033-3042.

Ali, M.M., et al., "Synthesis and Antimicrobial Activities of Some Novel Quinoxalinone Derivatives", Molecules, (2000), vol. 5, No. 6, pp. 864-873.

Ame, J.C., et al., "PARP-2, a Novel Mammalian DNA Damage-Dependent Poly(ADP-Ribose) Polymerase", Journal of Biological Chemistry, (1999), vol. 274, No. 25, pp. 17860-17868.

Ame, J.C., et al., "The PARP Superfamily", BioEssays, (2004), vol. 26, No. 8, pp. 882-893.

Bellasio, E., et al., "Antihypertensives. N-1$H$-Pyrrol-1-YL-3-Pyridazinamines", J. Med. Chem., (1984), vol. 27, No. 8 pp. 1077-1083.

Blackburn, W., et al., "The Preparation of 3-Methyl-6- and -7-Carboxy-2-Quinoxalones", Journal of Organic Chemistry, ((1961), vol. 26, pp. 2805-2809.

Bloch, W., et al., "Poly-Adenosine Diphosphate-Ribose Polymerase Inhibition for Myocardial Protection: Pathophysiologic and Physiologic Considerations", Journal of Thoracic and Cardiovascular Surgery, vol. 128, No. 2, pp. 323-324.

Bonne, D., et al., "4',6-Diamidino-2-Phenylindole, A Fluorescent Probe for Tubulin and Microtubules", Journal f Biological Chemistry, (1985), vol. 260, No. 5, pp. 2819-2825.

Calabrese, C.R., et al., "Anticancer Chemosensitization and Radiosensitization by the Novel Poly(ADP-Ribose) Polymerase-1 Inhibitor AG14361", Journal of the National Cancer Institute, (2004), vol. 96, No. 1, pp. 56-67.

Cardozo, M.G., et al., "Conformational Analyses and Molecular-Shape Comparisons of a Series of Indanone-Benzylpiperidine Inhibitors of Acetylcholinesterase", J. Med. Chem., (1992), vol. 35, pp. 590-601.

Cockcroft, X., et al., "Phthalazines 2: Optimisation and Synthesis of Novel Potent Inhibitors of Poly(ADP-Ribose)Polymerase", Bioorganic & Medicinal Chemistry Letters, (2006), vol. 16, pp. 1040-1044.

Costantino, G., et al., "Modeling of Poly(ADP-Ribose)Polymerase (PARP) Inhibitors. Docking of Ligands and Quantitative Structure-Activity Relationship Analysis", J. Med. Chem., (2001), vol. 44, pp. 3786-3794.

Cuzzocrea, S., "Shock Inflammation and PARP", Pharmacological Research, (2005), vol. 52, pp. 72-82.

Dastmalchi, S., et al., "Molecular Modelling of Human Aldehyde Oxidase and Identification of the Key Interactions in the Enzyme-Substrate Complex", Daru, J. Faculty of Pharm., (2005), vol. 13, No. 3, pp. 82-93.

Dörwald, F.Z., "Side Reactions in Organic Synthesis": A Guide to Successful Synthesis Design, Weinheim: Wiley-VCH Verlag GmbH & Co. KGaA, (2005), Preface.

Golbraikh, A., et al., "Validation of Protein-Based Alignment in 3D Quantitative Structure-Activity Relationships With CoMFA Models", Eur. J. Med. Chem., (2000), vol. 35, pp. 123-136.

Guery, S., et al., "Synthesis of 4-Aryl-1-(4-Methylpiperazin-1-YL)Phthalazines by Suzuki-Type Cross-Coupling Reaction", Synthesis, (2001), No. 5, pp. 699-701.

Gupta, C.M., et al., "Drugs Acting on the Central Nervous System. Syntheses of Substituted Quinazolones and Quinazolines and Triazepino- and Triazocinoquinazolones", Journal of Medicinal Chemistry (1968), vol. 11, No. 2, pp. 392-395.

Habon, T., et al., "The Effect of Carvedilol on Enhanced ADP-Ribosylation and Red Blood Cell Membrane Damage Caused by Free Radicals", Cardiovascular Research, (2001), vol. 52, p. 153-160.

Hayao, S., et al., "New Sedative and Hypotensive 3-Substituted 2,4(1H,3h-)-Quinazolinediones", Journal of Medicinal Chemistry, (1965), vol. 8, pp. 807-811.

Hazard, P.R., et al., "De Quelques Actions Pharmacologiques Exercees Par Des Derives De L'Orthoprocainamide", Thérapie, (1965), vol. XX, pp. 1043-1049.

Herndon, J.L., et al., "Ketanserin Analogues: Structure-Affinity Relationships for 5-HT$_2$ and 5-HT$_{1c}$ Serotonin Receptor Binding", J. Med. Chem., (1992), vol. 35, pp. 4903-4910.

Hori, M., et al., "Novel 4-Phenoxy-2-(1-Piperazinyl)Quinazolines as Potent Anticonvulsive and Antihypoxic Agents", Chem. Pharm. Bull, (1990), vol. 38, No. 3, pp. 681-687.

Hori, M., et al., "Novel 4-Phenoxy-2-(1-Piperazinyl)Quinazolines as Potent Anticonvulsive and Antihypoxic Agents", Chem. Pharm. Bull, (1990), vol. 38, No. 5, pp. 1286-1291.

Horvath, E.M., et al., "Poly(ADP-Ribose) Polymerase as a Drug Target for Cardiovascular Disease and Cancer: An Update", Drug News Perspect, (2007), vol. 20, No. 3, pp. 171-181.

Jordan, V.C., "Tamoxifen: A Most Unlikely Pioneering Medicine", Nature Reviews, (2003), vol. 2, pp. 205-213.

Katoh, A., et al., "Synthesis of Quinoxaline Derivatives Bearing the Styryl and Phenylethynyl Groups and Application to a Fluorescence Derivatization Reagent", Heterocycles, (2000), vol. 52, No. 2, pp. 911-920.

Kormendy, K., et al., "Aminophthalazinone Derivatives, V Synthesis of 4-Hydrazino-1-(2-H)0phthalazinones, I", Acta Chimica Academiae Scientiarum Hungaricae, (1979), vol. 102, No. 1, pp. 39-50.

Kornet, M.J., et al., "Synthesis of 3-Amino-2,4(1$H$,3$H$)-Quinazolinediones for Testing as Anticonvulsants", J. Heterocyclic Chem., (1984), vol. 21, No. 5, pp. 1533-1535.

Kulcsar, G., et al., Synthesis and Study of New 4-Quinazolinone Inhibitors of the DNA Repair Enzyme Poly(ADP-Ribose) Polymerase (PARP), Arkivoc, XX,XX, (2003), vol. 2003, No. Part V, pp. 121-131.

Larner, A.J., "Poly(ADP-Ribose) Polymerase Inhibitors in the Prevention of Neuronal Cell Death", Expert Opin. Ther. Patents, (2002), vol. 12, No. 4, pp. 481-487.

Li, J.H., et al., "PARP Inhibitors", IDrugs, (2001), vol. 4, No. 7, pp. 804-812.

Lord, C.J., et al., "Targeted Therapy for Cancer Using PARP Inhibitors", Current Opinion in Pharmacology, (2008), vol. 8, pp. 363-369.

Meier, H.L., et al., "Alterations in Human Lymphocyte DNA Caused by Sulfur Mustard Can Be Mitigated by Selective Inhibitors of Poly(ADP-Ribose) Polymerase", Biochimica et Biophysica Acta, (1998), vol. 1404, pp. 367-376.

Miller, B.A., "Inhibition of TRPM2 Function by PARP Inhibitors Protects Cells From Oxidative Stress-Induced Death", British Journal of Pharmacology, (2004), vol. 143, pp. 515-516.

Nguewa, P.A., et al., "Poly(ADP-Ribose) Polymerases: Homology, Structural Domains and Functions. Novel Therapeutical Applications", Progress in Biophysics & Molecular Biology, (2005), vol. 88, pp. 143-172.

Oliver, A.W., et al., "Crystal Structure of the Catalytic Fragment of Murine Poly(ADP-Ribose) Polymerase-2", Nucleic Acids Research, (2004), vol. 32, No. 4, pp. 456-464.

Schreiber, V., et al., "Poly(ADP-Ribose) Polymerase-2 Is Required for Efficient Base Excision DNA Repair in Association With PARP-1 and XRCC1", Journal of Biological Chemistry, (2002), vol. 277, No. 25, pp. 23028-23036.

Szabo, G., et al., "Poly(ADP-Ribose Polymerase Inhibition Protects Against Myocardial and Endothelial Reperfusion Injury After Hypothermic Cardiac Arrest", Journal of Thoracic and Cardiovascular Surgery, (2003), vol. 126, No. 3, pp. 651-658.

Takai, H., et al., "Synthesis of Piperidine Derivatives With a Quinazoline Ring System As Potential Antihypertensive Agents", Chem. Pharm. Bull, (1986), vol. 34, No. 5, pp. 1907-1916.

Tasatargil, A., et al., "Poly(ADP-Ribose) Polymerase Inhibition Prevents Homocysteine-Induced Endothelial Dysfunction in the Isolated Rat Aorta", Pharmacology, (2004), vol. 72, pp. 99-105.

Tentori, L., et al., "Chemopotentiation by PARP Inhibitors in Cancer Therapy", Pharmacological Research, (2005), vol. 52, pp. 25-33.

Vippagunta, S.R., et al., "Crystalline Solids", Advanced Drug Delivery Reviews, (2001), vol. 48, pp. 3-26.

Virag, L., et al., "The Therapeutic Potential of Poly(ADP-Ribose) Polymerase Inhibitors", Pharmacological Reviews, (2002), vol. 54, No. 3, pp. 375-429.

Weltin, D., et al., "Effect of 6(5H)-Phenanthridinone, an Inhibitor of Poly(ADP-Ribose) Polymerase, on Cultured Tumor Cells", Oncology Research, (1994), vol. 6, No. 9, pp. 399-403.

Wolff, M.E., Burger's Medicinal Chemistry, 4$^{th}$ ed., Part I The Basis of Medicinal Chemistry, (1980), pp. 336-337.

Yolles, S., et al., "Quinoxaline Studies. I. The Preparation of 2-Hydroxy-3-Methyl-6-Methoxyquinoxaline and 2-Hydroxy-3-Methyl-7-Methoxyquinoxaline", Journal of the American Chemical Society, (1949), vol. 71, pp. 2375-2377.

Zhang, J., "PARP Inhibition: A Novel Approach to Treat Ischaemia/Reperfusion and Inflammation-Related Injuries", Emerging Drugs, (1999), vol. 4, pp. 209-221.

"Cancer definition", http://www.medterms.com/script/main/art.asp?articlekey=2580, accessed Nov. 27, 2007.

The Merck Index, 13$^{the}$ Ed., p. 670, monograph for "Ethyl Alcohol"©2001 by Merck and Co., Inc.

"Prostate Cancer Prevention", http://www.cancer.gov/cancertopics/pdg/prevention/prostate/Patient, accessed Apr. 9, 2010.

EDAN30610, Jun. 8, 2011.

Database CA 'Online! Chemical Abstracts Service, Columbus, Ohio, US; 2002, Tatsuno, Toru et al: "PARP Inhibitors for Treatment of Retinal Degeneration or Chemotherapy-Induced Cell Injury" XP002348719 retrieved from STN Database accession No. 2002:747681, relevant to claim 1-12.

Patent Abstracts of Japan, vol. 1998, No. 5, Apr. 30, 1998-& JP 10007572 A (Sumitomo Pharmaceut Co Ltd), Jan. 13, 1998 '0046!, Formula 14 abstract.

Database WPI 'Online! Derwent Publications Ltd., London, GB; XP002347462, retrieved from WPI accession No. 1970-18449R, *;see RN 27631-66-9:3-(piperidin-1-yl-propyl)-1H-quinazoline-2,4-dione*, abstract & JP 45007058B (Sankyo) Jul. 6, 1967.

Finney, D. J., "Graded Response: The Linear Dosage-Response Curve", Probit Analysis, 2nd Edition, Chapter 10 (1962), Cambridge Publishing Press, 16 page article.

International Search report for Application No. PCT/EP2004/013162 mailed Mar. 18, 2005.

International Search report for Application No. PCT/EP2004/013163 mailed Apr. 20, 2005.

International Search report for Application No. PCT/EP2004/013164 mailed Mar. 14, 2005.

International Search report for Application No. PCT/EP2004/013165 mailed Mar. 24, 2005.

International Search report for Application No. PCT/EP2005/053029 mailed Oct. 7, 2005.

International Search report for Application No. PCT/EP2005/053030 mailed Oct. 24, 2005.

International Search report for Application No. PCT/EP2005/053031 mailed Oct. 25, 2005.

International Search report for Application No. PCT/EP2008/052764 mailed Aug. 12, 2008.

International Search report for Application No. PCT/EP2008/064243 mailed Mar. 30, 2009.

International Search report for Application No. PCT/EP2009/053598 mailed May 19, 2009.

International Search report for Application No. PCT/EP2009/053604 mailed May 8, 2009.

* cited by examiner

QUINOLINONE DERIVATIVES AS PARP INHIBITORS

CROSS REFERENCE TO RELATED APPLICATIONS

This application is a national stage of PCT Application No. PCT/EP2008/064243, filed Oct. 22, 2008, which claims priority for EPO Patent Application No. 07119417.9, filed Oct. 26, 2007, all of which are hereby incorporated by reference in their entirety.

FIELD OF THE INVENTION

The present invention relates to inhibitors of PARP and provides compounds and compositions containing the disclosed compounds. Moreover, the present invention provides methods of using the disclosed PARP inhibitors for instance as a medicine.

BACKGROUND OF THE INVENTION

The nuclear enzyme poly(ADP-ribose) polymerase-1 (PARP-1) is a member of the PARP enzyme family. This growing family of enzymes consist of PARPs such as, for example: PARP-1, PARP-2, PARP-3 and Vault-PARP; and Tankyrases (TANKs), such as, for example: TANK-1 and TANK-2. PARP is also referred to as poly(adenosine 5'-diphospho-ribose) polymerase or PARS (poly(ADP-ribose) synthetase).

PARP-1 is a major nuclear protein of 116 kDa consisting of three domains: an N-terminal DNA binding domain containing two zinc fingers, an automodification domain and a C-terminal catalytic domain. The enzyme synthesizes poly(ADP-ribose), a branched polymer that can consist of over 200 ADP-ribose units. The protein acceptors of poly(ADP-ribose) are directly or indirectly involved in maintaining DNA integrity. They include histones, HMG proteins, topoisomerases, DNA and RNA polymerases, DNA ligases, $Ca^{2+}$- and $Mg^{2+}$-dependent endonucleases and single-strand break-repair and base-excision repair factors. PARP protein is expressed at a high level in many tissues, most notably in the immune system, heart, brain and germ-line cells. Under normal physiological conditions, there is minimal PARP activity. However, DNA damage causes an immediate activation of PARP by up to 500-fold. The resulting poly(ADP-ribose) production has three consequences: first, DNA-damage-induced poly(ADP-ribosyl)ation of the N- and C-terminal tails of histone H1 and H2B or the selective interaction of these proteins with free or PARP-1 bound poly(ADP-ribose) contributes to the relaxation of the 30-nm chromatin fibre and increases the access to breaks; second, it signals the occurrence and the extent of DNA damage so that the cell can establish an adaptive response according to the severity of the injury (DNA repair or cell suicide); third, it mediates the fast recruitment of single-strand break-repair and base-excision repair factors.

Single strand breaks (SSBs) occur spontaneously in all cells. In the absence of PARP-1 activity these SSBs may be converted to double strand breaks (DSBs) during replication that can lead to collapse of the replication forks. DSBs are identified by their epigenetic mark, the phosphorylation of the core histone variant H2AX (γH2AX). The very rapid local decondensation of chromatin, which occurs in a γ H2AX-independent manner at DSB's can be attributed to poly(ADP-ribose) production that is mediated locally by PARP-1.

Also developmental or environmental cues, such as steroids or heat shock, induce PARP-1 activation and the poly (ADP-ribose)-dependent stripping of histones from chromatin, thereby favouring the opening of the chromatin structure, which may allow transcriptional activation in the absence of DNA breaks.

Extensive PARP activation in cells suffering from massive DNA damage leads to severe depletion of $NAD^+$. The short half-life of poly(ADP-ribose) results in a rapid turnover rate. Once poly(ADP-ribose) is formed, it is quickly degraded by the constitutively active poly(ADP-ribose) glycohydrolase (PARG), together with phosphodiesterase and (ADP-ribose) protein lyase. PARP and PARG form a cycle that converts a large amount of $NAD^+$ to ADP-ribose. In less than an hour, over-stimulation of PARP can cause a drop of $NAD^+$ and ATP to less than 20% of the normal level. Such a scenario is especially detrimental during ischaemia when deprivation of oxygen has already drastically compromised cellular energy output. Subsequent free radical production during reperfusion is assumed to be a major cause of tissue damage. Part of the ATP drop, which is typical in many organs during ischaemia and reperfusion, could be linked to $NAD^+$ depletion due to poly(ADP-ribose) turnover. Thus, PARP or PARG inhibition is expected to preserve the cellular energy level thereby potentiating the survival of ischaemic tissues after insult.

Poly(ADP-ribose) synthesis is also involved in the induced expression of a number of genes essential for inflammatory response. PARP inhibitors suppress production of inducible nitric oxide synthase (iNOS) in macrophages, P-type selectin and intercellular adhesion molecule-1 (ICAM-1) in endothelial cells. Such activity underlies the strong anti-inflammation effects exhibited by PARP inhibitors. PARP inhibition is able to reduce necrosis by preventing translocation and infiltration of neutrophils to the injured tissues.

PARP is activated by damaged DNA fragments and, once activated, catalyzes the attachment of up to 100 ADP-ribose units to a variety of nuclear proteins, including histones and PARP itself. During major cellular stresses the extensive activation of PARP can rapidly lead to cell damage or death through depletion of energy stores. As four molecules of ATP are consumed for every molecule of $NAD^+$ regenerated, $NAD^+$ is depleted by massive PARP activation, in the efforts to re-synthesize $NAD^+$, ATP may also become depleted.

It has been reported that PARP activation plays a key role in both NMDA- and NO-induced neurotoxicity. This has been demonstrated in cortical cultures and in hippocampal slices wherein prevention of toxicity is directly correlated to PARP inhibition potency. The potential role of PARP inhibitors in treating neurodegenerative diseases and head trauma has thus been recognized even if the exact mechanism of action has not yet been elucidated.

Similarly, it has been demonstrated that single injections of PARP inhibitors have reduced the infarct size caused by ischemia and reperfusion of the heart or skeletal muscle in rabbits. In these studies, a single injection of 3-amino-benzamide (10 mg/kg), either one minute before occlusion or one minute before reperfusion, caused similar reductions in infarct size in the heart (32-42%) while 1,5-dihydroxyisoquinoline (1 mg/kg), another PARP inhibitor, reduced infarct size by a comparable degree (38-48%) These results make it reasonable to assume that PARP inhibitors could salvage previously ischaemic heart or reperfusion injury of skeletal muscle tissue.

PARP activation can also be used as a measure of damage following neurotoxic insults resulting from exposure to any of the following inducers like glutamate (via NMDA receptor stimulation), reactive oxygen intermediates, amyloid β-protein, N-methyl-4-phenyl-1,2,3,6-tetrahydropyridine (MPTP) or its active metabolite N-methyl-4 phenylpyridine ($MPP^+$), which participate in pathological conditions such as stroke, Alzheimer's disease and Parkinson's disease. Other studies have continued to explore the role of PARP activation in cerebellar granule cells in vitro and in MPTP neurotoxicity. Excessive neural exposure to glutamate, which serves as the predominate central nervous system neurotransmitter and acts upon the N-methyl D-aspartate (NMDA) receptors and other subtype receptors, most often occurs as a result of stroke or other neurodegenerative processes. Oxygen deprived neurons release glutamate in great quantities during ischaemic brain insult such as during a stroke or heart attack. This excess release of glutamate in turn causes over-stimulation (excitotoxicity) of N-methyl-D-aspartate (NMDA), AMPA, Kainate and MGR receptors, which open ion channels and permit uncontrolled ion flow (e.g., $Ca^{2+}$ and $Na^+$ into the cells and $K^+$ out of the cells) leading to overstimulation of the neurons. The over-stimulated neurons secrete more glutamate, creating a feedback loop or domino effect which ultimately results in cell damage or death via the production of proteases, lipases and free radicals. Excessive activation of glutamate receptors has been implicated in various neurological diseases and conditions including epilepsy, stroke, Alzheimer's disease, Parkinson's disease, Amyotrophic Lateral Sclerosis (ALS), Huntington's disease, schizophrenia, chronic pain, ischemia and neuronal loss following hypoxia, hypoglycemia, ischemia, trauma, and nervous insult. Glutamate exposure and stimulation has also been implicated as a basis for compulsive disorders, particularly drug dependence. Evidence includes findings in many animal species, as well as in cerebral cortical cultures treated with glutamate or NMDA, that glutamate receptor antagonists (i.e., compounds which block glutamate from binding to or activating its receptor) block neural damage following vascular stroke. Attempts to prevent excitotoxicity by blocking NMDA, AMPA, Kainate and MGR receptors have proven difficult because each receptor has multiple sites to which glutamate may bind and hence finding an effective mix of antagonists or universal antagonist to prevent binding of glutamate to all of the receptor and allow testing of this theory, has been difficult. Moreover, many of the compositions that are effective in blocking the receptors are also toxic to animals. As such, there is presently no known effective treatment for glutamate abnormalities.

The stimulation of NMDA receptors by glutamate, for example, activates the enzyme neuronal nitric oxide synthase (nNOS), leading to the formation of nitric oxide (NO), which also mediates neurotoxicity. NMDA neurotoxicity may be prevented by treatment with nitric oxide synthase (NOS) inhibitors or through targeted genetic disruption of nNOS in vitro.

Another use for PARP inhibitors is the treatment of peripheral nerve injuries, and the resultant pathological pain syndrome known as neuropathic pain, such as that induced by chronic constriction injury (CCI) of the common sciatic nerve and in which transsynaptic alteration of spinal cord dorsal horn characterized by hyperchromatosis of cytoplasm and nucleoplasm (so-called "dark" neurons) occurs.

Evidence also exists that PARP inhibitors are useful for treating inflammatory bowel disorders, such as colitis. Specifically, colitis was induced in rats by intraluminal administration of the hapten trinitrobenzene sulfonic acid in 50% ethanol. Treated rats received 3-aminobenzamide, a specific inhibitor of PARP activity. Inhibition of PARP activity reduced the inflammatory response and restored the morphology and the energetic status of the distal colon.

Further evidence suggests that PARP inhibitors are useful for treating arthritis. Further, PARP inhibitors appear to be useful for treating diabetes. PARP inhibitors have been shown to be useful for treating endotoxic shock or septic shock.

PARP inhibitors have also been used to extend the lifespan and proliferative capacity of cells including treatment of diseases such as skin aging, Alzheimer's disease, atherosclerosis, osteoarthritis, osteoporosis, muscular dystrophy, degenerative diseases of skeletal muscle involving replicative senescence, age-related muscular degeneration, immune senescence, AIDS, and other immune senescence disease; and to alter gene expression of senescent cells.

Tankyrases (TANKs) were identified as components of the human telomeric complex. They have also been proposed to have roles in regulation of the mitotic spindle and in vesicle trafficking and they may serve as scaffolds for proteins involved in various other cellular processes. Telomeres, which are essential for chromosome maintenance and stability, are maintained by telomerase, a specialized reverse transcriptase. TANKs are (ADP-ribose)transferases with some features of both signalling and cytoskeletal proteins. They contain the PARP domain, which catalyses poly-ADP-ribosylation of substrate proteins, the sterile alpha motif, which is shared with certain signalling molecules and the ANK domain, which contains 16 to 24 ankyrin repeats, also present in the cytoskeletal protein ankyrin. The ANK domain interacts with a variety of different proteins, including the telomeric protein, Telomere Repeat binding Factor-1 (TRF-1). These proteins were therefore named TRF1-interacting, ankyrin-related ADP-ribose polymerases (TANKs).

One function of TANKs is the ADP-ribosylation of TRF-1. Human telomere function is regulated by a complex of telomere associated proteins that includes the two telomere-specific DNA binding proteins, TRF-1 and TRF-2. TRF-2 protects chromosome ends, and TRF-1 regulates telomere length. ADP-ribosylation inhibits the ability of TRF-1 to bind to telomeric DNA. This poly-ADP-ribosylation of TRF-1 releases TRF-1 from the telomeres, thereby opening up the telomeric complex and allowing access to telomerase. Therefore, TANKs functions as positive regulators of telomere length, allowing elongation of the telomeres by telomerase.

Other roles for TANKs are suggested by the identity of proteins with which they interact—the insulin-responsive aminopeptidase, the Mcl1 proteins (which are members of the Bcl-2 family), the Epstein-Barr nuclear antigen-1, the nuclear and mitotic apparatus protein and the cytoplasmic and heterochromatic factor TAB182—and its various subcellular localizations (nuclear pores, Golgi apparatus and mitotic centrosomes).

Tankyrase-2 (TANK-2) differs from tankyrase-1 (TANK-1) in that it lacks an N-terminal HPS domain (comprised of homopolymeric repeats of His, Pro and Ser residues), found in TANK1. However, it probably has some overlapping functions with tankyrase-1, given that both proteins have similar sub-cellular localizations, associate with each other and bind many of the same proteins.

TANK-1 seems to be required for the polymerization of mitotic spindle-associated poly(ADP-ribose). The poly (ADP-ribosyl)ation activity of TANK-1 might be crucial for the accurate formation and maintenance of spindle bipolarity. Furthermore, PARP activity of TANK-1 has been shown to be required for normal telomere separation before anaphase. Interference with tankyrase PARP activity results in aberrant mitosis, which engenders a transient cell cycle arrest, probably due to spindle checkpoint activation, followed by cell death. Inhibition of tankyrases is therefore expected to have a cytotoxic effect on proliferating tumour cells.

As indicated above, the subcellular localization of several PARPs suggests a physiological role of poly(ADP-ribosyl)ation in the regulation of cell division.

PARP-1 and PARP-2 localize to centrosomes where they interact with kinetochore proteins. Ablation of the Parp-2 gene in mice causes significant DNA-damage-induced chromosome mis-segregation that is associated with kinetochore defects, which indicates that PARP-2 has a crucial guardian function in pericentric heterochromatin integrity. Furthermore PARP-1 associate with centrosomes linking the DNA-damage-surveillance network with the mitotic fidelity checkpoint.

The pivotal role of PARP in the repair of DNA strand breaks is well established, especially when caused directly by ionizing radiation or, indirectly after enzymatic repair of DNA lesions induced by methylating agents, topoisomerases I inhibitors and other chemotherapeutic agents as cisplatin and bleomycin. A variety of studies using "knockout" mice, trans-dominant inhibition models (over-expression of the DNA-binding domain), antisense and small molecular weight inhibitors have demonstrated the role of PARP in repair and cell survival after induction of DNA damage. The inhibition of PARP enzymatic activity should lead to an enhanced sensitivity of the tumour cells towards DNA damaging treatments.

PARP inhibitors have been reported to be effective in radiosensitizing (hypoxic) tumour cells and effective in preventing tumour cells from recovering from potentially lethal and sublethal damage of DNA after radiation therapy, presumably by their ability to prevent DNA strand break rejoining and by affecting several DNA damage signaling pathways.

U.S. Pat. No. 5,177,075 discusses several isoquinolines used for enhancing the lethal effects of ionizing radiation or chemotherapeutic agents on tumour cells. Weltin et al., ("Effect of 6(5-Phenanthridinone), an Inhibitor of Poly(ADP-ribose) Polymerase, on Cultured Tumour Cells", Oncol. Res., 6:9, 399-403 (1994)), discusses the inhibition of PARP activity, reduced proliferation of tumour cells, and a marked synergistic effect when tumour cells are co-treated with an alkylating drug.

Reviews of the state of the art has been published by Li and Zhang in IDrugs 2001, 4(7): 804-812, by Ame et al in Bioassays 2004, 26: 882-883 and by Nguewa et al., in Progress in Biophysic & Molecular Biology 2005, 88: 143-172.

Loss of PARP-1 increases the formation of DNA lesions that are repaired by homologous recombination without directly regulating the process of homologous recombination itself. Familial breast cancer is commonly associated with inherited defects in one of the BRCA1 or BRCA2 alleles. BRCA1 and BRCA2 are important for homologous recombination. The remaining functional BRCA1 or BRCA2 allele can be lost in some cells, thereby contributing to tumourigenisis. Thus, the tumours that arise are BRCA1 or BRCA2 deficient (e.g. BRCA2$^{-/-}$) whereas the somatic cells retain functional BRCA proteins (BRCA2$^{+/-}$). Inhibition of PARP activity in a BRCA1- or BRCA2-defective background might result in the generation of DNA lesions normally repaired by sister chromatid exchange, causing chromatid aberrations and loss of viability. Only relatively low levels of PARP-1 inhibitors may be required to produce a therapeutic effect given the acute sensitivity of the BRCA-defective cells. This is another example of a case where inhibitors of a normally non-essential DNA repair protein can be used as a single agent to treat tumours.

According to a review by Horvath and Szabo (Drug News Perspect 20(3), April 2007, 171-181) most recent studies demonstrated that PARP inhibitors enhance cancer cell death primarily because they interfere with DNA repair on various levels. More recent studies have also demonstrated that PARP inhibitors inhibit angiogenesis, either by inhibiting growth factor expression; or by inhibiting growth factor-induced cellular proliferative responses. These findings might also have implications on the mode of PARP inhibitors' anticancer effects in vivo.

Also a study by Tentori et al, Eur. J. Cancer, 2007, doi: 10.1016/j.ejca2007.07010 (in press) shows that PARP inhibitors abrogate VEGF or placental growth factor-induced migration and prevent formation of tubule-like networks in cell-based systems, and impair angiogenesis in vivo. The study also demonstrates that growth factor-induced angiogenesis is deficient in PARP-1 knock-out mice. The results of the study provide evidence for targeting PARP for anti-angiogenesis, adding novel therapeutic implications to the use of PARP inhibitors in cancer treatment.

There continues to be a need for effective and potent anticancer therapy that produce minimal side effects. The present invention provides compounds, compositions for, and methods of, inhibiting PARP activity for treating cancer. Furthermore they are useful in enhancing the effectiveness of chemotherapy and radiotherapy where a primary effect of the treatment with the compound is that of triggering cell death under conditions of DNA damage.

BACKGROUND PRIOR ART

EP 1487800, published on Oct. 2, 2005, discloses phenanthridinones as poly(ADP-ribose) polymerase inhibitors.

EP 1687277, published on Jun. 16, 2005, discloses 6-alkenyl and 6-phenylalkyl substituted 2-quinolinones and 2-quinoxalinones as poly(ADP-ribose) polymerase inhibitors.

EP 1709011, published on Jun. 16, 2005, discloses 6-phenylalkyl substituted 2-quinolinones and 2-quinoxalinones as poly(ADP-ribose) polymerase inhibitors.

EP 1709012, published on Jun. 16, 2005, discloses 6-substituted 2-quinolinones and 2-quinoxalinones as poly(ADP-ribose) polymerase inhibitors.

EP 1694653, published on Jun. 30, 2005, discloses substituted 6-cyclohexylalkyl substituted 2-quinolinones and 2-quinoxalinones as poly(ADP-ribose) polymerase inhibitors.

WO 2005/097750, published on Oct. 2, 2005, discloses substituted pyridones as poly(ADP-ribose) polymerase inhibitors.

WO 2006/003146, published on Jan. 12, 2006, discloses quinazolinones derivatives as poly(ADP-ribose) polymerase inhibitors.

WO 2006/003147, published on Jan. 12, 2006, discloses phthalazine derivatives as poly(ADP-ribose) polymerase inhibitors.

WO 2006/003148, published on Jan. 12, 2006, discloses quinazolinedione derivatives as poly(ADP-ribose) polymerase inhibitors.

WO 2006/003150, published on Jan. 12, 2006, discloses substituted 2-alkyl quinazolinone derivatives as poly(ADP-ribose) polymerase inhibitors.

WO 2007/025009, published on Mar. 1, 2007, discloses indenoisoquinolinone analogs as poly(ADP-ribose) polymerase inhibitors.

WO 2007/095628, published on Aug. 23, 2007, discloses pyrazoloquinolinones as potent PARP inhibitors.

DESCRIPTION OF THE INVENTION

This invention concerns compounds of formula (I):

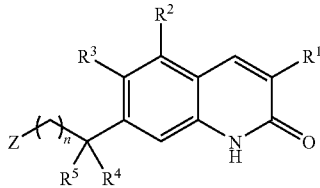
(I)

the N-oxide forms, the pharmaceutically acceptable addition salts, the quaternary ammonium salts and the stereochemically isomeric forms thereof, wherein n is 0, 1 or 2;

$R^1$ is $C_{1-3}$alkyl;

$R^2$ and $R^3$ are each independently selected from hydrogen, halogen, $C_{1-6}$alkyl, cyano, hydroxy, $C_{1-6}$alkyloxy, $C_{3-6}$cycloalkyloxy, cyano$C_{1-4}$alkyl, hydroxy$C_{1-4}$alkyloxy, $C_{1-4}$alkyloxy$C_{1-4}$alkyloxy, amino$C_{1-4}$alkyloxy, $C_{1-4}$alkylamino$C_{1-4}$alkyloxy, di($C_{1-4}$alkyl)amino$C_{1-4}$alkyloxy, aminocarbonyl or $C_{2-4}$alkynyl;

$R^4$ and $R^5$ are each independently selected from hydrogen, $C_{1-6}$alkyl, $C_{3-6}$cycloalkyl, hydroxy, $C_{1-6}$alkyloxy, $C_{1-6}$alkyloxymethyl or hydroxy$C_{1-6}$alkyl, or $R^4$ and $R^5$ together form =O;

Z is a group of formula —$NR^6R^7$ wherein $R^6$ is hydrogen or $C_{1-4}$alkyl;

$R^7$ is $C_{1-4}$alkyloxy$C_{1-4}$alkyl or a group of formula

—$(CH_2)_t$-$L^1$ (a-1)

wherein t is 0, 1, 2 or 3 and $L^1$ is phenyl or phenyl substituted with one or two substituents independently selected from hydrogen, halo, cyano, $C_{1-4}$alkyl, $C_{1-4}$alkyloxy, hydroxycarbonyl, $C_{1-4}$alkyloxycarbonyl or aminocarbonyl;

or $L^1$ is a heterocyclic ring system selected from:

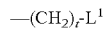
(b-1)

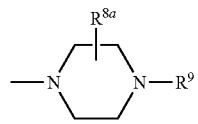
(b-2)

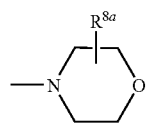
(b-3)

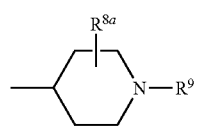
(b-4)

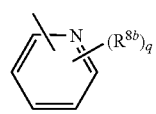

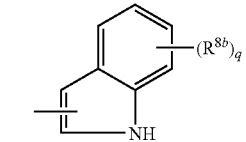
(b-5)

wherein $R^{8a}$ is selected from hydrogen, $C_{1-4}$alkyl, hydroxy$C_{1-4}$alkyl or aminocarbonyl; q is 0, 1 or 2; and each $R^{8b}$ is independently selected from hydrogen, halogen, cyano, $C_{1-4}$alkyl, hydroxy$C_{1-4}$alkyl, $C_{1-4}$alkyloxy or aminocarbonyl; and $R^9$ is hydrogen, $C_{1-4}$alkyl, phenyl or a heterocyclic ring system selected from:

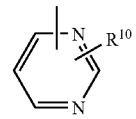
(c-1)

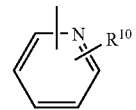
(c-2)

wherein $R^{10}$ is selected from hydrogen, halogen, cyano, $C_{1-4}$alkyl or $C_{1-4}$alkyloxy;

or Z is a heterocyclic ring system selected from:

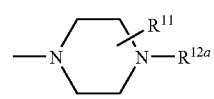
(d-1)

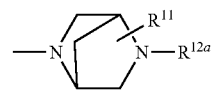
(d-2)

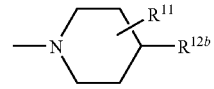
(d-3)

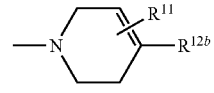
(d-4)

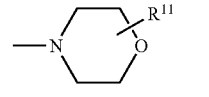
(d-5)

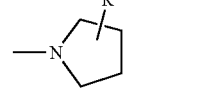
(d-6)

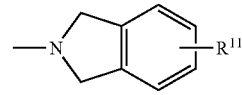
(d-7)

-continued

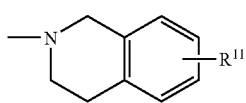
(d-8)

wherein $R^{11}$ is hydrogen, $C_{1-4}$alkyl, hydroxyl, cyano, hydroxy$C_{1-4}$alkyl or aminocarbonyl; and
$R^{12a}$ is hydrogen or $C_{1-4}$alkyloxy$C_{1-4}$alkyl;

or —X-$L^2$ (e-1)

$R^{12b}$ is hydrogen, $C_{1-4}$alkyloxy$C_{1-4}$alkyl or $C_{1-6}$alkyloxy$C_{1-6}$alkylamino;

or —X-$L^2$ (e-1)

X is —$(CH_2)_p$— in which p is 0, 1, 2 or 3;
$L^2$ is $C_{3-6}$cycloalkyl, phenyl or phenyl substituted with one or two substituents independently selected from halo, $C_{1-4}$alkyl, $C_{1-4}$alkyloxy, amino, cyano or trifluoromethyl; or $L^2$ is a heterocyclic ring system selected from:

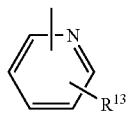
(f-1)

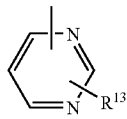
(f-2)

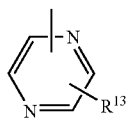
(f-3)

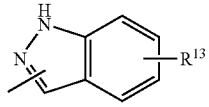
(f-4)

wherein $R^{13}$ is selected from hydrogen, halo, $C_{1-4}$alkyl, $C_{1-4}$alkyloxy, $C_{2-4}$alkynyl, aminocarbonyl, cyano, trifluoromethyl, amino, hydroxy$C_{1-4}$alkylaminocarbonyl, hydroxycarbonyl or $C_{1-4}$alkyloxycarbonyl.

The compounds of formula (I) and the intermediates of the invention may also exist in their tautomeric forms. Such forms although not explicitly indicated in the above formula are intended to be included within the scope of the present invention.

Whenever the heterocyclic ring systems in Z contain a —$CH_2$—, —CH=, or —NH— moiety the substituents or the rest of the molecule can be attached to each carbon or nitrogen atom in which case one or both hydrogen atoms are replaced.

A number of terms used in the foregoing definitions and hereinafter are explained hereunder. These terms are sometimes used as such or in composite terms.

As used in the foregoing definitions and hereinafter, halo is generic to fluoro, chloro, bromo and iodo; $C_{1-6}$alkyl defines straight and branched chain saturated hydrocarbon radicals having from 1 to 6 carbon atoms such as, e.g. methyl, ethyl, propyl, butyl, pentyl, hexyl, 1-methylethyl, 2-methylpropyl, 2-methyl-butyl, 2-methylpentyl and the like; $C_{2-4}$alkynyl defines straight and branch chained hydrocarbon radicals containing one triple bond and having from 2 to 4 carbon atoms, such as, for example, ethynyl, 2-propynyl, 3-butynyl, 2-butynyl, and the like; $C_{3-6}$cycloalkyl includes cyclic hydrocarbon groups having from 3 to 6 carbons, such as cyclopropyl, cyclobutyl, cyclopentyl, cyclopentenyl, cyclohexyl and the like.

The term "pharmaceutically acceptable addition salts" means pharmaceutically acceptable acid or base addition salts. The pharmaceutically acceptable acid or base addition salts as mentioned hereinabove are meant to comprise the therapeutically active non-toxic acid and non-toxic base addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butane-dioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms which the compounds of formula (I) are able to form. Examples of such forms are e.g. hydrates, alcoholates and the like.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

A quaternary ammonium salt of a compound according to formula (I) defines said compound which is able to form by a reaction between a basic nitrogen of a compound according to formula (I) and an appropriate quaternizing agent, such as, for example, an optionally substituted alkylhalide, arylhalide or arylalkylhalide, in particular methyliodide and benzyliodide. Other reactants with good leaving groups may also be used, such as, for example, alkyl trifluoromethanesulfonates, alkyl methanesulfonates and alkyl p-toluenesulfonates. A quaternary ammonium salt has at least one positively charged nitrogen. Pharmaceutically acceptable counterions include chloro, bromo, iodo, trifluoroacetate and acetate ions.

The term "stereochemically isomeric forms" of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Of special interest are those compounds of formula (I) which are stereochemically pure. Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, respectively the diastereomeric excess of the mixture in question.

The tautomeric forms of the compounds of formula (I) are meant to comprise those compounds of formula (I) wherein e.g. an enol group is converted into a keto group (keto-enol tautomerism).

The N-oxide forms of the compounds of formula (I) are meant to comprise those compounds of formula (I) wherein one or several nitrogen atoms are oxidized to the so-called N-oxide, particularly those N-oxides wherein one or more of the piperidine- or piperazine nitrogens are N-oxidized.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

The present invention is also intended to include any isotopes of atoms present in the compounds of the invention. For example, isotopes of hydrogen include tritium and deuterium and isotopes of carbon include C-13 and C-14.

Whenever used hereinafter, the term "compounds of formula (I)" is meant to include also the N-oxide forms, the pharmaceutically acceptable acid or base addition salts and all stereoisomeric forms.

According to an embodiment of the invention we provide compounds of formula (I), the N-oxide forms, the pharmaceutically acceptable addition salts, the quaternary ammonium salts and the stereochemically isomeric forms thereof, wherein one or more of the following restrictions apply:

n is 0, 1 or 2;
$R^1$ is $C_{1-3}$alkyl;
$R^2$ and $R^3$ are each independently selected from hydrogen, halogen, $C_{1-6}$alkyl, cyano, hydroxy or $C_{1-6}$alkyloxy;
$R^4$ and $R^5$ are each independently selected from hydrogen, $C_{1-6}$alkyl, $C_{3-6}$cycloalkyl, hydroxy, $C_{1-6}$alkyloxy, $C_{1-6}$alkyloxymethyl or hydroxy$C_{1-6}$alkyl, or $R^4$ and $R^5$ together form =O;
Z is a group of formula —$NR^6R^7$ wherein
$R^6$ is hydrogen or $C_{1-4}$alkyl;
$R^7$ is $C_{1-4}$alkyloxy$C_{1-4}$alkyl or a group of formula —(CH$_2$)$_t$-L$^1$ (a-1)

wherein t is 0, 1, 2 or 3 and $L^1$ is phenyl or phenyl substituted with one or two substituents independently selected from hydrogen, halo, cyano, $C_{1-4}$alkyl or $C_{1-4}$alkyloxy;
or $L^1$ is a heterocyclic ring system selected from:

(b-1)

(b-2)

(b-3)

(b-4)

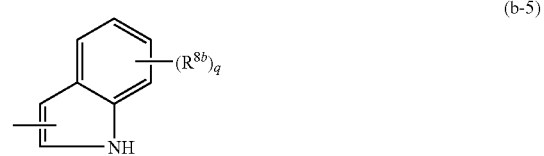
(b-5)

wherein $R^{8a}$ is selected from hydrogen, $C_{1-4}$alkyl, hydroxy$C_{1-4}$alkyl or aminocarbonyl; q is 0 or 1; and each $R^{8b}$ is independently selected from hydrogen, halogen, cyano, $C_{1-4}$alkyl, hydroxy$C_{1-4}$alkyl, $C_{1-4}$alkyloxy or aminocarbonyl; and
$R^9$ is hydrogen, $C_{1-4}$alkyl, phenyl or a heterocyclic ring system selected from:

(c-1)

(c-2)

to wherein $R^{10}$ is selected from hydrogen, halogen, cyano, $C_{1-4}$alkyl or $C_{1-4}$alkyloxy;

or Z is a heterocyclic ring system selected from:

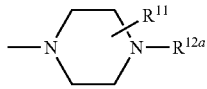 (d-1)

 (d-2)

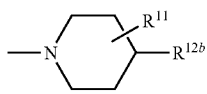 (d-3)

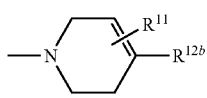 (d-4)

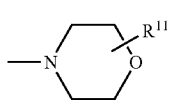 (d-5)

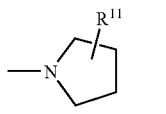 (d-6)

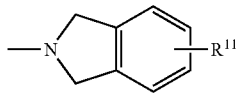 (d-7)

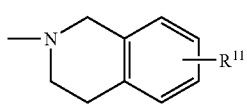 (d-8)

wherein $R^{11}$ is hydrogen or $C_{1-4}$alkyl; and
$R^{12a}$ is hydrogen or $C_{1-4}$alkyloxy$C_{1-4}$alkyl;

or —X-L² (e-1)

$R^{12b}$ is hydrogen, $C_{1-4}$alkyloxy$C_{1-4}$alkyl or $C_{1-6}$alkyloxy$C_{1-6}$alkylamino;

or —X-L² (e-1)

X is —(CH$_2$)$_p$— in which p is 0, 1, 2 or 3;
L² is phenyl or phenyl substituted with one or two substituents independently selected from halo, $C_{1-4}$alkyl, $C_{1-4}$alkyloxy, amino, cyano or trifluoromethyl; or
L² is a heterocyclic ring system selected from:

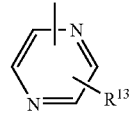 (f-1)

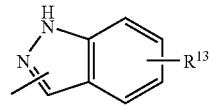 (f-2)

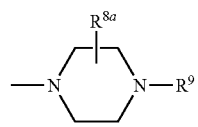 (f-3)

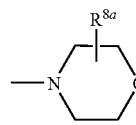 (f-4)

wherein $R^{13}$ is selected from hydrogen, halo, $C_{1-4}$alkyl, $C_{1-4}$alkyloxy, $C_{2-4}$alkynyl, aminocarbonyl, cyano, trifluoromethyl, amino, hydroxy$C_{1-4}$alkylaminocarbonyl, hydroxycarbonyl or $C_{1-4}$alkyloxycarbonyl.

According to a further embodiment of the invention we provide compounds of formula (I), the N-oxide forms, the pharmaceutically acceptable addition salts, the quaternary ammonium salts and the stereochemically isomeric forms thereof, wherein one or more of the following restrictions apply:

n is 0, 1 or 2;

$R^1$ is methyl or ethyl;

$R^2$ is selected from hydrogen, methyl, ethyl, cyano or methyloxy;

$R^3$ is hydrogen;

$R^4$ and $R^5$ are each independently selected from hydrogen, $C_{1-6}$alkyl, $C_{3-6}$cycloalkyl, hydroxy or hydroxy$C_{1-6}$alkyl, or $R^4$ and $R^5$ together form =O;

Z is a group of formula —NR⁶R⁷ wherein $R^6$ is hydrogen or $C_{1-4}$alkyl;

$R^7$ is $C_{1-4}$alkyloxy$C_{1-4}$alkyl or a group of formula:

—(CH$_2$)$_t$-L¹ (a-1)

wherein t is 0, 1, 2 or 3 and L¹ is phenyl or phenyl substituted with one or two halo substituents;

or L¹ is a heterocyclic ring system selected from:

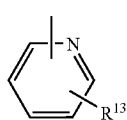 (b-1)

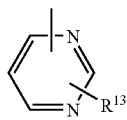 (b-2)

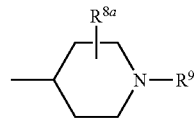 (b-3)

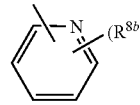 (b-4)

-continued

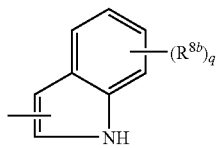
(b-5)

wherein $R^{8a}$ is hydrogen; q is 0; and
$R^9$ is hydrogen or the heterocyclic ring system (c-1):

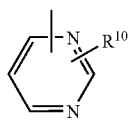
(c-1)

wherein $R^{10}$ is hydrogen;
or Z is a heterocyclic ring system selected from:

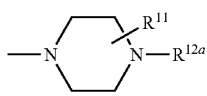
(d-1)

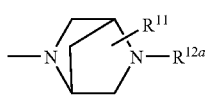
(d-2)

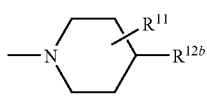
(d-3)

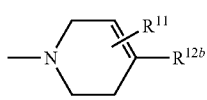
(d-4)

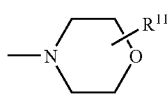
(d-5)

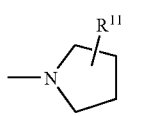
(d-6)

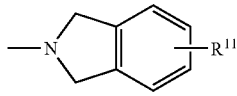
(d-7)

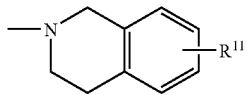
(d-8)

wherein $R^{11}$ is hydrogen; and
$R^{12a}$ is hydrogen or $C_{1-4}$alkyloxy$C_{1-4}$alkyl;

or —X-L²                 (e-1)

$R^{12b}$ is hydrogen or $C_{1-6}$alkyloxy$C_{1-6}$alkylamino;

or —X-L²                 (e-1)

X is —(CH₂)$_p$— in which p is 0, 1 or 2;

$L^2$ is phenyl or phenyl substituted with one or two substituents independently selected from halo, $C_{1-4}$alkyl, $C_{1-4}$alkyloxy or cyano; or $L^2$ is a heterocyclic ring system selected from:

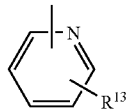
(f-1)

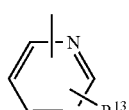
(f-2)

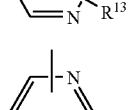
(f-3)

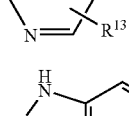
(f-4)

wherein $R^{13}$ is selected from hydrogen, chloro, aminocarbonyl, cyano, $C_{1-4}$alkyloxy, trifluoromethyl, hydroxy$C_{1-4}$alkylaminocarbonyl, hydroxycarbonyl or $C_{1-4}$alkyloxycarbonyl.

According to a further embodiment of the invention we provide compounds of formula (I), the N-oxide forms, the pharmaceutically acceptable addition salts, the quaternary ammonium salts and the stereochemically isomeric forms thereof, wherein one or more of the following restrictions apply:

n is 0;
$R^1$ is methyl or ethyl;
$R^2$ is hydrogen or methyloxy;
$R^3$ is hydrogen;
$R^4$ and $R^5$ are each hydrogen;
Z is a group of formula —NR⁶R⁷ wherein
$R^6$ is hydrogen or $C_{1-4}$alkyl;
$R^7$ is $C_{1-4}$alkyloxy$C_{1-4}$alkyl or a group of formula

—(CH₂)$_t$-L¹              (a-1)

wherein t is 0, 1, 2 or 3 and $L^1$ is phenyl or phenyl substituted with one or two halo substituents; or $L^1$ is a heterocyclic ring system selected from:

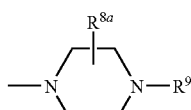
(b-1)

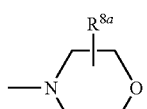
(b-2)

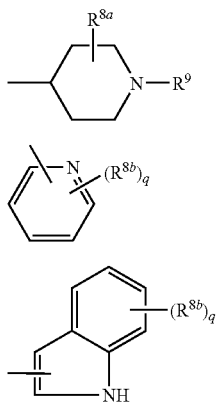
(b-3)
(b-4)
(b-5)

wherein R^{8a} is hydrogen; q is 0; and
R^9 is hydrogen or the heterocyclic ring system (c-1):

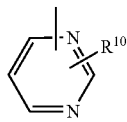
(c-1)

wherein R^{10} is hydrogen.

According to a further embodiment of the invention we provide compounds of formula (I), the N-oxide forms, the pharmaceutically acceptable addition salts, the quaternary ammonium salts and the stereochemically isomeric forms thereof, wherein one or more of the following restrictions apply:

n is 0, 1 or 2;
$R^1$ is $C_{1-3}$alkyl;
$R^2$ is hydrogen or methyloxy;
$R^3$ is hydrogen;
$R^4$ and $R^5$ are each independently selected from hydrogen, $C_{1-6}$alkyl, hydroxy, or hydroxy$C_{1-6}$alkyl, or $R^4$ and $R^5$ together form =O;
Z is a heterocyclic ring system selected from:

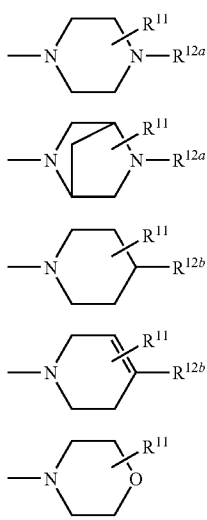
(d-1)
(d-2)
(d-3)
(d-4)
(d-5)

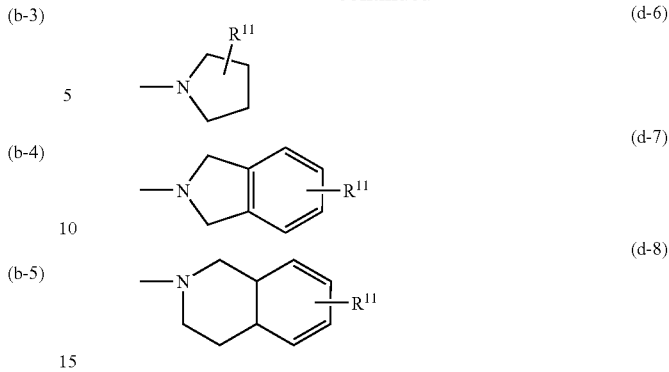
(d-6)
(d-7)
(d-8)

wherein $R^{11}$ is hydrogen;
$R^{12a}$ is hydrogen or $C_{1-4}$alkyloxy$C_{1-4}$alkyl;

or —X-$L^2$ (e-1)

X is —$(CH_2)_p$— in which p is 0 or 2;
$L^2$ is phenyl or phenyl substituted with one or two substituents independently selected from halo, $C_{1-4}$alkyl, $C_{1-4}$alkyloxy or cyano; or $L^2$ is a heterocyclic ring system selected from:

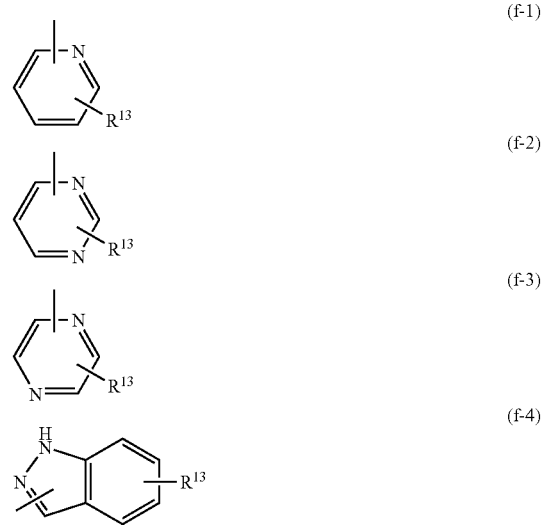
(f-1)
(f-2)
(f-3)
(f-4)

wherein $R^{13}$ is selected from hydrogen, aminocarbonyl, cyano, $C_{1-4}$alkyloxy, trifluoromethyl, hydroxy$C_{1-4}$alkylaminocarbonyl, hydroxycarbonyl or $C_{1-4}$alkyloxycarbonyl;
$R^{12b}$ is hydrogen or $C_{1-6}$alkyloxy$C_{1-6}$alkylamino;

or —X-$L^2$ (e-1)

X is —$(CH_2)_p$— in which p is 0 or 1;
$L^2$ is phenyl or phenyl substituted with one or two halo substituents; or
$L^2$ is a heterocyclic ring system selected from:

(f-1)

(f-2)

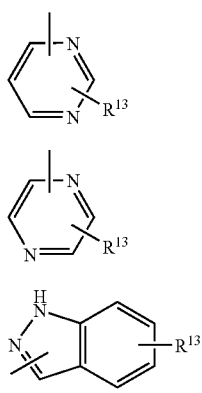

(f-3)

(f-4)

wherein R[13] is selected from hydrogen, chloro, aminocarbonyl, cyano, methyloxy, trifluoromethyl, hydroxy $C_{1-4}$alkylaminocarbonyl, hydroxycarbonyl or $C_{1-4}$alkyloxycarbonyl.

In the compounds according to the invention the heterocyclic ring systems of formulae (b-1) to (b-5) represented by $L^1$ are preferably selected from:

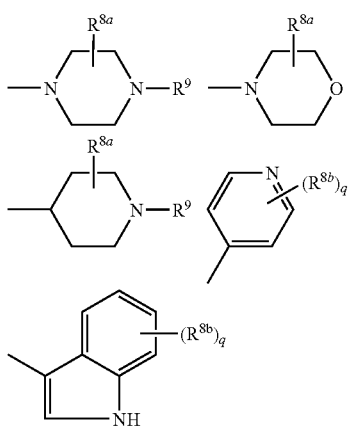

wherein $R^{8a}$, $R^{8b}$ and $R^9$ are as defined above.

In the compounds according to the invention the heterocyclic ring systems of formulae (c-1) and (c-2), represented by $R^9$, are preferably selected from:

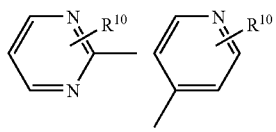

wherein $R^{10}$ is as defined above.

In the compounds according to the invention the heterocyclic ring systems of formulae (d-1) to (d-8), represented by Z, are preferably selected from:

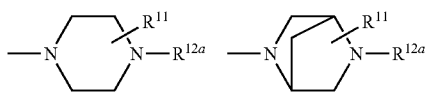

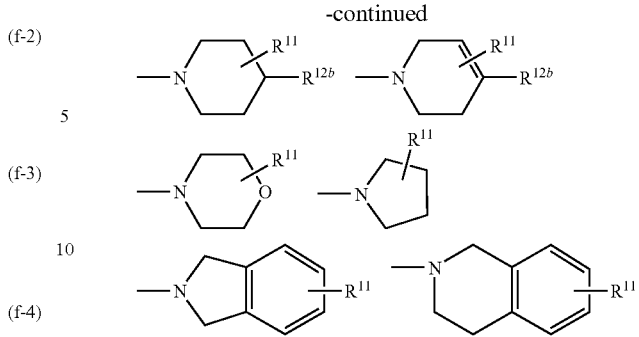

wherein $R^{11}$, $R^{12a}$ and $R^{12b}$ are as defined above.

In the compounds according to the invention the heterocyclic ring systems of formulae (f-1) to (f-4) represented by $L^2$ are preferably selected from:

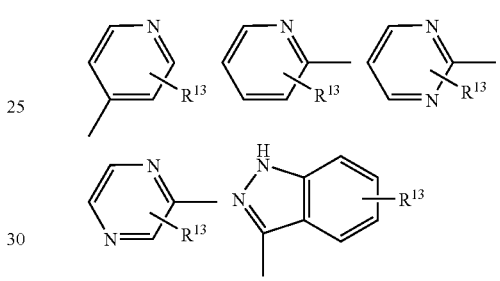

wherein $R^{13}$ is as defined above.

Further preferred heterocyclic ring systems represented by Z in formula (I) include:

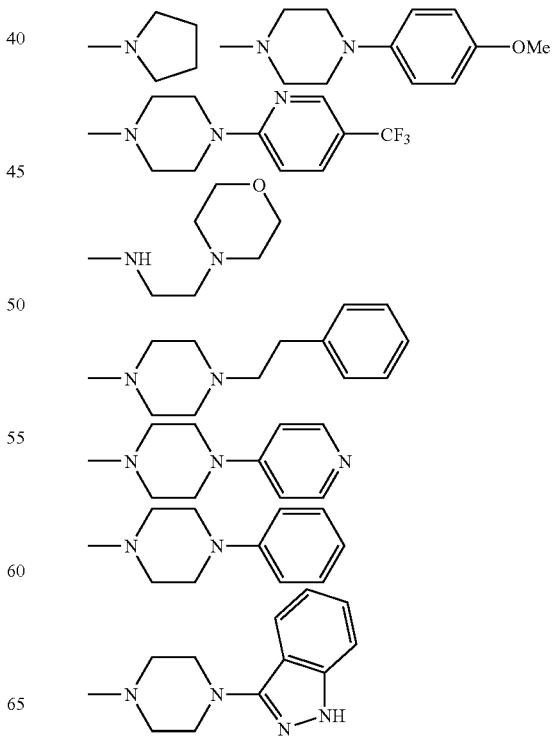

-continued

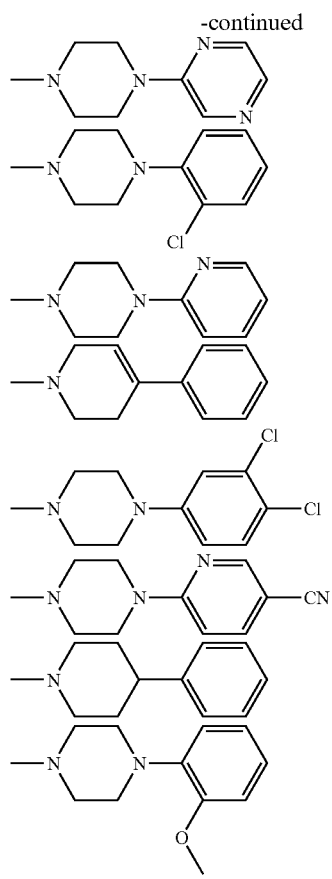

According to a further embodiment of the invention we provide a preferred group of compounds of formula (I), the N-oxide forms, the pharmaceutically acceptable addition salts, the quaternary ammonium salts and the stereochemically isomeric forms thereof, wherein one or more of the following restrictions apply:

n is 0;
$R^1$ is methyl or ethyl;
$R^2$ and $R^3$ are each hydrogen;
$R^4$ and $R^5$ are each independently selected from hydrogen or $C_{1-6}$alkyl;
Z is a heterocyclic ring system selected from:

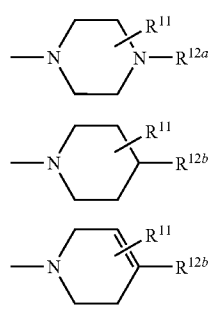 (d-1)

(d-3)

(d-4)

wherein $R^{11}$ is hydrogen;
$R^{12a}$ and $R^{12b}$ are each —X-$L^2$ (e-1)
X is —(CH$_2$)$_p$— in which p is 0 or 2;
$L^2$ is phenyl or phenyl substituted with one or two substituents independently selected from halo, $C_{1-4}$alkyloxy or cyano; or $L^2$ is a heterocyclic ring system selected from:

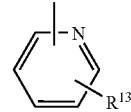 (f-1)

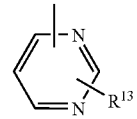 (f-2)

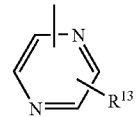 (f-3)

wherein $R^{13}$ is selected from hydrogen, chloro, cyano, trifluoromethyl, methyloxy or hydroxy-$C_{1-4}$alkylaminocarbonyl.

According to a further embodiment of the invention we provide a further preferred group of compounds of formula (I), the N-oxide forms, the pharmaceutically acceptable addition salts, the quaternary ammonium salts and the stereochemically isomeric forms thereof, wherein one or more of the following restrictions apply:

n is 0;
$R^1$ is methyl or ethyl;
$R^2$ and $R^3$ are each hydrogen;
$R^4$ and $R^5$ are each independently selected from hydrogen or $C_{1-6}$alkyl;
Z is a heterocyclic ring system of formula (d-1):

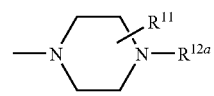 (d-1)

wherein $R^{11}$ is hydrogen; and
$R^{12a}$ is —X-$L^2$ (e-1)
X is —(CH$_2$)$_p$— in which p is 0 or 2; and
$L^2$ is phenyl or phenyl substituted with a substituent selected from halo, $C_{1-4}$alkyloxy or cyano, preferably in the ortho-position; or $L^2$ is a heterocyclic ring system selected from:

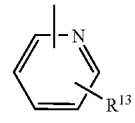 (f-1)

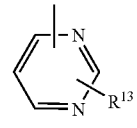 (f-2)

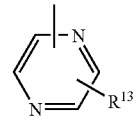 (f-3)

wherein $R^{13}$ is selected from hydrogen, chloro, cyano, trifluoromethyl, methyloxy or hydroxy-$C_{1-4}$alkylaminocarbonyl.

According to a further embodiment of the invention we provide a further preferred to group of compounds of formula (I), the N-oxide forms, the pharmaceutically acceptable addition salts, the quaternary ammonium salts and the stereochemically isomeric forms thereof, wherein one or more of the following restrictions apply:

n is 0;

$R^1$ is methyl or ethyl;

$R^2$ and $R^3$ are each hydrogen;

$R^4$ and $R^5$ are each independently selected from hydrogen or $C_{1-6}$alkyl;

Z is a heterocyclic ring system selected from:

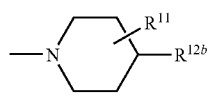

(d-3)

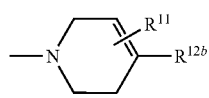

(d-4)

wherein $R^{11}$ is hydrogen; and $R^{12b}$ is —X-$L^2$ (e-1)

X is —$(CH_2)_p$— in which p is 0; and $L^2$ is phenyl or phenyl substituted with one or two halo substituents.

According to a further embodiment of the invention we provide an especially preferred group of compounds of formula (I), the N-oxide forms, the pharmaceutically acceptable addition salts, the quaternary ammonium salts and the stereochemically isomeric forms thereof, wherein one or more of the following restrictions apply:

n is 0;

$R^1$ is methyl or ethyl;

$R^2$ and $R^3$ are each hydrogen;

$R^4$ and $R^5$ are each independently selected from hydrogen or $C_{1-6}$alkyl;

Z is a heterocyclic ring system selected from:

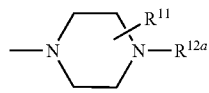

(d-1)

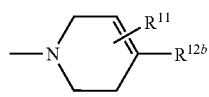

(d-4)

wherein $R^{11}$ is hydrogen; and $R^{12a}$ and $R^{12b}$ are each —X-$L^2$ (e-1)

X is —$(CH_2)_p$— in which p is 0;

$L^2$ is phenyl or phenyl substituted with a substituent selected from halo, $C_{1-4}$alkyloxy or cyano, preferably in the ortho-position; or $L^2$ is a heterocyclic ring system of formula (f-1):

(f-1)

wherein $R^{13}$ is selected from hydrogen, chloro, cyano, methyloxy or trifluoromethyl.

According to a further preferred embodiment of the invention, the compounds of formula (I) and the above-defined groups of compounds of formula (I) include those wherein one or more of the following restrictions apply:

$R^1$ is $C_{1-3}$alkyl selected from methyl or ethyl when at least one of $R^4$ and $R^5$ is $C_{1-6}$alkyl one or both such groups are independently methyl or isopropyl, and when at least one of $R^4$ and $R^5$ is hydroxy$C_{1-6}$alkyl one or both such groups are hydroxymethyl;

when $R^6$ is $C_{1-4}$alkyl such a group is preferably methyl;

when $R^7$ is $C_{1-4}$alkyloxy$C_{1-4}$alkyl such a group is preferably methyloxyethyl;

when $L^1$ is phenyl substituted with halo such a substituent is preferably fluoro;

when $R^{12a}$ is $C_{1-4}$alkyloxy$C_{1-4}$alkyl such a group is preferably methyloxyethyl;

when $R^{12b}$ is $C_{1-6}$alkyloxy$C_{1-6}$alkylamino such a group is preferably methyloxyethylamino;

when $L^2$ is phenyl substituted with halo such a substituent is preferably chloro or fluoro, and when substituted with $C_{1-4}$alkyloxy such a substituent is preferably methyloxy;

when $L^2$ is phenyl substituted with a substituent such a substituent is preferably in the ortho-position;

when $R^{13}$ is hydroxy$C_{1-4}$alkylaminocarbonyl, such a group is preferably hydroxyethylaminocarbonyl and when $R^{13}$ is $C_{1-4}$alkyloxycarbonyl such a group is ethyloxycarbonyl.

Especially preferred compounds according to the invention include the following compounds and the N-oxide forms, the pharmaceutically acceptable addition salts, the quaternary ammonium salts and the stereochemically isomeric forms thereof, namely Compounds 17, 18, 20, 21, 22 and 23.

The compounds of formula (I) can be prepared according to the general methods described herein below. The starting materials and some of the intermediates are known compounds and are commercially available or may be prepared according to conventional reaction procedures generally known in the art.

Some preparation methods will be described hereinafter in more detail. Other methods for obtaining final compounds of formula (I) are described in the examples.

Compounds of formula (I) in which n is 0 and at least one of $R^4$ and $R^5$ is other than hydrogen, represented by formula (I-a), can be prepared in accordance with reaction scheme A:

Scheme A

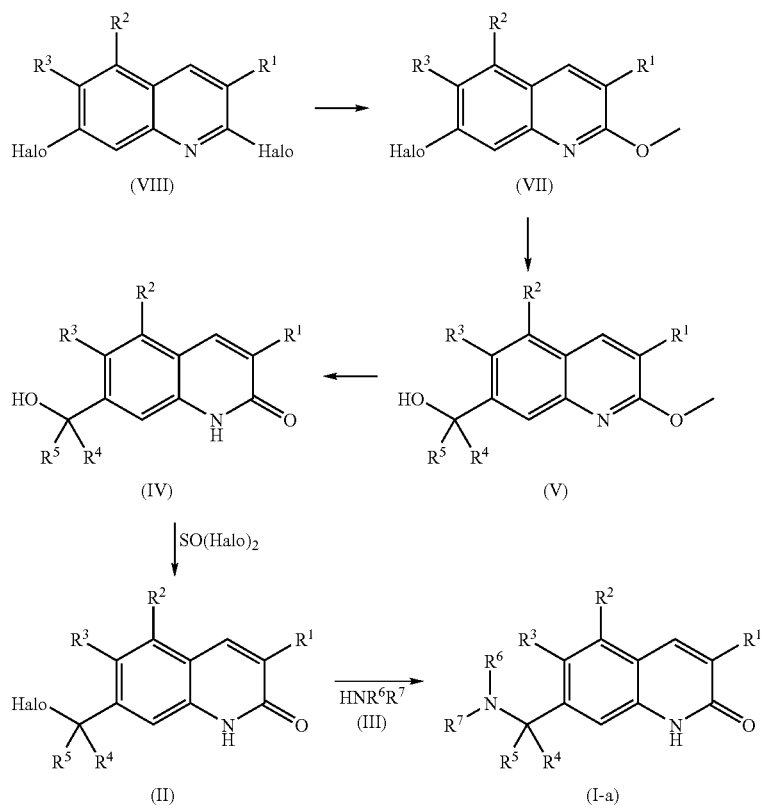

In the above scheme the individual stages may be carried out for example as follows:

a) a compound of formula (VIII), wherein each Halo is independently a halogen atom such as chlorine or bromine, is treated with sodium methoxide in methanol;

b) the resulting compound of formula (VII) is converted into a compound of formula (V) by treatment with an organolithium compound such as n-butyl lithium in an appropriate solvent such as tetrahydrofuran and subsequently reacting said intermediate with an appropriate aldehyde ($R^4$CHO) or a ketone ($R^4$CO$R^5$);

c) the resulting compound of formula (V) is hydrolysed for example by treating with hydrochloric acid in an appropriate solvent such as dioxane;

d) the resulting compound of formula (IV) is halogenated for example with a thionyl halide for example thionyl chloride in an appropriate solvent such as dichloromethane;

e) the resulting compound of formula (II) is reacted with an amine of formula (III), under basic conditions for example in the presence of potassium carbonate in an appropriate solvent such as acetonitrile or DMF to form a compound of formula (I-a).

Compounds of formula (V) where $R^5$ is hydrogen can alternatively be prepared by reacting a compound of formula (VI) with an appropriate reagent such as $R^4$MgX wherein X is a halogen atom for example a chlorine or a bromine atom, in an appropriate solvent such as tetrahydrofuran: The reagent employed can also be an organolithium compound such as butyllithium.

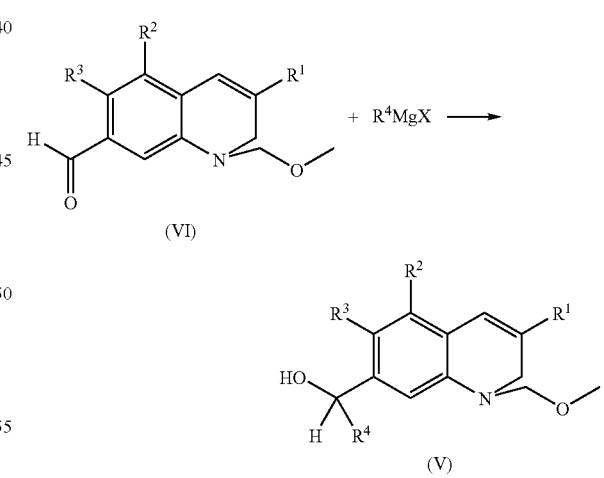

The compound of formula (VI) may be prepared by treating a compound of formula (VII) above, with an organolithium compound such as n-butyl lithium in an appropriate solvent such as tetrahydrofuran and subsequently reacting said intermediate with N-formylpiperidine or DMF.

Compounds of formula (I) in which n is 0 and $R^4$ and $R^5$ are each hydrogen, represented by formula (I-b), can be prepared in accordance with reaction scheme B:

Scheme B

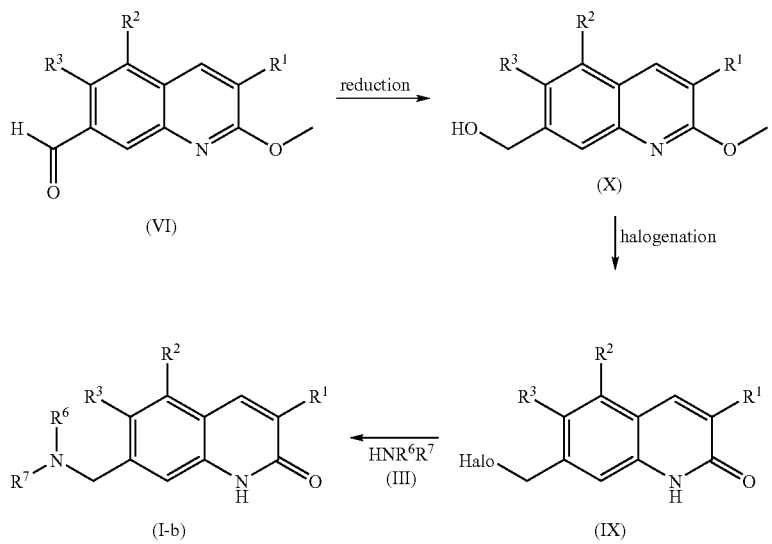

In the above scheme the individual stages may be carried out for example as follows:

a) a compound of formula (VI) is reduced for example with sodium borohydride in an appropriate solvent such as methanol;

b) the resulting compound of formula (X) is halogenated for example by treatment with hydrobromic acid;

c) the resulting compound of formula (IX) is reacted with an amine of formula (III) under basic conditions for example in the presence of potassium carbonate in an appropriate solvent such as acetonitrile or DMF to form a compound of formula (I-b).

Compounds of formula (I) in which n is 0, one of $R^4$ and $R^5$ is a hydroxymethyl group and the other of $R^4$ and $R^5$ is hydrogen, represented by formula (I-c), can be prepared in accordance with reaction scheme C below:

Scheme C

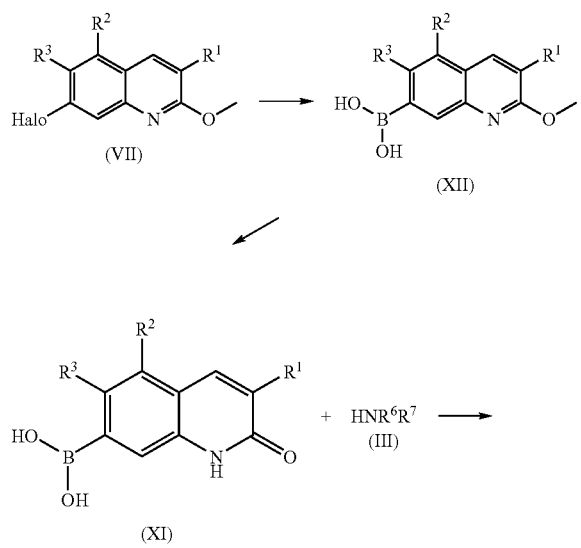

-continued

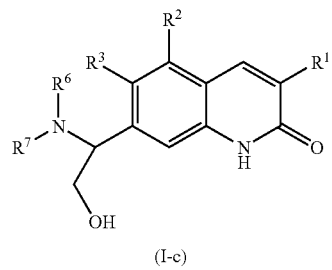

In the above scheme the individual stages may be carried out for example as follows:

a) a compound of formula (XII) above is reacted a with an organolithium compound such as n-butyl lithium in an appropriate solvent such as tetrahydrofuran and subsequently reacting said compound with trimethyloxyboron ($B(OCH_3)_3$) to form a compound of formula (XII);

b) the resulting compound of formula (XII) is converted into a compound of formula (XI) by hydrolysis for example by treating with hydrochloric acid in an appropriate solvent such as dioxane;

c) the resulting compound of formula (XI) is reacted with an amine of formula (III) and glycolaldehyde in hexafluoroisopropanol or a mixture of dichloromethane and hexafluoroisopropanol to form a compound of formula (I-c).

Compounds of formula (I) in which n is 1, one of $R^4$ and $R^5$ is hydroxyl and the other $R^4$ and $R^5$ is hydrogen, represented by formula (I-d), can be prepared in accordance with reaction scheme D below:

Scheme D

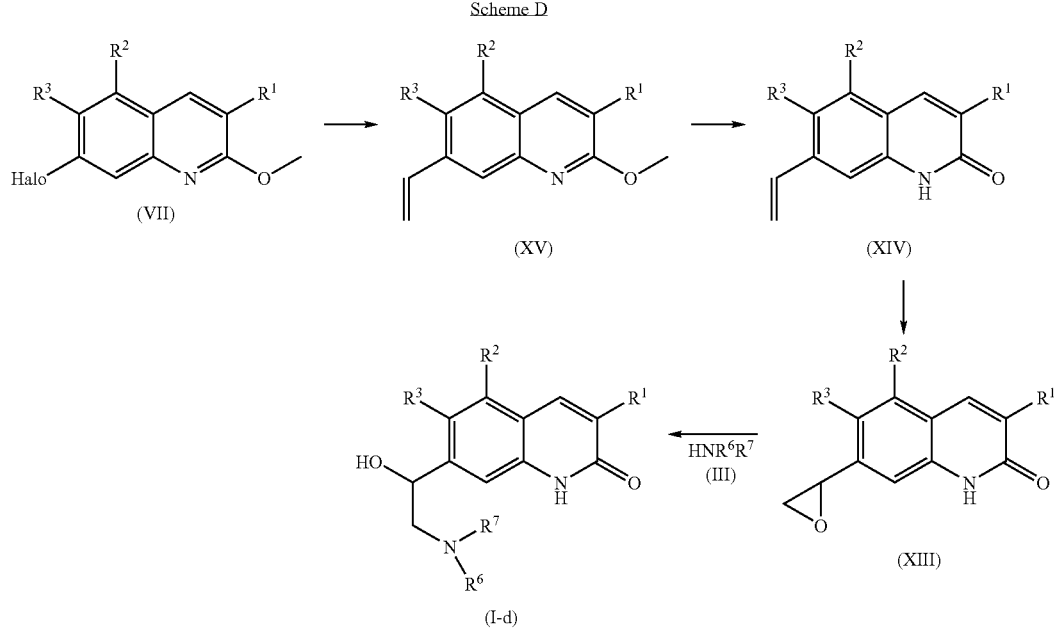

In the above scheme the individual stages may be carried out for example as follows:

a) a compounds a compound of formula (VII) is treated with tributyl(vinyl)tin in the presence of $Pd(PPh_3)_2Cl_2$ in an appropriate solvent such as toluene to form a compound of formula (XV);

b) the resulting compound of formula (XV) is hydrolysed for example by treating with hydrochloric acid in an appropriate solvent such as tetrahydrofuran to form a compound of formula (XIV);

c) the resulting compound of formula (XIV) is treated with m-chloroperoxybenzoic acid (CPBA) in an appropriate solvent such as dichloromethane to form a compound of formula (XIII);

d) the resulting compound of formula (XIII) is reacted with an amine of formula (III) in an appropriate solvent such as tetrahydrofuran to form a compound of formula (I-d).

Compounds of formula (I) in which n is 1, $R^4$ is hydrogen and $R^5$ is other than hydroxyl, represented by formula (I-e), can be prepared in accordance with scheme E below in which $R^{5a}$ has the meanings defined for $R^5$ with the exception of hydroxyl:

Scheme E

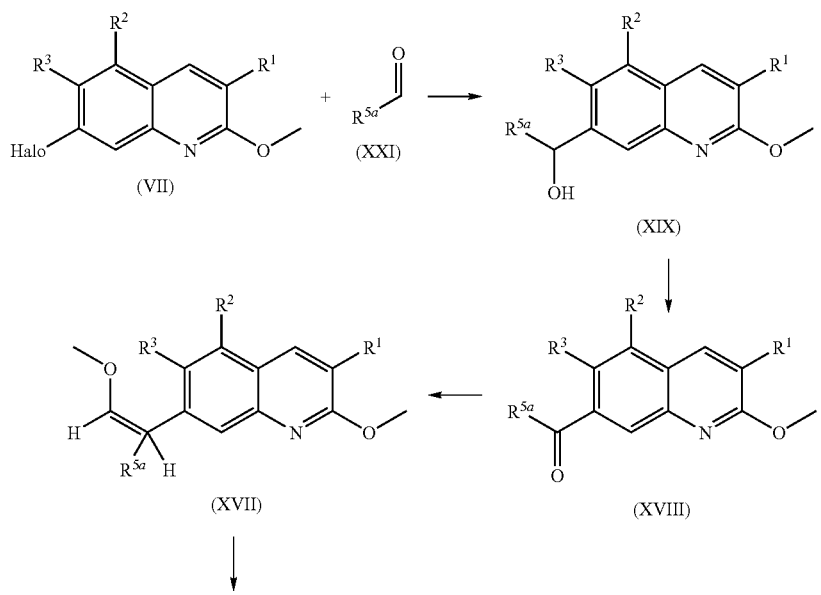

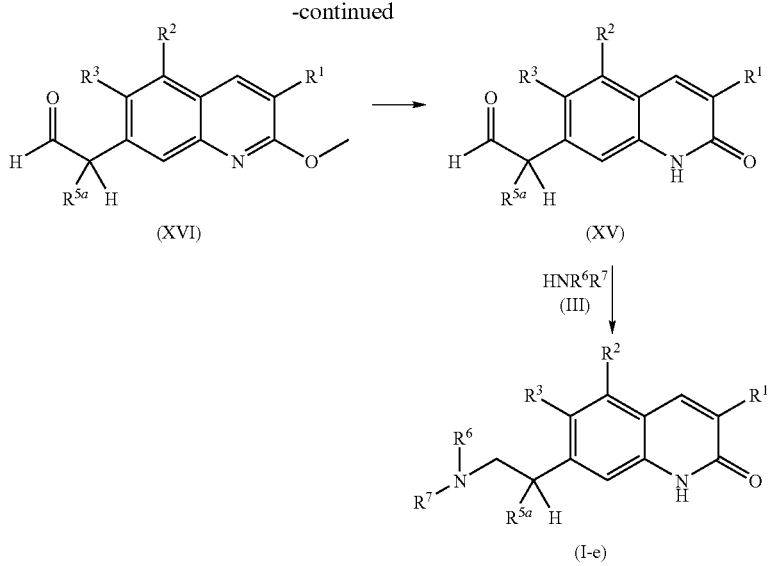

In the above scheme the individual stages may be carried out for example as follows:

a) a compound of formula (VII) above is reacted with an organolithium reagent such as e.g. n-butyllithium in an appropriate solvent such as tetrahydrofuran, and subsequently reacted with a compound of formula (XXI);

b) the resulting compound of formula (XIX) is oxidised in the presence of a suitable oxidant such as manganese dioxide in a suitable solvent such as dioxane or in the presence of potassium manganese tetraoxide in Tris[2-(2-ethoxyethoxy)-ethyl]amine, in a suitable solvent such as dichloromethane; Alternatively, compound of formula (XVIII) can be prepared by reacting a compound of formula (VII) above with an organolithium reagent such as e.g. n-butyllithium in an appropriate solvent such as tetrahydrofuran, and subsequently reacted with an appropriate Weinreb amide of formula $R^{5a}CON(Me)OMe$ or an acid chloride;

c) the resulting compound of formula (XVIII) is reacted with $(Ph)_3PCH_2OCH_3$ and potassium t-butoxide in an appropriate solvent such as tetrahydrofuran;

d) the resulting compound of formula (XVII) is treated with an acid such as sulphuric acid;

e) the resulting compound of formula (XVI) is hydrolysed for example with hydrochloric acid in an appropriate solvent such as dioxane;

f) the resulting compound of formula (XV) is reacted with an amine of formula (III) in the presence of $NaBH_3CN$ in an appropriate solvent such as methanol to form a compound of formula (I-e).

Compounds of formula (I) in which n is 1, one of $R^4$ and $R^5$ is hydroxymethyl and the other is hydrogen, represented by formula (I-f), can be prepared in accordance with reaction scheme F below:

Scheme F

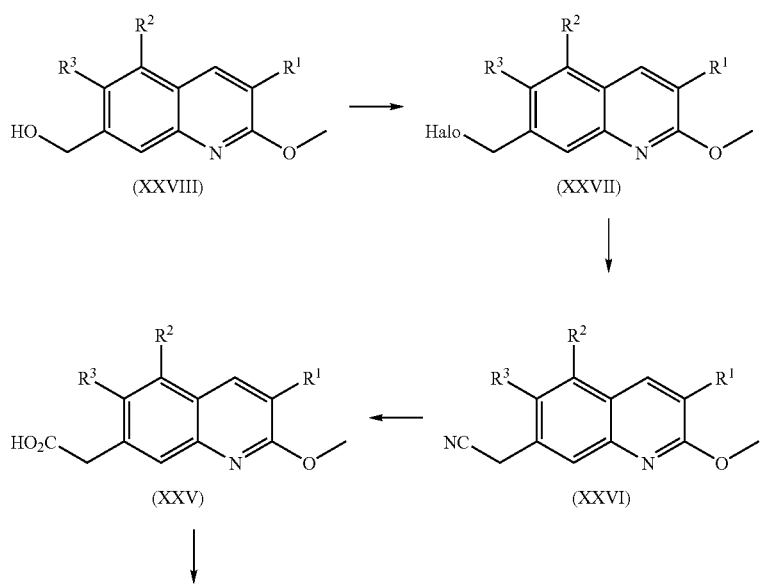

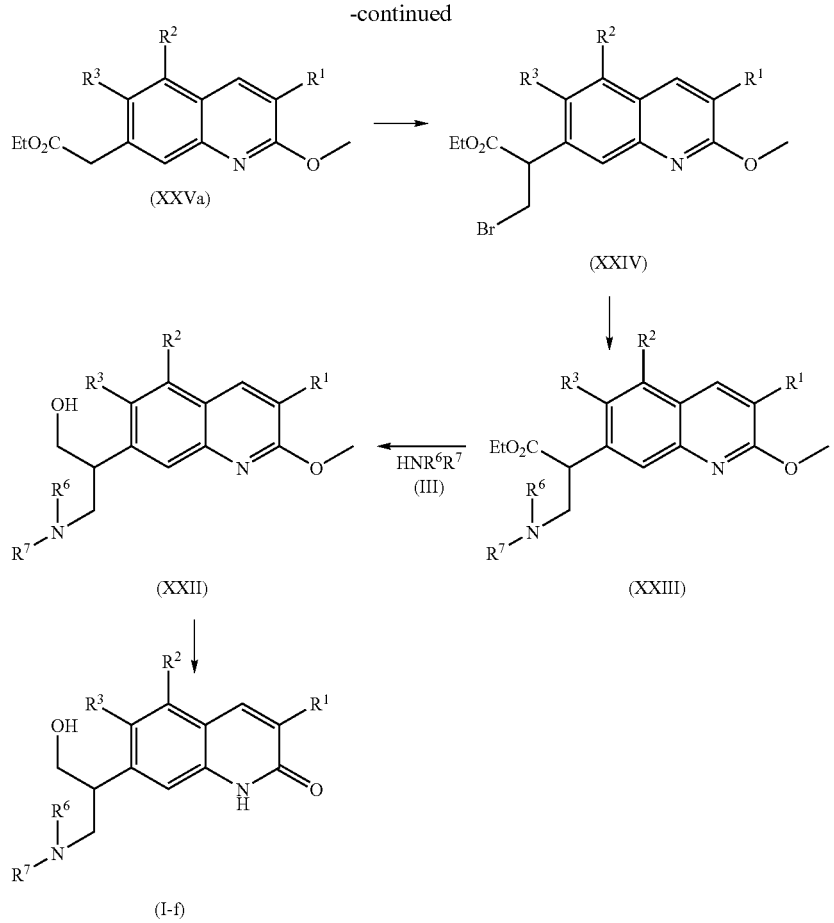

In the above scheme the individual stages may be carried out for example as follows:

a) the initial compound of formula (XXVIII) is halogenated for example by treatment with thionyl chloride or hydrobromic acid, to form a compound of formula (XXVII);

b) the resulting compound of formula (XXVII) is treated with for example a cyanide compound such as sodium cyanide in an appropriate solvent such as dimethylsulphoxide (DMSO) to form a compound of formula (XXVI);

c) the resulting compound of formula (XXVI) is subjected to an acidic treatment for example with sulphuric acid and aqueous acetic acid;

d) the resulting compound of formula (XXV) is esterified for example by initial treatment with thionyl chloride and then ethanol;

e) the resulting compound of formula (XXVa) is treated with potassium t-butoxide and then dibromomethane in an appropriate solvent such as tetrahydrofuran;

f) the resulting compound of formula (XXIV) is reacted with an amine of formula (III) under basic conditions for example in the presence of potassium carbonate in an appropriate solvent such as dimethylformamide;

g) the resulting compound of formula (XXIII) is reduced for example with lithium aluminium hydride;

h) the resulting compound of formula (XXII) is hydrolysed for example by treating with hydrochloric acid in an appropriate solvent such as dioxane to form a compound of formula (I-f).

Compounds of formula (I) in which n is 2 and $R^4$ and $R^5$ are each hydrogen, represented by formula (I-g), may be prepared in accordance with reaction scheme G below:

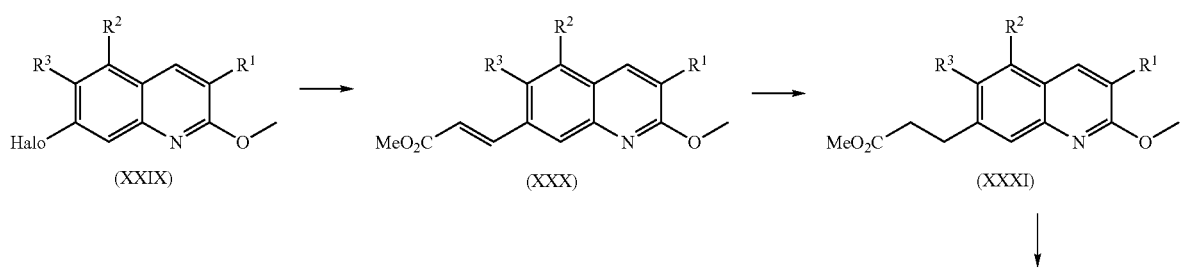

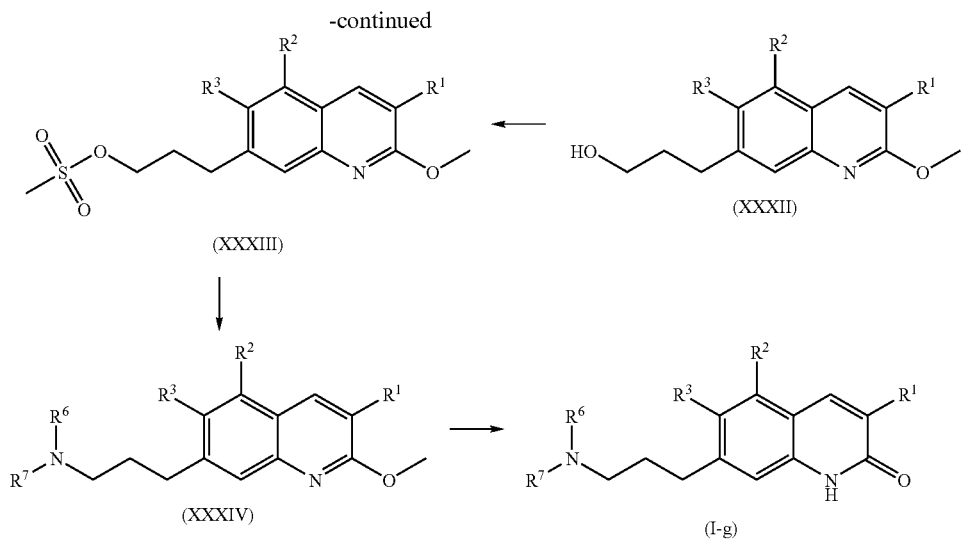

In the above scheme the individual stages may be carried out for example as follows:

a) a compound of formula (XXIX) is treated with methyl acrylate, Pd(dba)$_3$ and tri-toluoylphosphine in an appropriate solvent such as dimethylformamide;

b) the resulting compound of formula (XXX) is reduced for example by hydrogenation with palladium/carbon in an appropriate solvent such methanol;

c) the resulting compound of formula (XXXI) is reduced for example with lithium aluminium hydride in an appropriate solvent such as tetrahydrofuran;

d) the resulting compound of formula (XXXII) is sulphonylated for example with methanesulfonyl chloride in the presence of a base such as triethylamine in an appropriate solvent such as dichloromethane;

e) the resulting compound of formula (XXXIII) is reacted with an amine of formula (III) under basic conditions for example in the presence of potassium carbonate in an appropriate solvent such as acetonitrile;

f) the resulting compound of formula (XXXIV) is hydrolysed for example with hydrochloric acid in an appropriate solvent such as dioxane to form a compound of formula (I-g).

Other compounds of formula (I) in which n is 2 and $R^4$ is hydroxy, represented by formulae (I-h-1) and (I-h-2), may be prepared in accordance with reaction scheme H below:

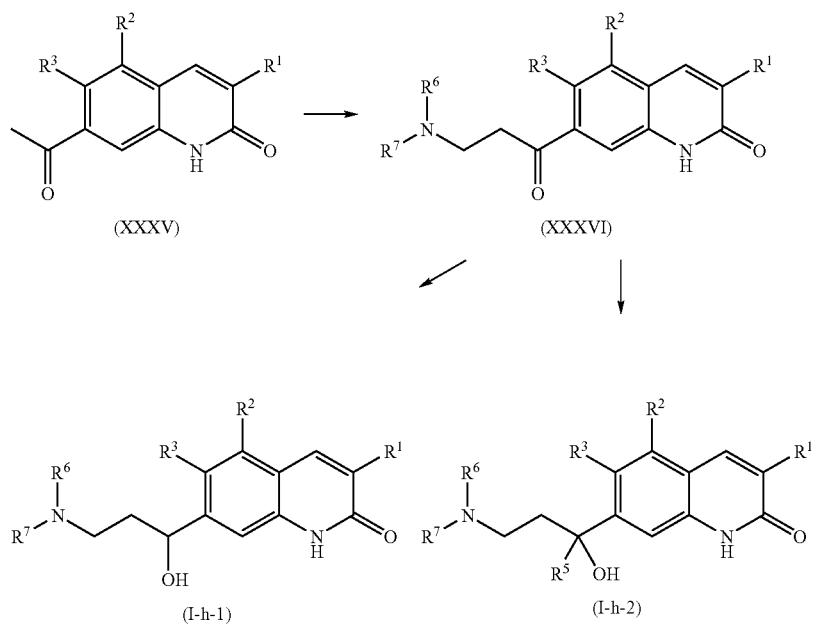

The compound of formula (XXXV), obtained for example by hydrolysis of a compound of formula (XVIII) above, can be subjected to a Mannich reaction with formaldehyde and an amine of formula (III) in the presence of an acid catalyst to form a compound of formula (XXXVI) which can then be:

a) reduced for example with sodium borohydride to form a compound of formula (I-h-1); or b) treated with an appropriate R$^5$MgX reagent in which X is a halogen atom for example a chlorine atom, reagent to form a compound of formula (I-h-2).

Compounds of formula (I) in which R$^4$ and R$^5$ together form a =O group, represented by formula (I-j) may be prepared by reaction of a compound of formula (XXXVII) with an amine of formula (III):

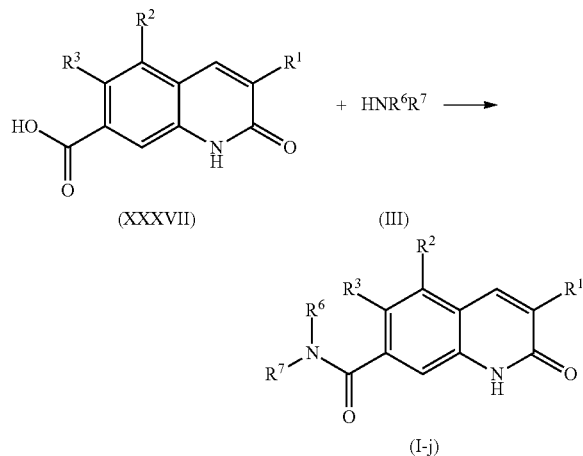

The reaction may be carried out using 1-ethyl-3-(3-dimethylaminopropyl)-carbodiimide (EDC) and 1-hydroxybenzotriazole (HOBT) in the presence of a base such as triethylamine and in an appropriate solvent such as tetrahydrofuran or dichloromethane.

The compounds of formula (I) or their intermediates may also be converted into each other via art-known reactions or functional group transformations. Some of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond; an iodo radical on a phenyl group may be converted in to an ester group by carbon monoxide insertion in the presence of a suitable palladium catalyst.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization, supercritical fluid chromatography or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

The present invention also relates to a compound of formula (I) as defined above for use as a medicine.

The compounds of the present invention have PARP inhibiting properties as can be seen from the experimental part hereinunder.

The term "PARP" is used herein to mean a protein having poly-ADP-ribosylation activity. Within the meaning of this term, PARP encompasses all proteins encoded by a parp gene, mutants thereof, and alternatively spliced proteins thereof. Additionally, as used herein, the term "PARP" includes PARP analogues, homologues and orthologues in other animals.

The term "PARP", includes but is not limited to PARP-1. Within the meaning of this term PARP-2, PARP-3, Vault-PARP (PARP-4), PARP-7 (TiPARP), PARP-8, PARP-9 (Bal), PARP-10, PARP-11, PARP-12, PARP-13, PARP-14, PARP-15, PARP-16, TANK-1, TANK-2, and TANK-3 may be encompassed.

The term "PARP inhibitor" or "inhibitor of PARP" is used to identify a compound, which is capable of interacting with a PARP or a TANK and inhibiting its activity, more particularly its enzymatic activity. Inhibiting PARP or TANK enzymatic activity means reducing the ability of a PARP or a TANK to produce poly(ADP-ribose) or to induce poly(ADP-ribosyl)ation of a substrate. Preferably, such inhibition is specific, i.e. the PARP inhibitor reduces the ability of a PARP to produce poly(ADP-ribose) or to induce poly(ADP-ribosyl)ation of a substrate at a concentration that is lower than the concentration of the inhibitor that is required to produce some other, unrelated biological effect.

The present invention also contemplates the use of compounds in the preparation of a medicament for the treatment of any of the diseases and disorders in an animal, particularly a human, described herein.

The present invention also contemplates the use of compounds of formula (I) for the manufacture of a medicament for the treatment of a PARP-mediated disorder.

This invention also provides a method for the treatment of a PARP-mediated disorder in a subject e.g. a mammal (and more particularly a human) by administering an effective amount of a compound of the present invention to the subject.

In view of their PARP binding properties the compounds of the present invention may be used as reference compounds or tracer compounds in which case one of the atoms of the molecule may be replaced with, for instance, a radioactive isotope. The compounds of formula (I) can also be used to detect or identify the PARP. For that purpose the compounds of formula (I) can be labeled. Said label can be selected from the group consisting of a radioisotope, spin label, antigen label, enzyme label fluorescent group or a chemiluminiscent group.

The present invention further includes pharmaceutical compositions comprising a therapeutically effective amount of at least one compound according to the invention together with a pharmaceutically acceptable carrier.

To prepare the pharmaceutical compositions of this invention, an effective amount of a particular compound according to the invention as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars; kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage.

Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compounds of the present invention can treat or prevent tissue damage resulting from cell damage or death due to necrosis or apoptosis; can ameliorate neural or cardiovascular tissue damage, including that following focal ischemia, myocardial infarction, and reperfusion injury; can treat various diseases and conditions caused or exacerbated by PARP activity; can extend or increase the lifespan or proliferative capacity of cells; can alter the gene expression of senescent cells; can radiosensitize and/or chemosensitize cells. Generally, inhibition of PARP activity spares the cells from energy loss, preventing, in the case of neural cells, irreversible depolarization of the neurons, and thus, provides neuroprotection.

For the foregoing reasons, the present invention further relates to a method of administering a therapeutically effective amount of the above-identified compounds in an amount sufficient to inhibit PARP activity, to treat or prevent tissue damage resulting from cell damage or death due to necrosis or apoptosis, to effect a neuronal activity not mediated by NMDA toxicity, to effect a neuronal activity mediated by NMDA toxicity, to treat neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related muscular degeneration, AIDS and other immune senescence diseases, inflammation, gout, arthritis, atherosclerosis, cachexia, cancer, degenerative diseases of skeletal muscle involving replicative senescence, diabetes, head trauma, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging, to extend the lifespan and proliferative capacity of cells; to alter gene expression of senescent cells; chemosensitize and/or radiosensitize (hypoxic) tumour cells. The present invention also relates to treating diseases and conditions in an animal which comprises administering to said animal a therapeutically effective amount of the above-identified compounds.

In particular, the present invention relates to a method of treating, preventing or inhibiting a neurological disorder in an animal, which comprises administering to said animal a therapeutically effective amount of the above-identified compounds. The neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration.

The present invention also contemplates the use of compounds of formula (I) for inhibiting PARP activity, for treating, preventing or inhibiting tissue damage resulting from cell damage or death due to necrosis or apoptosis, for treating, preventing or inhibiting a neurological disorder in an animal.

The term "treatment" as used herein covers any treatment of a disease and/or condition in an animal, particularly a human, and includes: (i) preventing a disease and/or condition from occurring in a subject which may be predisposed to the disease and/or condition but has not yet been diagnosed as having it; (ii) inhibiting the disease and/or condition, i.e., arresting its development; (iii) relieving the disease and/or condition, i.e., causing regression of the disease and/or condition.

As described above PARP inhibitors have been shown to inhibit angiogenesis, which has been implicated in tumour growth, and the present invention therefore includes the use of compounds according to the invention for treating cancers including the specific cancers described herein. The compounds according to the invention are particularly useful for the treatment of cancers with inherited defects in one of the BRCA1 or BRCA2 alleles.

The present invention therefore relates to a compound according to the invention for inhibiting the growth of tumour cells.

The present invention also relates to the use of compounds according to the invention for the preparation of a medicament for inhibiting the growth of tumour cells.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the inhibition of tumour growth both directly by causing growth arrest, terminal differentiation and/or apoptosis of cancer cells, and indirectly, by inhibiting neovascularization of tumours.

This invention also provides a method for inhibiting tumour growth by administering an effective amount of a compound of the present invention, to a subject, e.g. a mammal (and more particularly a human) in need of such treatment.

The methods of the invention are also useful for chemosensitizing and/or radiosensitizing tumour cells in cancers.

As another aspect of the present invention, a combination of a PARP inhibitor of the present invention, as a chemosensitizing agent or radiosensitizing agent, with another anticancer agent is envisaged, especially for use as a medicine, more specifically in the treatment of cancer or related diseases.

The term "radiosensitizing agent", as used herein, in relation to the compounds according to the invention refers to the use of such compounds to increase the sensitivity of the cells to ionizing radiation and/or to promote the treatment of diseases which are treatable with ionizing radiation. Diseases which are treatable with ionizing radiation include neoplastic diseases, benign and malignant tumours, and cancerous cells. Ionizing radiation treatment of other diseases not listed herein are also contemplated by the present invention.

The term "chemosensitizing agent", as used herein, in relation to the compounds according to the invention refers to the use of such compounds to increase the sensitivity of cells to chemotherapy and/or promote the treatment of diseases which are treatable with chemotherapeutics. Diseases which are treatable with chemotherapy include neoplastic diseases, benign and malignant tumours and cancerous cells. Chemotherapy treatment of other diseases not listed herein are also contemplated by the present invention.

Examples of tumours which may be inhibited include, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), prostate cancer including the advanced disease, hematopoietic tumours of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumours of mesenchymal origin (e.g. fibrosarcomas and rhabdomyosarcomas), melanomas, teratocarcinomas, neuroblastomas, gliomas, benign tumour of the skin (e.g. keratoacanthomas), breast carcinoma (e.g. advanced breast cancer), kidney carcinoma, ovary carcinoma, bladder carcinoma and epidermal carcinoma.

For the treatment of the above conditions, the compounds of the invention are employed in combination with one or more other medicinal agents, more particularly, with other anti-cancer agents. Examples of anti-cancer agents are:

- platinum coordination compounds for example cisplatin, carboplatin or oxalyplatin;
- taxane compounds for example paclitaxel or docetaxel;
- topoisomerase I inhibitors such as *camptothecin* compounds for example irinotecan or topotecan;
- topoisomerase II inhibitors such as anti-tumour podophyllotoxin derivatives for example etoposide or teniposide;
- anti-tumour vinca alkaloids for example vinblastine, vincristine or vinorelbine;
- anti-tumour nucleoside derivatives for example 5-fluorouracil, gemcitabine or capecitabine;
- alkylating agents such as nitrogen mustard or nitrosourea for example cyclophosphamide, chlorambucil, carmustine or lomustine;
- anti-tumour anthracycline derivatives for example daunorubicin, doxorubicin, idarubicin or mitoxantrone;
- HER2 antibodies for example trastuzumab;
- estrogen receptor antagonists or selective estrogen receptor modulators for example tamoxifen, toremifene, droloxifene, faslodex or raloxifene;
- aromatase inhibitors such as exemestane, anastrozole, letrazole and vorozole;
- differentiating agents such as retinoids, vitamin D and retinoic acid metabolism blocking agents (RAMBA) for example accutane;
- DNA methyl transferase inhibitors for example azacytidine and decitabine;
- kinase inhibitors for example flavoperidol, imatinib mesylate or gefitinib;
- farnesyltransferase inhibitors for example tipifarnib;
- Histone Deacetylase (HDAC) inhibitors for example sodium butyrate, suberoylanilide hydroxamide acid (SAHA), R306465, JNJ-26481585 and trichostatin A;
- Inhibitors of the ubiquitin-proteasome pathway for example PS-341, MLN 0.41 or bortezomib;
- Yondelis;
- Telomerase inhibitors for example telomestatin;
- Matrix metalloproteinase inhibitors for example batimastat, marimastat, prinostat and metastat.

The term "platinum coordination compound" is used herein to denote any tumour cell growth inhibiting platinum coordination compound which provides platinum in the form of an ion.

The term "taxane compounds" indicates a class of compounds having the taxane ring system and related to or derived from extracts from certain species of yew (Taxus) trees.

The term "topisomerase inhibitors" is used to indicate enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme of approximately 100,000 molecular weight. The enzyme binds to DNA and introduces a transient single-strand break, unwinds the double helix (or allows it to unwind) and subsequently reseals the break before dissociating from the DNA strand. Topisomerase II has a similar mechanism of action which involves the induction of DNA strand breaks or the formation of free radicals.

The term "*camptothecin* compounds" is used to indicate compounds that are related to or derived from the parent *camptothecin* compound which is a water-insoluble alkaloid derived from the Chinese tree *Camptothecin acuminata* and the Indian tree *Nothapodytes foetida*.

The term "podophyllotoxin compounds" is used to indicate compounds that are related to or derived from the parent podophyllotoxin, which is extracted from the mandrake plant.

The term "anti-tumour vinca alkaloids" is used to indicate compounds that are related to or derived from extracts of the periwinkle plant (*Vinca rosea*).

The term "alkylating agents" encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation in particular DNA synthesis and cell division. The capacity of alkylating agents to interfere with DNA function and integrity in rapidly proliferating tissues provides the basis for their therapeutic applications and for many of their toxic properties.

The term "anti-tumour anthracycline derivatives" comprise antibiotics obtained from the fungus Strep. peuticus var. caesius and their derivatives, characterised by having a tetracycline ring structure with an unusual sugar, daunosamine, attached by a glycosidic linkage.

Amplification of the human epidermal growth factor receptor 2 protein (HER 2) in primary breast carcinomas has been shown to correlate with a poor clinical prognosis for certain patients. Trastuzumab is a highly purified recombinant DNA-derived humanized monoclonal IgG1 kappa antibody that binds with high affinity and specificity to the extracellular domain of the HER2 receptor.

Many breast cancers have estrogen receptors and growth of these tumours can be stimulated by estrogen. The terms "estrogen receptor antagonists" and "selective estrogen receptor modulators" are used to indicate competitive inhibitors of estradiol binding to the estrogen receptor (ER). Selective estrogen receptor modulators, when bound to the ER, induces a change in the three-dimensional shape of the receptor, modulating its binding to the estrogen responsive element (ERE) on DNA.

In postmenopausal women, the principal source of circulating estrogen is from conversion of adrenal and ovarian androgens (androstenedione and testosterone) to estrogens (estrone and estradiol) by the aromatase enzyme in peripheral tissues. Estrogen deprivation through aromatase inhibition or inactivation is an effective and selective treatment for some postmenopausal patients with hormone-dependent breast cancer.

The term "antiestrogen agent" is used herein to include not only estrogen receptor antagonists and selective estrogen receptor modulators but also aromatase inhibitors as discussed above.

The term "differentiating agents" encompass compounds that can, in various ways, inhibit cell proliferation and induce differentiation. Vitamin D and retinoids are known to play a major role in regulating growth and differentiation of a wide variety of normal and malignant cell types. Retinoic acid metabolism blocking agents (RAMBA's) increase the levels of endogenous retinoic acids by inhibiting the cytochrome P450-mediated catabolism of retinoic acids.

DNA methylation changes are among the most common abnormalities in human neoplasia. Hypermethylation within the promotors of selected genes is usually associated with inactivation of the involved genes. The term "DNA methyl transferase inhibitors" is used to indicate compounds that act through pharmacological inhibition of DNA methyl transferase and reactivation of tumour suppressor gene expression.

The term "kinase inhibitors" comprises potent inhibitors of kinases that are involved in cell cycle progression and programmed cell death (apoptosis).

The term "farnesyltransferase inhibitors" is used to indicate compounds that were designed to prevent farnesylation of Ras and other intracellular proteins. They have been shown to have effect on malignant cell proliferation and survival.

The term "histone deacetylase inhibitor" or "inhibitor of histone deacetylase" is used to identify a compound, which is capable of interacting with a histone deacetylase and inhibiting its activity, more particularly its enzymatic activity. Inhibiting histone deacetylase enzymatic activity means reducing the ability of a histone deacetylase to remove an acetyl group from a histone.

The term "other inhibitors of the ubiquitin-proteasome pathway" is used to indentify compounds that inhibit the targeted destruction of cellular proteins in the proteasome, including cell cycle regulatory proteins.

The term "telomerase inhibitor" refers to compounds which target, decrease or inhibit the activity of telomerase, especially compounds which inhibit the telomerase receptor.

The term "matrix metalloproteinase inhibitor" includes but is not limited to, collagen peptidomimetic and non-peptidomimetic inhibitors.

Radiosensitizers are known to increase the sensitivity of cancerous cells to the toxic effects of ionizing radiation. Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogs of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other disease. Examples of additional therapeutic agents that may be used in conjunction with radiosensitizers include, but are not limited to: 5-fluorouracil, leucovorin, 5'-amino-5'-deoxythymidine, oxygen, carbogen, red cell transfusions, perfluorocarbons (e.g., Fluosol 10 DA), 2,3-DPG, BW12C, calcium channel blockers, pentoxyfylline, antiangiogenesis compounds, hydralazine, and LBSO. Examples of chemotherapeutic agents that may be used in conjunction with radiosensitizers include, but are not limited to: adriamycin, *camptothecin*, carboplatin, cisplatin, daunorubicin, docetaxel, doxorubicin, interferon (alpha, beta, gamma), interleukin 2, irinotecan, paclitaxel, topotecan, and therapeutically effective analogs and derivatives of the same.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease.

The present invention also relates to a combination according to the invention for use in medical therapy for example for inhibiting the growth of tumour cells.

The present invention also relates to a combination according to the invention for inhibiting the growth of tumour cells.

The present invention also relates to a method of inhibiting the growth of tumour cells in a human subject which comprises administering to the subject an effective amount of a combination according to the invention.

This invention further provides a method for inhibiting the abnormal growth of cells, including transformed cells, by administering an effective amount of a combination according to the invention.

The other medicinal agent and PARP inhibitor may be administered simultaneously (e.g. in separate or unitary compositions) or sequentially in either order. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and PARP inhibitor being administered, their route of administration, the particular tumour being treated and the particular host being treated. The optimum method and order of administration and the dosage amounts and regime can be readily determined by those skilled in the art using conventional methods and in view of the information set out herein.

Those skilled in the art could easily determine the effective amount from the test results presented hereinafter. In general it is contemplated that an effective amount would be from 0.001 mg/kg to 100 mg/kg body weight, and in particular from 0.005 mg/kg to 10 mg/kg body weight. It may be appropriate to administer the required dose as two, three, four or more sub-doses at appropriate intervals throughout the day. Said sub-doses may be formulated as unit dosage forms, for example, containing 0.05 to 500 mg, and in particular 0.1 mg to 200 mg of active ingredient per unit dosage form.

The following examples illustrate the present invention.

EXPERIMENTAL PART

Hereinafter, "DMF" is defined as N,N-dimethylformamide, "DCM" is defined as dichloromethane, "DIPE" is defined as diisopropyl ether, "DIPEA" is defined as N-ethyl-N-(1-methylethyl)-2-propanamine, "EDC" is defined as 1,2-dichloro ethane, "EtOAc" is defined as ethyl acetate, "EtOH" is defined as ethanol, "HOBT" is defined as 1-hydroxy-1H-benzotriazole, "MeOH" is defined as methanol, "nBuLi" is defined as butyl-lithium and "THF" is defined as tetrahydrofuran.

A. Preparation of the Intermediate Compounds

Example A1 a) Preparation of Intermediate 1

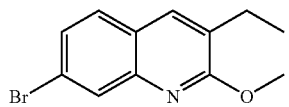

CH$_3$Ona/MeOH 30% (0.3 mol) was added dropwise at room temperature to a solution of 7-bromo-2-chloro-3-ethyl-quinoline (0.0739 mol) in MeOH (150 ml). The mixture was stirred and refluxed for 7 hours and poured out into ice water. The precipitate was filtered, washed with water and dried, yielding 19.5 g of intermediate 1.

b) Preparation of Intermediate 2

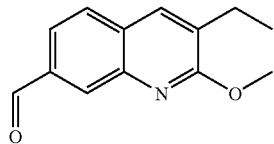 [SMILES: CCc1cc2ccc(C=O)cc2nc1OC]

nBuLi 1.6M (0.0225 mol) was added dropwise at −78° C. to a solution of intermediate 1 (0.0188 mol) in THF (100 ml). The mixture was stirred at −78° C. for 20 minutes. A solution of 1-piperidinecarboxaldehyde (0.0282 mol) in THF (3 ml) was added dropwise. The mixture was stirred at −78° C. for 1 hour, poured out on ice and extracted with EtOAc twice. The organic layer was washed with saturated NaCl, dried (MgSO$_4$), filtered and the solvent was evaporated. The residue was taken up in DIPE. The precipitate was filtered off and dried, yielding 2.5 g of intermediate 2. The mother layer was evaporated and the residue (2 g) was purified by column chromatography over silica gel (15-40 μm) (eluent: cyclohexane/AcOEt 90/10). The pure fractions were collected and the solvent was evaporated, yielding 0.64 g of intermediate 2.

c) Preparation of Intermediate 3

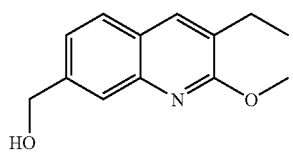 [SMILES: CCc1cc2ccc(CO)cc2nc1OC]

Sodium tetrahydroborate (0.0011 mol) was added at 5° C. to a solution of intermediate 2 (0.0009 mol) in MeOH (10 ml). The mixture was stirred at room temperature for 1 hour, poured out on ice. The precipitate was filtered, washed with water, then diluted in DCM. The organic layer was separated, dried (MgSO$_4$), filtered and the solvent was evaporated, yielding 0.17 g (84%) of intermediate 3, melting point: 72° C.

d) Preparation of Intermediate 4

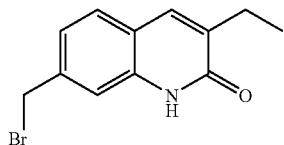

A mixture of intermediate 3 (0.0007 mol) in hydrobromic acid 48% (2 ml) was stirred and refluxed for 1 hour, then brought to room temperature. Ice and water were added. The precipitate was filtered, washed with water, then with DIPE and dried, yielding 0.18 g (90%) of intermediate 4.

Example A2

Preparation of Intermediate 5

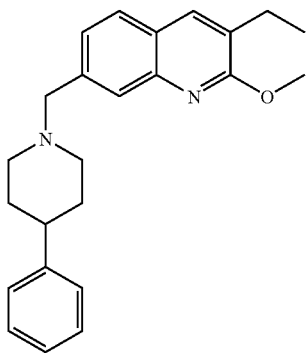 [SMILES: CCc1cc2ccc(CN3CCC(c4ccccc4)CC3)cc2nc1OC]

Tris (☐cetate-α-O)hydroborate (1-), sodium (0.0034 mol) then acetic acid (0.0023 mol) were added at room temperature to a solution of intermediate 2 (0.0023 mol) and 4-phenyl-piperidine (0.0027 mol) in THF (20 ml). The mixture was stirred at room temperature for 24 hours. Tris (☐cetate-α-O) hydroborate (1-), sodium (0.3 eq) was added. The mixture was stirred at room temperature for 24 hours, poured out into ice water, neutralized with NaHCO$_3$ and extracted twice with EtOAc. The organic layer was washed with saturated NaCl, dried (MgSO$_4$), filtered and the solvent was evaporated. The residue (0.95 g) was purified by column chromatography over silica gel (3-5 μm) (eluent: DCM/MeOH 99/1 to 95/5). The pure fractions were collected and the solvent was evaporated, yielding 0.44 g (44%) of intermediate 5.

Example A3 a) Preparation of Intermediate 6

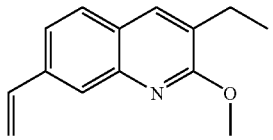 [SMILES: C=Cc1ccc2cc(CC)c(OC)nc2c1]

A mixture of intermediate 1 (0.0075 mol), tributylethenyl-stannane (0.009 mol) and palladiumbis(triphenylphosphine) dichloride (0.0007 mol) was stirred and refluxed for 24 hours. The organic layer was washed with water, dried (MgSO$_4$), filtered, and the solvent was evaporated. The residue (5 g) was purified by column chromatography over silica gel (15-40 μm) (eluent: cyclohexane/DCM 60/40). The pure fractions were collected and the solvent was evaporated, yielding 1.6 g of intermediate 6. This fraction was used directly in the next reaction step.

b) Preparation of Intermediate 7

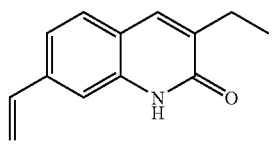

A mixture of intermediate 6 (0.001 mol) in hydrochloric acid 3N (5 ml) and THF (1 ml) was stirred and refluxed for 15 hours. Water was added. The mixture was made alkaline with sodium carbonate. The precipitate was filtered, washed with water and dried, yielding 0.07 g (34%) of intermediate 7.

c) Preparation of Intermediate 8

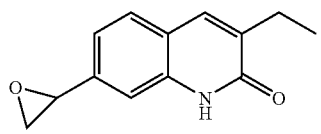 [SMILES: CCc1cc2ccc(C3CO3)cc2[nH]c1=O]

3-chloro-benzenecarboperoxoic acid (0.0003 mol) was added portionwise at 5° C. to a solution of intermediate 7 (0.0003 mol) in DCM (10 ml). The mixture was stirred at room temperature for 15 hours. 3-chloro-benzenecarboper-oxoic acid (0.2 eq) was added. The mixture was stirred at room temperature for 15 hours. Water was added. The mixture was made alkaline with sodium carbonate. The organic layer was separated, dried (MgSO$_4$), filtered and the solvent was evaporated, yielding 0.078 g of intermediate 8.

Example A4 a) Preparation of Intermediate 9

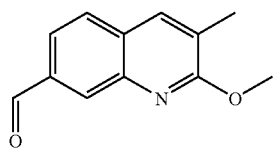

nBuLi 1.6M (0.018 mol) was added dropwise at −78° C. to a solution of 7-bromo-2-methyloxy-3-methyl-quinoline (0.015 mol) in THF (75 ml). The mixture was stirred at −78° C. for 20 minutes. A solution of 1-piperidinecarboxaldehyde (0.022 mol) in THF (2.5 ml) was added dropwise. The mixture was stirred at −78° C. for 1 hour, poured out on ice and extracted with EtOAc twice. The organic layer was washed with saturated NaCl, dried (MgSO$_4$), filtered and the solvent was evaporated. The residue was crystallized from DIPE. The precipitate was filtered off and dried, yielding 1.7 g (50%) of intermediate 9.

b) Preparation of Intermediate 10

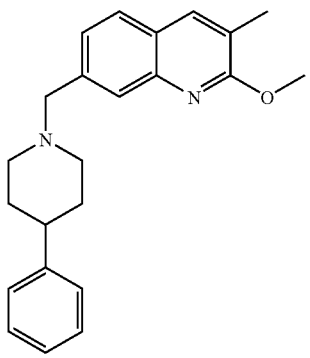 [SMILES: COc1nc2cc(CN3CCC(c4ccccc4)CC3)ccc2cc1C]

Tris(□cetate-α-O)hydroborate (1-), sodium (0.0054 mol) then acetic acid (0.003 mol) were added at room temperature to a mixture of intermediate 9 (0.003 mol) and 4-phenyl-piperidine (0.0042 mol) in THF (25 ml). The mixture was stirred at room temperature for 15 hours, poured out on ice, neutralized with NaHCO$_3$ and extracted twice with EtOAc. The organic layer was washed with saturated NaCl, dried (MgSO$_4$), filtered and the solvent was evaporated. The residue (1 g) was purified by column chromatography over silica gel (15-40 μm) (eluent: cyclohexane/EtOAc 80/20). The pure fractions were collected and the solvent was evaporated, yielding 0.76 g (73%) of intermediate 10, melting point 100° C.

Example A5 a) Preparation of Intermediate 11

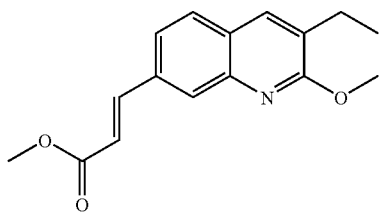 [SMILES: CCc1cc2ccc(/C=C/C(=O)OC)cc2nc1OC]

Tris[μ-[(1,2-η:4,5-η)-(1E,4E)-1,5-diphenyl-1,4-penta-dien-3-one]]di-palladium (0.0002 mol) was added to a mixture of intermediate 1 (0.0037 mol), 2-propenoic acid, methyl ester (0.0225 mol), tris(2-methylphenyl)-phosphine (0.0006 mol) and DIPEA (0.0094 mol) in DMF (5 ml). The mixture was stirred at 100° C. for 24 hours, then evaporated till dryness. The residue was taken up in water. The mixture was extracted twice with diethyl ether. The organic layer was washed with water several times, dried (MgSO$_4$), filtered and the solvent was evaporated. The residue (1.5 g) was purified by column chromatography over silica gel (15-40 μm) (eluent: cyclohexane/EtOAc 90/10). The pure fractions were collected and the solvent was evaporated, yielding 0.8 g (80%) of intermediate 11.

b) Preparation of Intermediate 12

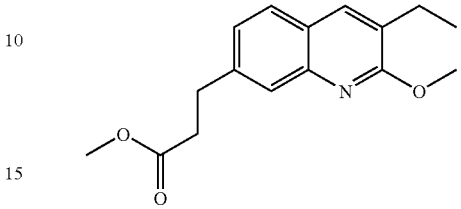

A suspension of intermediate 11 (0.0007 mol) and Pd/C 10% (0.02 g) in MeOH (20 ml) was hydrogenated at room temperature for 15 hours under a 3 bar pressure, then filtered. The filtrate was evaporated, yielding 0.2 g of intermediate 12.

c) Preparation of Intermediate 13

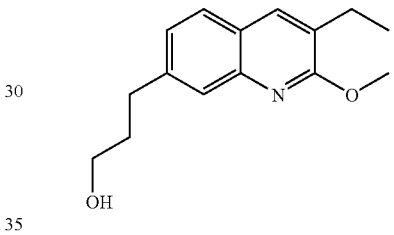

Lithium tetrahydroaluminate (0.0008 mol) was added at 5° C. to a solution of intermediate 12 (0.0007 mol) in THF (7 ml). The mixture was stirred at 5° C. for 30 minutes, poured out into EtOAc, then with water and filtered over celite. Celite was washed with EtOAc. The organic layer was separated, dried (MgSO$_4$), filtered and the solvent was evaporated, yielding 0.19 g of intermediate 13.

d) Preparation of Intermediate 14

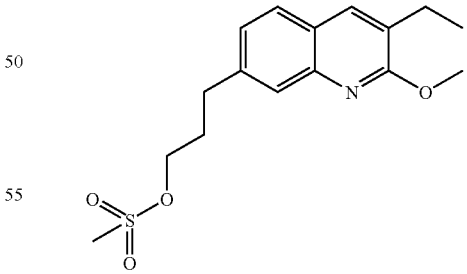

Methanesulfonyl chloride (0.0009 mol) was added dropwise at 5° C. to a mixture of intermediate 13 (0.0007 mol) and triethylamine (0.0014 mol) in DCM (10 ml). The mixture was stirred at room temperature for 2 hours, then stirred for 15 hours and cooled to 5° C. Triethylamine (2 eq) then methanesulfonyl chloride (1.3 eq) were added. The mixture was stirred at room temperature for 15 hours. The organic layer was washed with water, dried (MgSO$_4$), filtered and the solvent was evaporated, yielding 0.26 g of intermediate 14. This product was used directly in the next reaction step.

e) Preparation of Intermediate 15

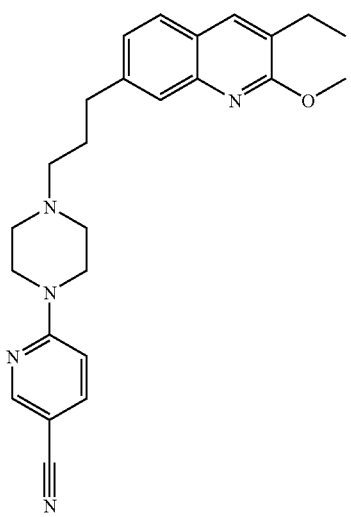 [SMILES: CCc1cc2ccc(CCCN3CCN(c4ccc(C#N)cn4)CC3)cc2nc1OC]

A mixture of intermediate 14 (0.0007 mol), 6-(1-piperazinyl)-3-pyridinecarbonitrile (0.0087 mol) and DIPEA (0.0022 mol) in acetonitrile (15 ml) was stirred at 80° C. for 48 hours. Water was added. The mixture was extracted with DCM. The organic layer was separated, dried (MgSO$_4$), filtered and the solvent was evaporated. The residue (0.41 g) was purified by column chromatography over Sunfire (5 μm) (eluent: DCM/MeOH 100/0 to 97.5/2.5). The pure fractions were collected and the solvent was evaporated, yielding 0.16 g (53%) of intermediate 15.

Example A6 a) Preparation of Intermediate 16

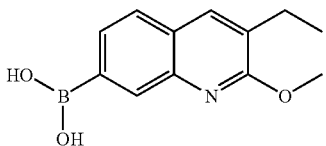

nBuLi 1.6M (0.018 mol) was added dropwise at −78° C. to a solution of intermediate 1 (0.015 mol) in THF (25 ml) under N$_2$ flow. The mixture was stirred at −78° C. for 20 minutes. Trimethyl borate (0.045 mol) was added dropwise. The mixture was stirred at −78° C. for 1 hour, then stirred at room temperature for 1 hour. Hydrochloric acid 3N was added at 5° C. till Ph was set to 4-5. The mixture was stirred for 15 minutes, then extracted with EtOAc twice. The organic layer was washed with saturated NaCl, dried (MgSO$_4$), filtered and the solvent was evaporated, yielding 2.2 g (62%) of intermediate 16.

b) Preparation of Intermediate 17

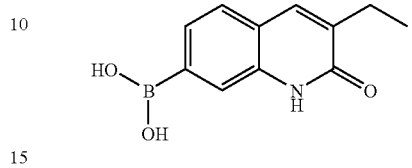

A mixture of intermediate 16 (0.0021 mol) in hydrochloric acid 3N (5 ml) and THF (5 ml) was stirred at 60° C. for 24 hours. Water was added. Sodium carbonate was added. The precipitate was filtered, washed with water and dried, yielding 0.42 g (91%) of intermediate 17.

Example A7 a) Preparation of Intermediate 18

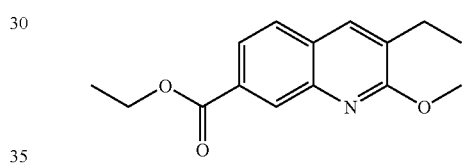

A mixture of intermediate 1 (0.0038 mol), acetic acid, palladium(2+) salt (0.0003 mol), triphenylphosphine (0.0057 mol), EtOH (10 ml) and potassium carbonate (0.0076 mol) in DMF (10 ml) was hydrogenated at 90° C. overnight under a 5 bar pressure of CO, then cooled to room temperature, poured out into water and extracted with DCM. The organic layer was washed with water, dried (MgSO$_4$), filtered and the solvent was evaporated. The residue (2 g) was purified by column chromatography over silica gel (15-40 μm) (eluent: cyclohexane/EtOAc 98.5/1.5). The pure fractions were collected and the solvent was evaporated, yielding 0.28 g (29%) of intermediate 18.

b) Preparation of Intermediate 19

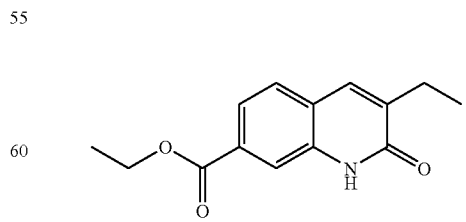

A mixture of intermediate 18 (0.001 mol) in hydrochloric acid 6N (3 ml) and dioxane (3 ml) was stirred at 160° C. overnight, then cooled to room temperature and basified with potassium carbonate 10%. The precipitate was filtered, washed with diethyl ether and dried, yielding 0.21 g (80%) of intermediate 19.

c) Preparation of Intermediate 20

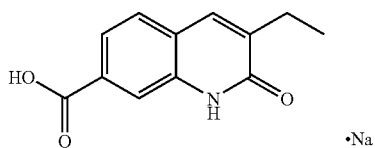

A mixture of intermediate 19 (0.0008 mol) and sodium hydroxide (0.0016 mol) in EtOH (10 ml) was stirred at 80° C. overnight, then cooled to room temperature. The precipitate was filtered, washed with diethyl ether and dried, yielding 0.15 g (75%) of intermediate 20.

Example A8 a) Preparation of Intermediate 21

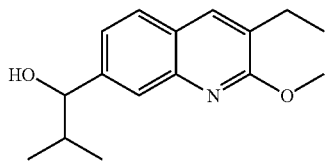

2-Propylmagnesium chloride (0.015 mol) was added dropwise at −40° C. to a solution of intermediate 2 (0.01 mol) in THF (110 ml) under $N_2$ flow. The mixture was stirred at −40° C. for 20 minutes, then brought to room temperature, stirred for 15 hours and poured out into ice water. $NH_4Cl$ was added. The mixture was extracted with EtOAc twice. The organic layer was washed with saturated NaCl, dried ($MgSO_4$), filtered and the solvent was evaporated. The residue (2.4 g) was purified by column chromatography over silica gel (15-40 μm) (eluent: cyclohexane/EtOAc 80/20 to 0/100). The pure fractions were collected and the solvent was evaporated. Yielding: 0.58 g (22%) of intermediate 21.

b) Preparation of Intermediate 22

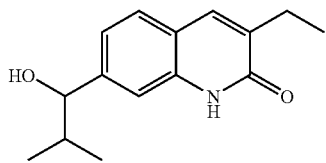

A mixture of intermediate 21 (0.0022 mol) in hydrochloric acid 3N (10 ml) and dioxane (10 ml) was stirred at 60° C. for 6 hours. Water was added. The mixture was basified with sodium carbonate. The precipitate was filtered, washed with water, then with DIPE and dried, yielding 0.35 g (65%) of intermediate 22, melting point 214° C.

c) Preparation of Intermediate 23

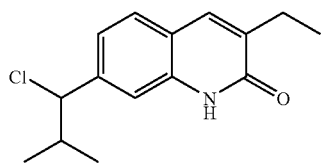 [SMILES: CCc1cc2ccc(C(Cl)C(C)C)cc2[nH]c1=O]

Thionyl chloride (0.3 ml) was added at 5° C. to a solution of intermediate 22 (0.0012 mol) in DCM (30 ml). The mixture was stirred at room temperature for 15 hours, then evaporated till dryness. The residue was taken up in DCM. The mixture was evaporated till dryness, yielding intermediate 23. This product was used directly in the next reaction step.

Example A9 a) Preparation of Intermediate 24

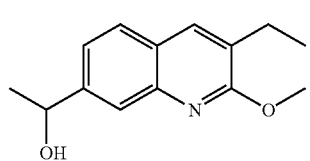 [SMILES: CCc1cc2ccc(C(C)O)cc2nc1OC]

nBuLi 1.6M (0.018 mol) was added dropwise at −78° C. to a solution of intermediate 1 (0.015 mol) in THF (80 ml) under $N_2$ flow. The mixture was stirred at −78° C. for 20 minutes. Acetaldehyde (0.03 mol) was added. The mixture was stirred at −78° C. for 1 hour, then brought to room temperature, poured out into ice water and extracted with EtOAc. The organic layer was washed with saturated NaCl, dried ($MgSO_4$), filtered and the solvent was evaporated. The residue (4.1 g) was purified by column chromatography over silica gel (15-40 μm) (eluent: cyclohexane/EtOAc 80/20). The pure fractions were collected and the solvent was evaporated, yielding 1.752 (50%) of intermediate 24.

b) Preparation of Intermediate 25

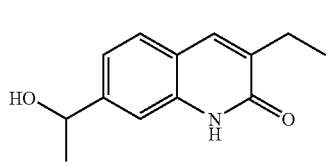

A mixture of intermediate 24 (0.0021 mol) in hydrochloric acid 3N (5 ml) and dioxane (5 ml) was stirred at 60° C. for 24 hours, then brought to room temperature. Ice and water were added. The mixture was basified with potassium carbonate.

The precipitate was filtered, washed with water, then with DIPE and dried, yielding: 0.27 g of intermediate 25.

c) Preparation of Intermediate 26

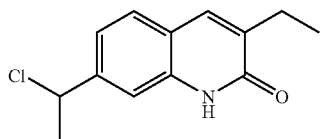 [SMILES: CCc1cc2ccc(C(C)Cl)cc2[nH]c1=O]

Thionyl chloride (2.5 ml) was added at 5° C. to a solution of intermediate 25 (0.0012 mol) in DCM (25 ml). The mixture was stirred at room temperature for 15 hours, then evaporated till dryness. The residue was taken up in DCM. The mixture was evaporated till dryness, yielding intermediate 26.

Example A10

Preparation of Intermediate 27

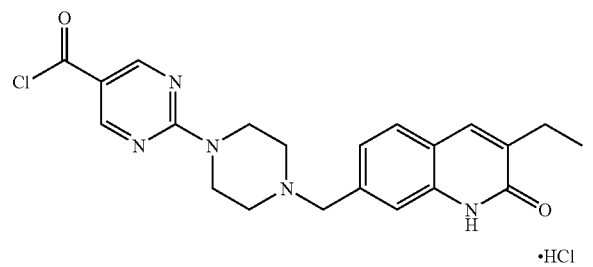 [SMILES: CCc1cc2ccc(CN3CCN(c4ncc(C(=O)Cl)cn4)CC3)cc2[nH]c1=O ; Cl]

Thionyl chloride (0.0148 mol) was added dropwise to a solution of compound 12 (0.0014 mol) in EDC (20 ml). The mixture was stirred at 70° C. for 15 hours, then evaporated till dryness. The residue was taken up in DCM. The mixture was evaporated till dryness twice, yielding intermediate 27. This product was used directly in the next reaction step.

Example A11 a) Preparation of Intermediate 28

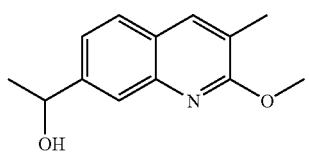 [SMILES: COc1nc2cc(C(C)O)ccc2cc1C]

nBuLi 1.6M (0.0154 mol) was added dropwise at −78° C. to a solution of 7-bromo-2-methyloxy-3-methyl-quinoline (0.014 mol) in THF (40 ml) under $N_2$ flow. The mixture was stirred at −78° C. for 30 minutes. Acetaldehyde (0.0169 mol) was added dropwise. The mixture was stirred at −78° C. for 1 hour and poured out into ice water. EtOAc was added. The mixture was extracted with EtOAc. The organic layer was washed with saturated NaCl, dried ($MgSO_4$), filtered and the solvent was evaporated. The residue was purified by column chromatography over silica gel (15-40 μm) (eluent: cyclohex-ane/EtOAc 80/20). The pure fractions were collected and the solvent was evaporated, yielding 1.1 g (36%) of intermediate 28.

b) Preparation of Intermediate 29

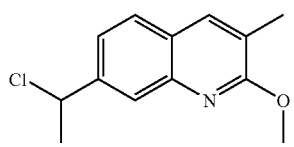 [SMILES: COc1nc2cc(C(C)Cl)ccc2cc1C]

Thionyl chloride (20 ml) was added dropwise at 10° C. to a solution of intermediate 28 (0.0092 mol) in DCM (20 ml). The mixture was stirred at 10° C. for 1 hour, then stirred at room temperature overnight and evaporated till dryness. The residue was taken up in DCM. The precipitate was filtered off and dried, yielding 2.3 g of intermediate 29.

Example A12 a) Preparation of Intermediate 30

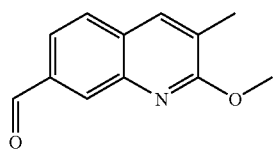

nBuLi 1.6M (0.018 mol) was added dropwise at −78° C. to a solution of 7-bromo-2-methyloxy-3-methyl-quinoline (0.015 mol) in THF (75 ml). The mixture was stirred at −78° C. for 20 minutes. A solution of 1-piperidinecarboxaldehyde (0.022 mol) in THF (2.5 ml) was added dropwise. The mixture was stirred at −78° C. for 1 hour, poured out on ice and extracted with EtOAc twice. The organic layer was washed with saturated NaCl, dried ($MgSO_4$), filtered and the solvent was evaporated. The residue was crystallized from DIPE. The precipitate was filtered off and dried, yielding 1.7 g (50%) of intermediate 30.

b) Preparation of Intermediate 31

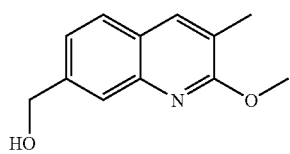

Sodium tetrahydroborate (0.0065 mol) was added portionwise at 5° C. to a solution of intermediate 30 (0.0054 mol) in MeOH (50 ml). The mixture was stirred at 5° C. for 1 hour and 30 minutes and poured out on ice. The precipitate was filtered, washed with water and dried. The residue (0.92 g, 83%) was taken up in DIPE. The precipitate was filtered off and dried, yielding 0.6 g of intermediate 31, melting point 98° C.

c) Preparation of Intermediate 32

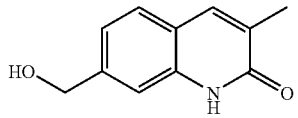

Hydrochloric acid 3N (5 ml) was added dropwise at room temperature to a solution of intermediate 31 (0.002 mol) in dioxane (5 ml). The mixture was stirred at 60° C. for 30 hours, then cooled to room temperature and poured out into ice water. The precipitate was filtered off and dried, yielding 0.33 g (71%) of intermediate 32. This product was used directly in the next reaction step.

d) Preparation of Intermediate 33

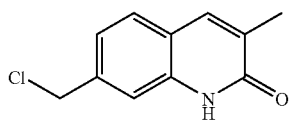

Thionyl chloride (4 ml) was added dropwise at 10° C. to a solution of intermediate 32 (0.0017 mol) in DCM (4 ml). The mixture was stirred at 10° C. for 1 hour, then stirred at room temperature overnight and evaporated till dryness. The residue was taken up in DCM, yielding intermediate 33.

Example A13 a) Preparation of Intermediate 34

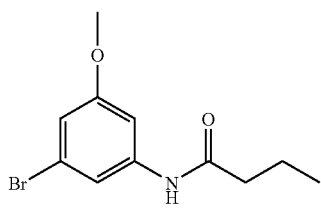

A solution of butanoyl chloride (0.0292 mol) in DCM (10 ml) was added dropwise to a solution of 3-bromo-5-methyloxybenzenamine (0.0292 mol) and $Et_3N$ (0.035 mol) in DCM (50 ml) at 5° C. under $N_2$ flow. The mixture was stirred at room temperature for 1 hour. $K_2CO_3$ 10% was added and the organic layer was decanted, dried ($MgSO_4$), filtered off and evaporated till dryness, yielding 8 g (100%) of intermediate 34.

b) Preparation of Intermediate 35

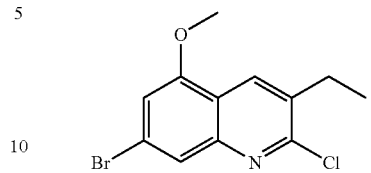

DMF (0.13 mol) was added at 10° C. to $POCl_3$ (0.302 mol) under $N_2$ flow. The mixture was warmed up to room temperature. Intermediate 34 (0.0863 mol) was added portion wise. The mixture was stirred at 110° C. for 5 hours, then cooled to room temperature and poured out into ice water. The precipitate was filtered, washed with $H_2O$ and taken up in DCM. The organic layer was washed with $K_2CO_3$ 10%, dried ($MgSO_4$), filtered and the solvent was evaporated till dryness. The residue was purified by column chromatography over silica gel (20-45 μm; eluent: DCM/cyclohexane 50/50). Two fractions were collected and the solvent was evaporated till dryness, yielding 7.5 g (29%) of intermediate 35, melting point 86° C.

c) Preparation of Intermediate 36

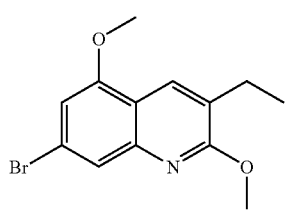 [SMILES: CCc1cc2c(OC)cc(Br)cc2nc1OC]

Intermediate 35 (0.001 mol), sodium methoxide solution (0.010 mol) and MeOH (4 ml) were heated overnight. The mixture was cooled to room temperature, poured out into ice water and extracted with DCM. The organic layer was washed with water, dried ($MgSO_4$), filtered and evaporated till dryness to give 260 mg (88%) of intermediate 36, melting point 118° C.

d) Preparation of Intermediate 37

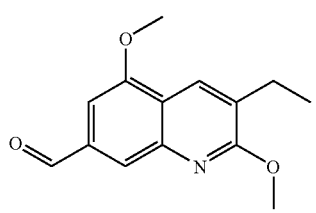 [SMILES: CCc1cc2c(OC)cc(C=O)cc2nc1OC]

Under $N_2$ flow at −70° C., BuLi (1.6M in hexane) was added dropwise to a solution of intermediate 36 in THF (3 ml). The mixture was stirred at −70° C. for 1 hour then a solution of DMF (8.779 mmol) in THF (10 ml) was added and the mixture was stirred for 1 hour. The reaction was quenched with water and extracted with DCM. The organic layer was washed with water, dried (MgSO₄) and evaporated till dryness. The residue was purified by column chromatography over silica gel (30 g; eluent DCM/cyclohexane 70/30). The pure fractions were collected and the solvents were evaporated till dryness to give 40 mg (19%) of intermediate 37.

e) Preparation of Intermediate 38

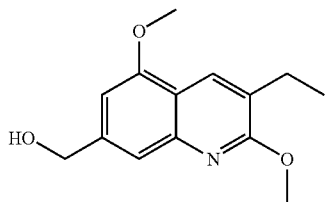

Sodium borohydride (0.196 mmol) was added portionwise to a solution of intermediate 37 in MeOH (5 ml) at 5° C., then the mixture was allowed to warm to room temperature and stirred for 1 hour. The mixture was poured out into ice water and extracted with DCM. The organic layer was washed with water, dried (MgSO₄), filtered and evaporated till dryness. The residue was purified by column chromatography over silica gel (10 g; eluent: DCM/MeOH 98/2) The pure fractions were collected and the solvents were evaporated till dryness to give 20 mg of intermediate 38.

f) Preparation of Intermediate 39

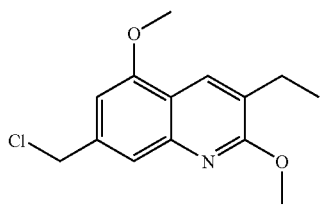 [SMILES: CCc1cc2c(OC)cc(CCl)cc2nc1OC]

Thionyl chloride (1.293 mmol) was added dropwise at 5° C. under N₂ flow to a solution of intermediate 38 in DCM (2 ml). The reaction mixture was stirred at 5° C. for 2 hours and then the solvent was evaporated to dryness. The residue was dissolved in EtOAc and washed with a saturated NaHCO₃ solution. The organic layer was decanted, dried (MgSO₄), filtered and evaporated to dryness, yielding 123 mg of intermediate 39.

g) Preparation of Intermediate 40

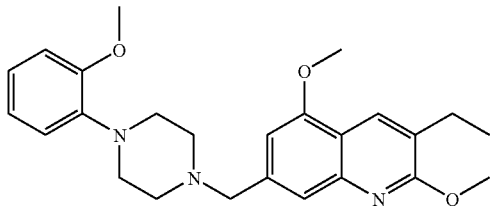 [SMILES: CCc1cc2c(OC)cc(CN3CCN(c4ccccc4OC)CC3)cc2nc1OC]

A mixture of intermediate 39 (0.00024 mol), 1-(2-methyloxyphenyl)-piperazine (0.00026 mol) and potassium carbonate (0.00072 mol) in acetonitrile (2 ml) was heated at 80° C. for 48 hours. The reaction mixture was cooled to room temperature, quenched with water and extracted with DCM. The organic layer was decanted, dried (MgSO₄), filtered and evaporated till dryness. The residue was purified by column chromatography over silica gel (10 g; eluent: DCM/MeOH/NH₄OH 97/3/0.1). The pure fractions were collected and the solvents were evaporated till dryness to give 21.6 mg of intermediate 40.

Example A14 a) Preparation of Intermediate 41

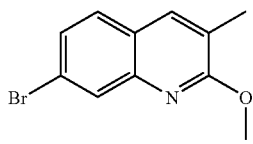

Methanol sodium salt (41 ml) was added dropwise to a solution of 7-bromo-2-chloro-3-methylquinoline (39 mmol) in MeOH (100 ml). The mixture was stirred at 80° C. for 6 hours. Then the mixture was poured into ice and H₂O and DCM was added. This mixture was extracted with DCM. The organic layer was dried (MgSO₄), filtered, and the solvent was evaporated, yielding 18.4 g of intermediate 41.

b) Preparation of Intermediate 42

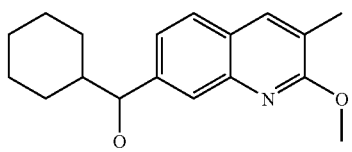 [SMILES: COc1nc2cc(C(O)C3CCCCC3)ccc2cc1C]

Intermediate 41 (1.98 mmol) was introduced in anhydrous THF at −78° C. under N₂ flow. BuLi (1.6M in hexane; 1.36 ml)) was added dropwise at −78° C. The mixture was stirred at −78° C. for half an hour and then cyclohexanecarboxaldehyde (3.97 mmol) was added drop wise. The mixture was stirred at −78° C. for 2.5 hours, then the mixture was poured into ice and H₂O and mixture was extracted with EtOAc. The organic layer was dried (MgSO₄), filtered, and the solvent was evaporated, yielding intermediate 42.

c) Preparation of Intermediate 43

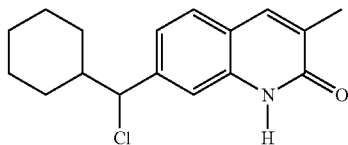 [SMILES: Cc1cc2ccc(C(Cl)C3CCCCC3)cc2[nH]c1=O]

Thionyl chloride (1.5 ml) was added dropwise at 10° C. to a solution of intermediate 42 (0.326 mmol) in DCM (1.5 ml). The mixture was stirred for one hour at 10° C. and one more at room temperature, then stirred for one night at room temperature. The solvent was evaporated until dryness and the residue was taken up with DCM. Intermediate 43 was used directly for the next step.

Example A15 a) Preparation of Intermediate 44

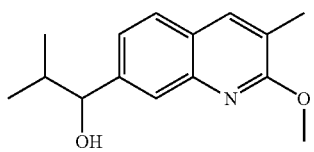 [SMILES: COc1nc2cc(C(O)C(C)C)ccc2cc1C]

Intermediate 41 (1.98 mmol) was introduced in THF (5 ml) at −78° C. under $N_2$ flow. BuLi (1.6M in hexane; 1.49 ml) was added drop wise at −78° C. The mixture was stirred at −78° C. for half of an hour, then 2-methylpropanal (3.97 mmol) was added dropwise and the mixture was stirred at −78° C. for 2.5 hours. The mixture was poured into ice and $H_2O$ and the mixture was extracted with EtOAc. The organic layer was dried ($MgSO_4$), filtered, and the solvent was evaporated, yielding 230 mg of intermediate 44.

b) Preparation of Intermediate 45

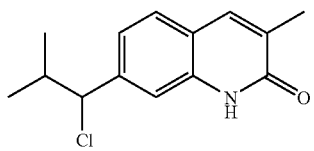 [SMILES: Cc1cc2ccc(C(Cl)C(C)C)cc2[nH]c1=O]

Thionyl chloride (0.5 ml) was added dropwise at 10° C. to a solution of intermediate 44 (0.0002 mol) in DCM (0.5 ml). The mixture was stirred at 10° C. for 1 hour, then stirred at room temperature for one extra hour and stirred at room temperature overnight. The solvent was evaporated till dryness and the residue was taken up in DCM and evaporated again, yielding intermediate 45 used directly in the next reaction step.

Example A16 a) Preparation of Intermediate 46

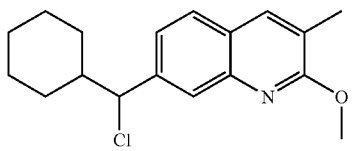

Thionyl chloride (1 ml) was added dropwise at 10° C. to a solution of intermediate 42 in DCM (1 ml). The mixture was stirred for one hour at 10° C. and one hour more at room temperature. The mixture was stirred for one night at room temperature, then the mixture was evaporated until dryness and taken up with DCM. The obtained intermediate 46 was used as such in the next reaction step.

Example A17 a) Preparation of Intermediate 47

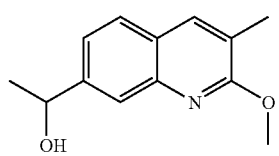

Intermediate 41 (0.0198 mol) was introduced in anhydrous THF (55 ml) at −78° C. under $N_2$ flow. nBuLi (1.6M in hexane, 1.3 ml, 0.0238 mol) was added drop wise at −78° C. The mixture was stirred at −78° C. for half of an hour. Then acetaldehyde (0.0238 mol) was added drop wise. The mixture was stirred at −78° C. for two hours and a half. The mixture was poured into ice and $H_2O$ and EtOAc was added. This mixture was extracted with EtOAc. The organic layer was dried ($MgSO_4$), filtered, and the solvent was evaporated. The residue was purified by column chromatography over silica gel (eluent: cyclohexane/EtOAc 90/10 and then 70/30). The pure fractions were collected and the solvent was evaporated, yielding 3.4 g (79%) of intermediate 47.

b) Preparation of Intermediate 48

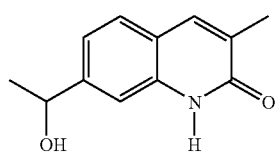

3N HCl (5 ml) was added dropwise to a solution of intermediate 47 (0.5 g) in Dioxane (5 ml) and then the mixture was refluxed at 60° C. for 30 hours. The mixture was cooled down and poured into ice water, then basified, extracted with EtOAc and dried ($MgSO_4$), filtered and evaporated, yielding 0.480 g of intermediate 48.

c) Preparation of Intermediate 49

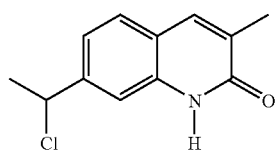

Thionyl chloride (5 ml) was added dropwise at 10° C. to a solution of intermediate 48 (0.0023 mol) in DCM (5 ml). The mixture was stirred at 10° C. for 1 hour, then stirred at room temperature overnight and evaporated till dryness. The residue was taken up in DCM and dried, yielding intermediate 49 used as such in the next reaction step.

B. Preparation of the Final Compounds

Example B1

Preparation of Compound 1

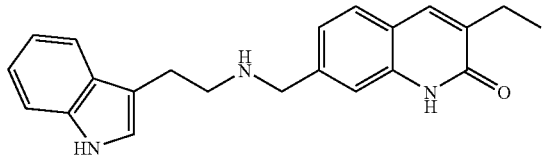 [SMILES: CCc1cc2ccc(CNCCc3c[nH]c4ccccc34)cc2[nH]c1=O]

A mixture of intermediate 4 (0.0007 mol), 1H-indole-3-ethanamine (0.0018 mol) and DIPEA (0.003 mol) in acetonitrile (20 ml) was stirred at 80° C. for 24 hours. Water was added. The mixture was extracted with DCM. The organic layer was separated, dried (MgSO$_4$), filtered and the solvent was evaporated. The residue (0.38 g) was purified by column chromatography over silica gel (5 μm) (eluent: DCM/MeOH/NH$_4$OH 98/2/0.2 to 92/8/0.8). The pure fractions were collected and the solvent was evaporated. The residue (0.14 g) was taken up in DIPE. The precipitate was filtered off and dried, yielding 0.13 g (50%) of compound 1, melting point 155° C.

Example B2

Preparation of Compound 2

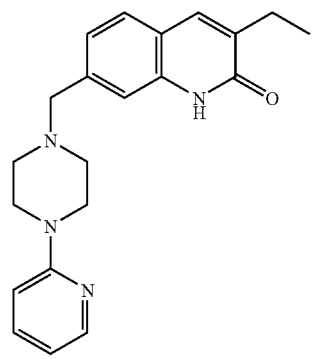 [SMILES: CCc1cc2ccc(CN3CCN(c4ccccn4)CC3)cc2[nH]c1=O]

A mixture of intermediate 4 (0.0007 mol), 1-(2-pyridinyl)-piperazine, monohydrochloride (0.0009 mol) and potassium carbonate (0.0022 mol) in acetonitrile (15 ml) was stirred at 80° C. for 3 hours and poured out into water. The precipitate was filtered, washed with water, then with EtOAc and dried, yielding 0.23 g (88%) of compound 2, melting point 252° C.

Example B3

Preparation of Compound 3

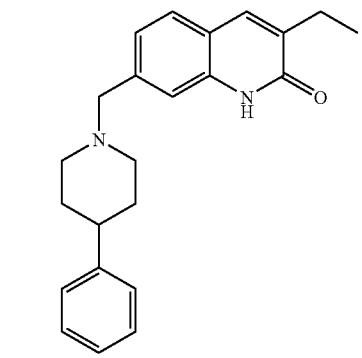 [SMILES: CCc1cc2ccc(CN3CCC(c4ccccc4)CC3)cc2[nH]c1=O]

A mixture of intermediate 5 (0.0011 mol) in hydrochloric acid 3N (10 ml) and dioxane (3 ml) was stirred and refluxed for 7 hours, poured out into water and made alkaline with NaHCO$_3$. The precipitate was filtered, washed with water, then with DIPE and dried. The residue (0.36 g) was taken up in DCM and water. The mixture was made alkaline with potassium carbonate and extracted with DCM. The organic layer was separated, dried (MgSO$_4$), filtered and the solvent was evaporated. The residue was taken up in DIPE. The precipitate was filtered off and dried, yielding 0.32 g (78%) of compound 3, melting point 184° C.

Example B4

Preparation of Compounds 4 and 5

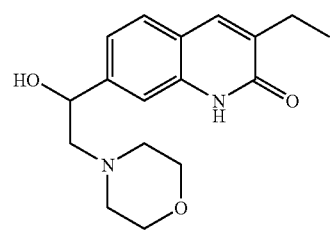

compound 4 and

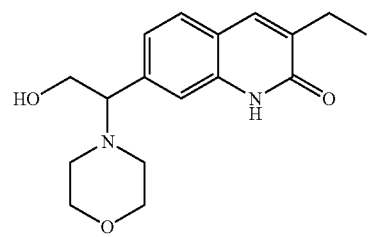

compound 5

Sodium hydride (0.0005 mol) was added at room temperature to a solution of intermediate 8 (0.0004 mol) and morpholine (0.0009 mol) in THF (10 ml). The mixture was stirred and refluxed for 72 hours. Water was added. The mixture was extracted with EtOAc twice. The organic layer was washed with saturated NaCl, dried (MgSO$_4$), filtered and the solvent was evaporated. This fraction (0.19 g) was purified by column chromatography over silica gel (5 μm) (eluent: DCM/MeOH/NH$_4$OH 97/3/0.3 to 88/12/1.2). Two fractions were collected and the solvent was evaporated, yielding 0.032 g (23%) of compound 4, melting point 163° C. and 0.012 g of residue which was dried, yielding 0.01 g (7%) of compound 5.

Example B5

Preparation of Compound 6

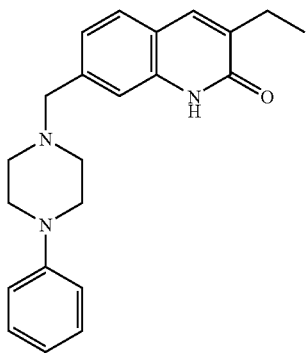 [SMILES: CCc1cc2ccc(CN3CCN(c4ccccc4)CC3)cc2[nH]c1=O]

A mixture of intermediate 4 (0.0007 mol), 1-phenyl-piperazine (0.0009 mol) and potassium carbonate (0.0022 mol) in acetonitrile (20 ml) was stirred at 80° C. for 3 hours and poured out into water. The precipitate was filtered, washed with water, then with DIPE and dried, yielding 0.22 g (86%) of compound 6, melting point 242° C.

Example B6

Preparation of Compound 7

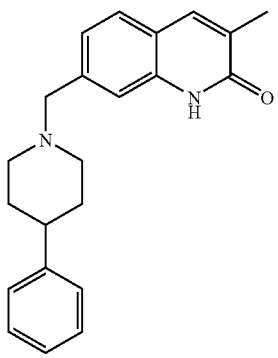 [SMILES: Cc1cc2ccc(CN3CCC(c4ccccc4)CC3)cc2[nH]c1=O]

A mixture of intermediate 10 (0.0005 mol) in hydrochloric acid 3N (5 ml) and dioxane (1 ml) was stirred and refluxed for 15 hours. Water then potassium carbonate were added. The mixture was extracted with DCM twice. The organic layer was separated, dried (MgSO$_4$), filtered and the solvent was evaporated. The residue was taken up in diethyl ether. The precipitate was filtered off and dried, yielding 0.17 g (89%) of compound 7, melting point 225° C.

Example B7

Preparation of Compound 8

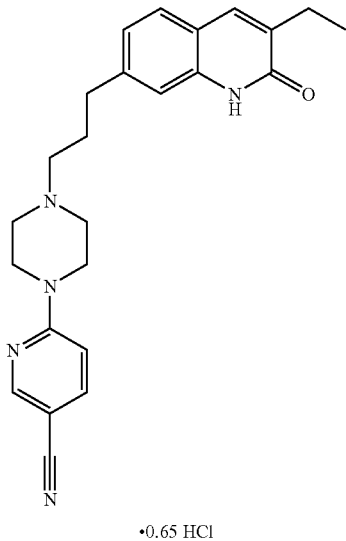 [SMILES: CCc1cc2ccc(CCCN3CCN(c4ccc(C#N)cn4)CC3)cc2[nH]c1=O]

•0.65 HCl

A mixture of intermediate 15 (0.0003 mol) in hydrochloric acid 3N (1.5 ml) and dioxane (1.5 ml) was stirred at 60° C. for 15 hours. Water was added. The mixture was basified with potassium carbonate. The precipitate was filtered, washed with water, then with diethyl ether and dried, yielding 0.07 g (43%) of compound 8, melting point 174° C.

Example B8

Preparation of Compound 9

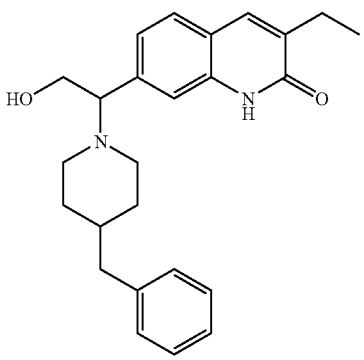

4-(phenylmethyl)-piperidine (0.0004 mol) was added to a mixture of intermediate 17 (0.0004 mol) and 1,4-dioxane-2,5-diol (0.0004 mol) in 1,1,1,3,3,3-hexafluoro-2-propanol (0.5 ml). The mixture was stirred at room temperature for 48 hours, then stirred at 60° C. for 48 hours. Water was added. The mixture was extracted with EtOAc. The organic layer was washed with saturated NaCl, dried (MgSO$_4$), filtered and the solvent was evaporated. The residue (0.7 g) was purified by column chromatography over silica gel (10 μm) (eluent:

DCM/MeOH/NH₄OH 95/5/0.5). The pure fractions were collected and the solvent was evaporated. The residue (0.11 g) was crystallized from diethyl ether. The precipitate was filtered off and dried, yielding 0.1 g (14%) of compound 9, melting point 172° C.

Example B9

Preparation of Compound 10

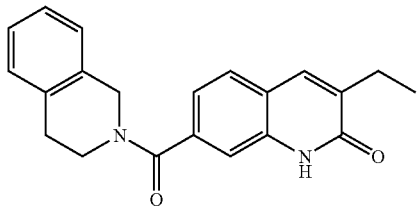 [SMILES: CCc1cc2ccc(C(=O)N3CCc4ccccc4C3)cc2[nH]c1=O]

EDC (0.0011 mol) then HOBT (0.0009 mol) were added at room temperature to a solution of intermediate 20 (0.0006 mol) and triethylamine (0.0018 mol) in THF/DCM (20 ml) under N₂ flow. The mixture was stirred at room temperature for 10 minutes. 1,2,3,4-tetrahydro-isoquinoline (0.0009 mol) was added. The mixture was stirred at room temperature for 24 hours, then stirred at room temperature for 24 hours, poured out into water and extracted with DCM. The organic layer was separated, dried (MgSO₄), filtered and the solvent was evaporated. The residue (0.3 g) was purified by column chromatography over silica gel (10 μm). The pure fractions were collected and the solvent was evaporated. The residue (0.085 g) was crystallized from diethyl ether. The precipitate was filtered off and dried, yielding 0.051 g of compound 10, melting point 255° C.

Example B10 a) Preparation of Compound 11

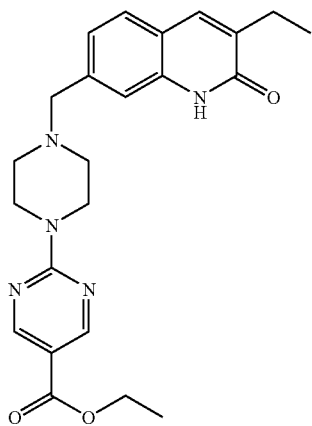 [SMILES: CCOC(=O)c1cnc(N2CCN(Cc3ccc4cc(CC)c(=O)[nH]c4c3)CC2)nc1]

A mixture of intermediate 4 (0.0022 mol), 2-(1-piperazinyl)-5-pyrimidinecarboxylic acid, ethyl ester (0.0022 mol) and potassium carbonate (0.0067 mol) in acetonitrile (60 ml) was stirred at 80° C. for 3 hours. Water was added. The precipitate was filtered, washed with water, then with diethyl ether and dried, yielding 0.92 g (97%) of compound 11, melting point 235° C.

b) Preparation of Compound 12

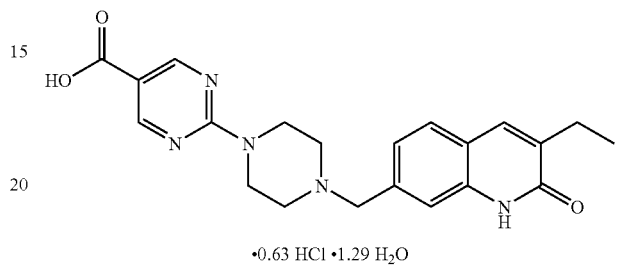

•0.63 HCl •1.29 H₂O

A mixture of compound 11 (0.0019 mol) in sodium hydroxide 1N (40 ml) and THF (40 ml) was stirred at room temperature for 48 hours, then neutralized with HCl 3N. The solvent was evaporated. The precipitate was filtered, washed with water, then with diethyl ether and dried. The residue (0.72 g) was taken up in EtOH (30 ml). Sodium hydroxide was added. The mixture was stirred and refluxed for 15 hours. The solvent was evaporated. Water was added. The mixture was made acid with HCl 3N. The precipitate was filtered, washed with water, then with diethyl ether and dried, yielding 0.72 g (86%) of compound 12.

Example B11

Preparation of Compound 13

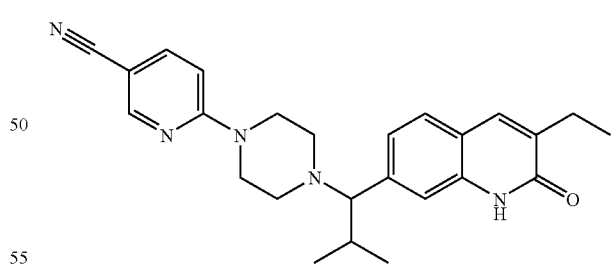

A mixture of intermediate 23 (0.0006 mol), 6-(1-piperazinyl)-3-pyridinecarbonitrile (0.0007 mol) and potassium carbonate (0.0018 mol) in acetonitrile (5 ml) was stirred and refluxed for 15 hours. Acetonitrile (10 ml) was added. The mixture was stirred and refluxed for 24 hours, then poured out into water and extracted twice with DCM. The organic layer was separated, dried (MgSO₄), filtered and the solvent was evaporated. The residue (0.3 g) was purified by column chromatography over silica gel (3.5 μm) (eluent: DCM/MeOH/NH₄OH 99/1/0.1 to 96/4/0.4). The pure fractions were col-

Example B12

Preparation of Compound 14

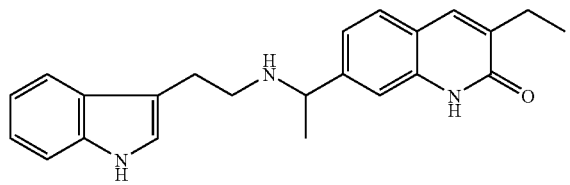 [SMILES: CCc1cc2ccc(C(C)NCCc3c[nH]c4ccccc34)cc2[nH]c1=O]

A mixture of intermediate 26 (0.0012 mol), 1H-indole-3-ethanamine (0.0031 mol) and DIPEA (0.005 mol) in acetonitrile (25 ml) was stirred at 80° C. for 48 hours. Water was added. The mixture was extracted with DCM twice. The organic layer was washed with water several times, dried (MgSO$_4$), filtered and the solvent was evaporated. The residue (0.6 g) was purified by column chromatography over Sunfire (5 µm) (eluent: DCM/MeOH/NH$_4$OH 98/2/0.2 to 92/8/0.8). The pure fractions were collected and the solvent was evaporated. The residue (0.23 g) was crystallized from diethyl ether. The precipitate was filtered, washed with EtOAc, then with diethyl ether and dried, yielding 0.15 g (44%) of compound 14, melting point 170° C.

Example B13

Preparation of Compound 15

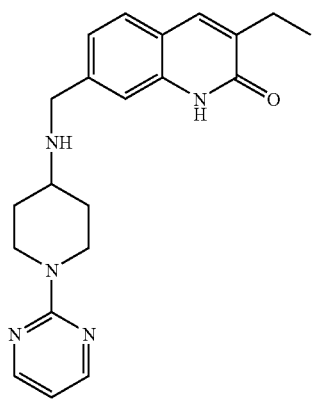 [SMILES: CCc1cc2ccc(CNC3CCN(c4ncccn4)CC3)cc2[nH]c1=O]

A mixture of intermediate 4 (0.0003 mol), 1-(2-pyrimidinyl)-4-piperidinamine (0.0006 mol) and potassium carbonate (0.0011 mol) in acetonitrile (10 ml) was stirred and refluxed for 3 hours. Water was added. The mixture was extracted with DCM. The organic layer was separated, dried (MgSO$_4$), filtered and the solvent was evaporated. The residue (0.2 g) was purified by column chromatography over silica gel (5 µm) (eluent: DCM/MeOH/NH$_4$OH 97/3/0.3 to 88/12/1.2). The pure fractions were collected and the solvent was evaporated. The residue (0.095 g) was taken up in DIPE. The precipitate was filtered off and dried, yielding 0.088 g (65%) of compound 15, melting point 168° C.

Example B14

Preparation of Compound 16

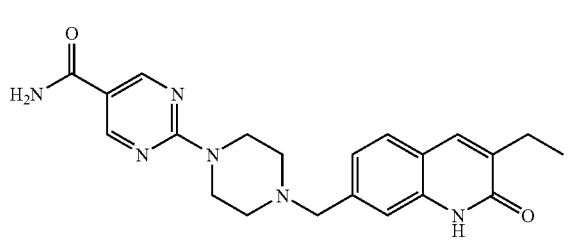 [SMILES: CCc1cc2ccc(CN3CCN(c4ncc(C(N)=O)cn4)CC3)cc2[nH]c1=O]

Ammonium hydroxide 10% (0.0037 mol) was added dropwise at 5° C. to a suspension of intermediate 27 (0.0007 mol) in DCM (20 ml). The mixture was stirred at 5° C. for 15 minutes, then stirred at room temperature for 2 hours. Water (15 ml) was added. DCM was evaporated. The precipitate was filtered, washed with water, then with diethyl ether and dried, yielding 0.22 g (76%) of compound 16, melting point >250° C.

Example B15

Preparation of Compound 17

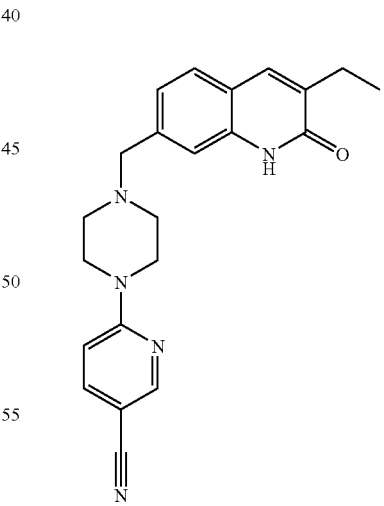

A mixture of intermediate 4 (0.00028 mol), 6-(1-piperazinyl)-3-pyridinecarbonitrile (0.00037 mol) and DIPEA (0.0011 mol) in acetonitrile (7.5 ml) was stirred at 80° C. for 3 hours and poured out into water. The precipitate was filtered, washed with water, then with DIPE and dried, yielding 0.080 g (76%) of compound 17.

Example B16

Preparation of Compound 18

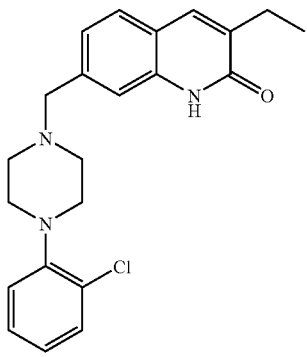 [SMILES: CCc1cc2ccc(CN3CCN(c4ccccc4Cl)CC3)cc2[nH]c1=O]

A mixture of intermediate 4 (0.00028 mol), 1-(2-chlorophenyl)-piperazine (0.00037 mol) and DIPEA (0.0007 mol) in acetonitrile (7.5 ml) was stirred at 80° C. for 3 hours and poured out into water. The precipitate was filtered, washed with water, then with DIPE and dried, yielding 0.039 g (36%) of compound 18.

Example B17

Preparation of Compound 19

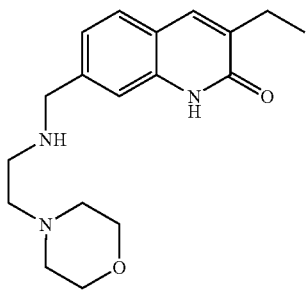 [SMILES: CCc1cc2ccc(CNCCN3CCOCC3)cc2[nH]c1=O]

A mixture of intermediate 4 (0.00028 mol), 4-morpholineethanamine (0.00056 mol) and DIPEA (0.0014 mol) in acetonitrile (7.5 ml) was stirred at 80° C. for 3 hours and poured out into water. The mixture was extracted with DCM and the solvent was evaporated. The residue was purified by column chromatography over silica gel (15-40 μm) (eluent: gradient from DCM 100 to DCM/MeOH/NH$_4$OH 95/5/0.1). The pure fractions were collected and the solvent was evaporated, yielding 0.032 g (36%) of compound 19.

Example B18

Preparation of Compound 20

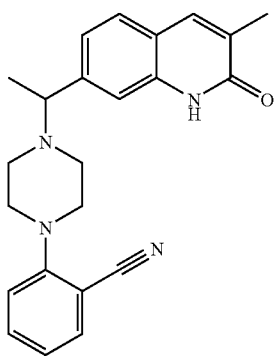 [SMILES: Cc1cc2ccc(C(C)N3CCN(c4ccccc4C#N)CC3)cc2[nH]c1=O]

A solution of intermediate 29 (0.0004 mol), 2-(1-piperazinyl)-benzonitrile (0.09 ml) and potassium carbonate (0.18 g) in acetonitrile (3 ml) was stirred at 80° C. for 24 hours, extracted with DCM, washed with water and dried over MgSO$_4$. The residue was purified by column chromatography over silica gel (eluent: DCM/MEOH/NH$_4$OH 99/1/0.2). The pure fractions were collected and the solvent was evaporated, yielding compound 20, melting point 190° C.

Example B19

Preparation of Compound 21

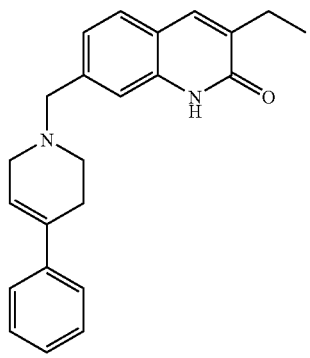 [SMILES: CCc1cc2ccc(CN3CC=C(c4ccccc4)CC3)cc2[nH]c1=O]

A mixture of intermediate 4 (0.0003 mol), 1,2,3,6-tetrahydro-4-phenyl-pyridine (0.0004 mol) and N-ethyl-N-(1-methylethyl)-2-propanamine (0.096 g) in acetonitrile (7.5 ml) was stirred at 80° C. for 3 hours. Water was added. The precipitate was filtered, washed with water then with ethylic ether and dried, yielding compound 21.

Example B20

Preparation of Compound 22

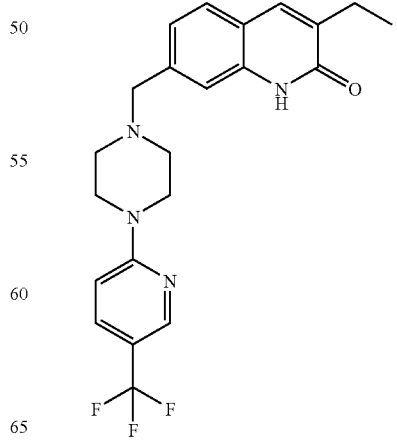

A mixture of intermediate 4 (0.075 g), 1-[5-(trifluoromethyl)-2-pyridinyl]-piperazine (0.0004 mol) and N-ethyl-N-(1-methylethyl)-2-propanamine (0.0011 mol) in acetonitrile (7.5 mol) was stirred at 80° C. for 3 hours. Water was added. The precipitate was filtered, washed with water then with diethyl ether and dried, yielding compound 22.

Example B21

Preparation of Compound 23

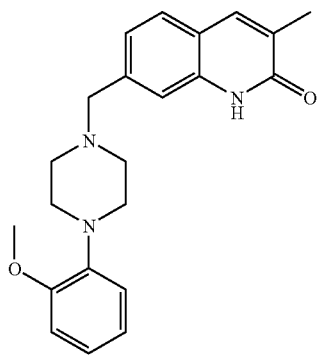 [SMILES: COc1ccccc1N1CCN(Cc2ccc3cc(C)c(=O)[nH]c3c2)CC1]

A mixture of intermediate 33 ((0.0003 mol), 1-(2-methyloxyphenyl)-piperazine (0.0004 mol) and potassium carbonate (0.0009 mol) in acetonitrile (3 ml) was stirred at 80° C. for 24 hours, extracted with DCM, washed with water and dried over MgSO$_4$. The residue was purified by column chromatography over silica gel (eluent: DCM/MeOH/NH$_4$OH 99/1/0.1 to 93/7/0.7). The pure fractions were collected and the solvent was evaporated. A part (0.061 g) of the residue (0.107 g) was crystallized from DIPE. The precipitated was filtered off and dried, yielding compound 23, melting point 198° C.

Example B22

Preparation of Compound 64

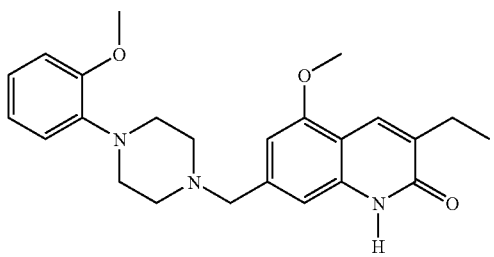 [SMILES: CCc1cc2c(OC)cc(CN3CCN(c4ccccc4OC)CC3)cc2[nH]c1=O]

Intermediate 40 (0.0000512 mol), 3N HCl (0.22 ml) and dioxane (0.22 ml) were heated overnight at 80° C. The mixture was cooled to room temperature and poured into ice water, then basified with K$_2$CO$_3$ 10% and extracted with EtOAc. The organic layer was washed with water and a solution of saturated NaCl, then dried (MgSO$_4$), filtered and evaporated till dryness. The obtained residue was purified by chromatography over silica gel (15-40 µm; eluent: DCM/MeOH/NH$_4$OH: 97/3/0.1). The pure fractions were collected and the solvents were evaporated till dryness. The residue was taken up from Et$_2$O and dried, yielding 9.5 mg (46%) of compound 64, melting point 80° C.

Example B23

Preparation of Compound 65

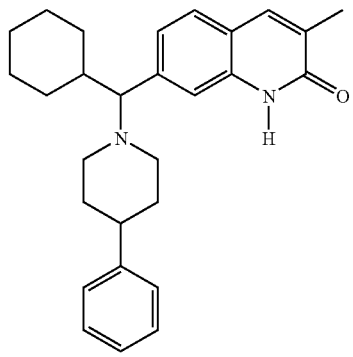 [SMILES: Cc1cc2ccc(C(C3CCCCC3)N3CCC(c4ccccc4)CC3)cc2[nH]c1=O]

A mixture of intermediate 43 (0.0006 mol), 4-phenylpiperidine (0.0008 mol) and potassium carbonate (0.0019 mol) in acetonitrile (5 ml) was stirred at 80° C. for 48 hours and extracted with DCM. The organic layer was washed with H$_2$O, dried (MgSO$_4$), filtered and the solvent was evaporated. The residue was purified by column chromatography over silica gel (eluent: DCM/MeOH 99/1; 10 µm). The pure fractions were collected and the solvent was evaporated. The residue was taken up in DCM and diethyl ether and dried, yielding 0.0385 g (15%) of compound 65.

Example B24

Preparation of Compound 66

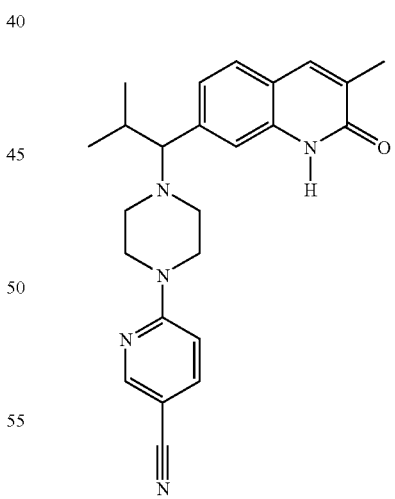

A mixture of intermediate 45 (0.0003 mol), 6-(1-piperazinyl)-3-pyridinecarbonitrile (0.0004 mol) and potassium carbonate (0.001 mol) in acetonitrile (3 ml) was stirred at 80° C. for 48 hours, then stirred at room temperature for 2 days and extracted with DCM. The organic layer was washed with water, dried (MgSO$_4$), filtered and the solvent was evaporated. The residue (0.14 g) was purified by column chromatography over silica gel (eluent: DCM/MeOH/NH$_4$OH 99/1/

0.1). The pure fractions were collected and the solvent was evaporated. The residue (0.016 g) was taken up in DCM/diethyl ether and dried, yielding: 0.014 g (11%) of compound 66.

Example B25

Preparation of Compound 67

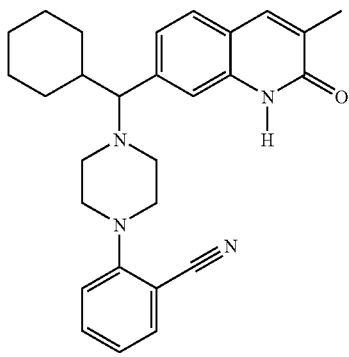 [SMILES: Cc1cc2ccc(C(C3CCCCC3)N3CCN(c4ccccc4C#N)CC3)cc2[nH]c1=O]

A mixture of intermediate 46 (0.0004 mol), 2-(1-piperazinyl)benzonitrile (0.0005 mol) and $K_2CO_3$ (0.001 mol) in acetonitrile (2 ml) was stirred at 80° C. for 48 hours, then the reaction mixture was stirred at room temperature for 2 days and extracted with DCM. The organic layer was washed with water, dried ($MgSO_4$), filtered and the solvent was evaporated. The residue was purified by column chromatography over over silica gel (eluent: DCM/MeOH/$NH_4OH$ 97/3/0.5). The pure fractions were collected and the solvent was evaporated. The residue was taken up in DCM/diethyl ether and was evaporated till dryness, yielding 0.0077 g (5%) of compound 67.

Example B26

Preparation of Compound 68

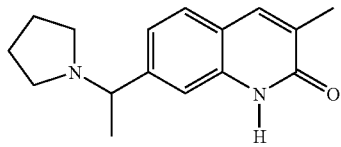 [SMILES: Cc1cc2ccc(C(C)N3CCCC3)cc2[nH]c1=O]

A mixture of intermediate 49 (0.0005 mol), pyrrolidine (0.0006 mol) and $K_2CO_3$ (0.0014 mol) in DMF (5 ml) was stirred at 80° C. for 4 hours and was then refluxed overnight. Ice water was added and the mixture was extracted with DCM. The organic layer was dried and the solvent was evaporated. The residue was purified by chromatography over silica gel (eluent: DCM/MeOH/$NH_4OH$ 95/5/0.2). The pure fraction was collected and the solvent was evaporated, yielding 0.012 g of compound 68, melting point 133° C.

Table F-1 lists the compounds that were prepared according to one of the above Examples. The compounds marked with an asterisk were prepared as described in the above B Examples. The remaining compounds were prepared in an analogous manner to the respective specified Example.

TABLE F-1

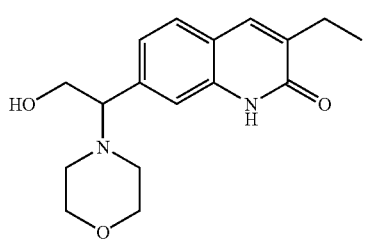 [SMILES: CCc1cc2ccc(C(CO)N3CCOCC3)cc2[nH]c1=O]

Co. No. 1; Ex. [B1]; mp. 155° C.

Co. No. 2*; Ex. [B2]; mp. 252° C.

Co. No. 3*; Ex. [B3]; mp. 184° C.

Co. No. 4*; Ex. [B4]; mp. 163° C.

Co. No. 5*; Ex. [B4]

TABLE F-1-continued
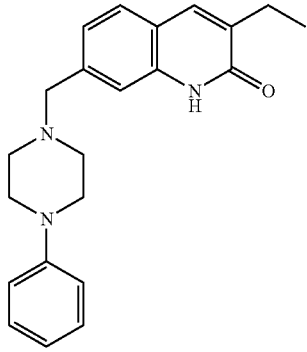 [SMILES: CCc1cc2ccc(CN3CCN(c4ccccc4)CC3)cc2[nH]c1=O]
Co. No. 6*; Ex. [B5]; mp. 242° C.
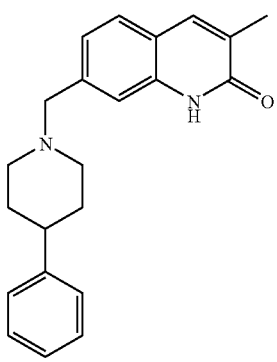 [SMILES: Cc1cc2ccc(CN3CCC(c4ccccc4)CC3)cc2[nH]c1=O]
Co. No. 7*; Ex. [B6]; mp. 225° C.
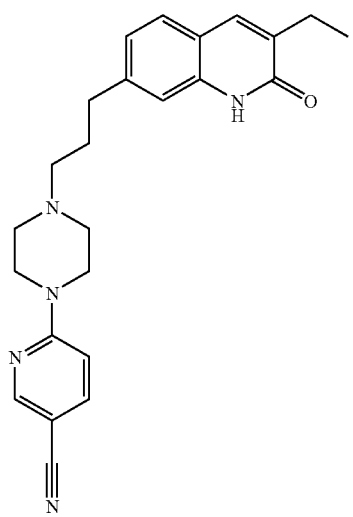 [SMILES: CCc1cc2ccc(CCCN3CCN(c4ccc(C#N)cn4)CC3)cc2[nH]c1=O]
•0.65 HCl; Co. No. 8*; Ex. [B7]; mp. 174° C.
TABLE F-1-continued
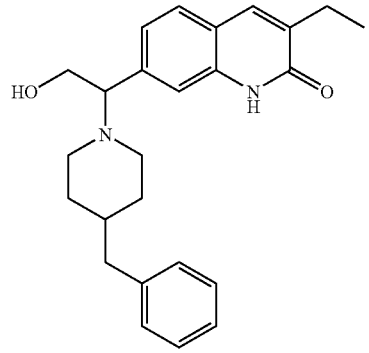 [SMILES: CCc1cc2ccc(C(CO)N3CCC(Cc4ccccc4)CC3)cc2[nH]c1=O]
Co. No. 9*; Ex. [B8]; mp. 172° C.
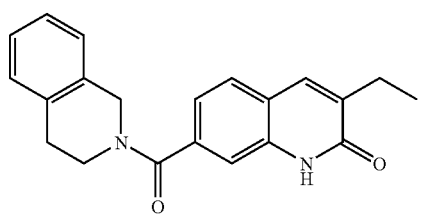 [SMILES: CCc1cc2ccc(C(=O)N3CCc4ccccc4C3)cc2[nH]c1=O]
Co. No. 10*; Ex. [B9]; mp. 255° C.
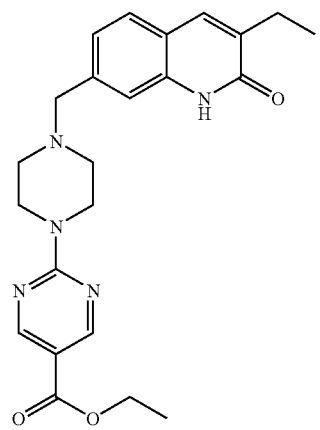 [SMILES: CCOC(=O)c1cnc(N2CCN(Cc3ccc4cc(CC)c(=O)[nH]c4c3)CC2)nc1]
Co. No. 11*; Ex. [B10a]; mp. 235° C.
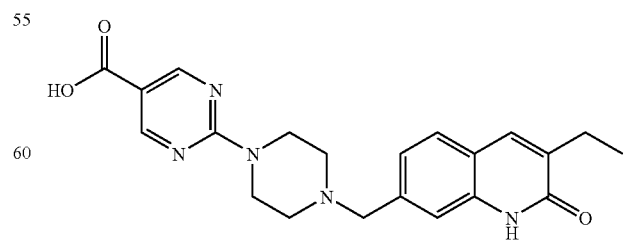
•0.63 HCl •1.29 H$_2$O; Co. No. 12*; Ex. [B10]

TABLE F-1-continued
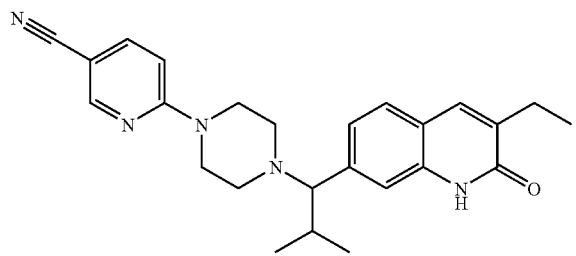 [SMILES: CCc1cc2ccc(C(C(C)C)N3CCN(c4ccc(C#N)cn4)CC3)cc2[nH]c1=O]
Co. No. 13*; Ex. [B11]; mp. 135° C.
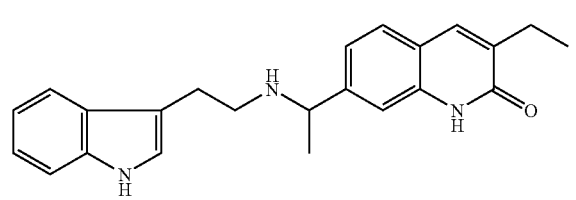 [SMILES: CCc1cc2ccc(C(C)NCCc3c[nH]c4ccccc34)cc2[nH]c1=O]
Co. No. 14*; Ex. [B12]; mp. 170° C.
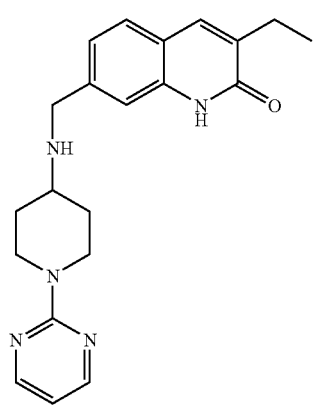 [SMILES: CCc1cc2ccc(CNC3CCN(c4ncccn4)CC3)cc2[nH]c1=O]
Co. No. 15*; Ex. [B13]; mp. 168° C.
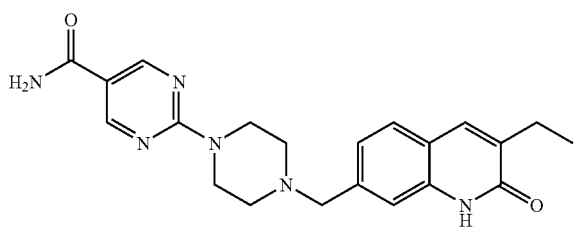 [SMILES: CCc1cc2ccc(CN3CCN(c4ncc(C(N)=O)cn4)CC3)cc2[nH]c1=O]
Co. No. 16*; Ex. [B14]; mp. >250° C.
TABLE F-1-continued
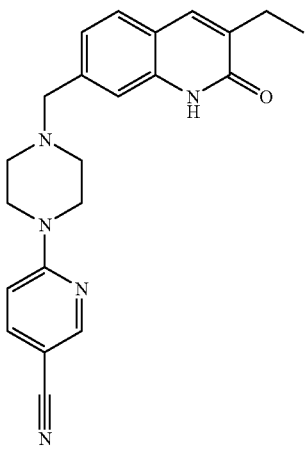 [SMILES: CCc1cc2ccc(CN3CCN(c4ccc(C#N)cn4)CC3)cc2[nH]c1=O]
Co. No. 17*; Ex. [B15]
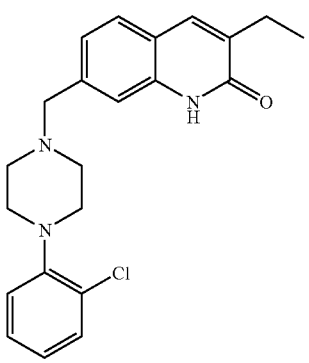 [SMILES: CCc1cc2ccc(CN3CCN(c4ccccc4Cl)CC3)cc2[nH]c1=O]
Co. No. 18*; Ex. [B16]
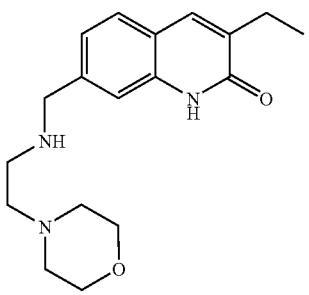 [SMILES: CCc1cc2ccc(CNCCN3CCOCC3)cc2[nH]c1=O]
Co. No. 19*; Ex. [B17]
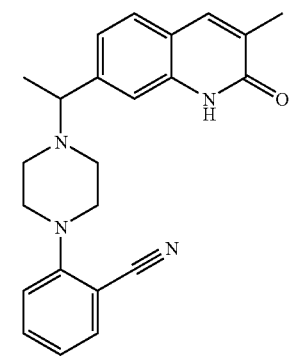 [SMILES: Cc1cc2ccc(C(C)N3CCN(c4ccccc4C#N)CC3)cc2[nH]c1=O]
Co. No. 20*; Ex. [B18]; mp. 190° C.

TABLE F-1-continued
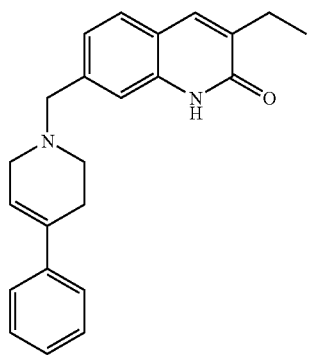 [SMILES: CCc1cc2ccc(CN3CC=C(c4ccccc4)CC3)cc2[nH]c1=O]
Co. No. 21*; Ex. [B 19]
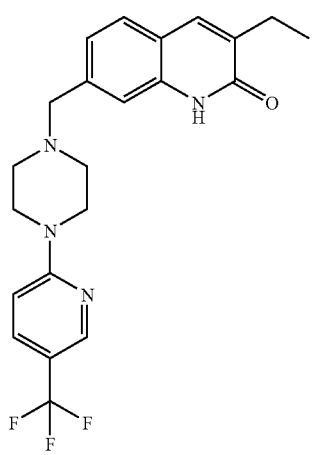 [SMILES: CCc1cc2ccc(CN3CCN(c4ccc(C(F)(F)F)cn4)CC3)cc2[nH]c1=O]
Co. No. 22*; Ex. [B20]
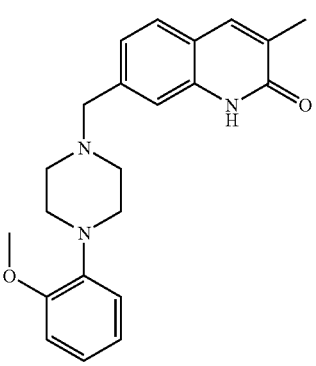 [SMILES: COc1ccccc1N1CCN(Cc2ccc3cc(C)c(=O)[nH]c3c2)CC1]
Co. No. 23*; Ex. [B21]; mp. 198° C.
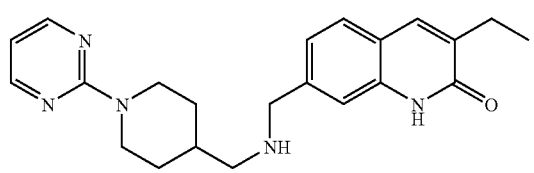 [SMILES: CCc1cc2ccc(CNCC3CCN(c4ncccn4)CC3)cc2[nH]c1=O]
Co. No. 25; Ex. [B1]; mp. 128° C.
TABLE F-1-continued
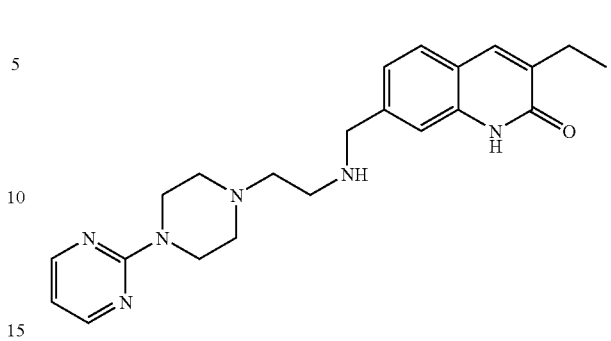
Co. No. 24; Ex. [B1]; mp. 155° C.
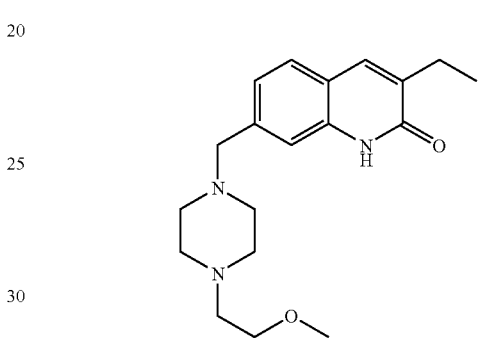
Co. No. 27; Ex. [B2]; mp. 138° C.
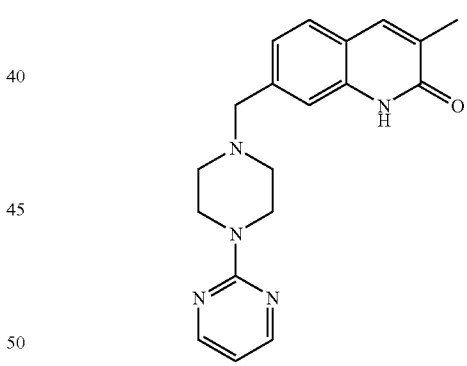
Co. No. 26; Ex. [B2]; mp. >250° C.
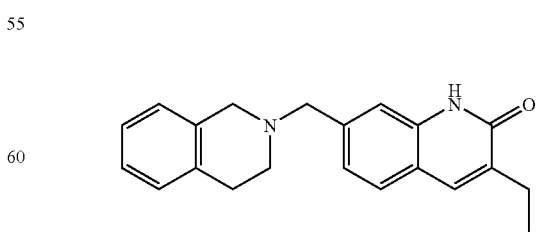
Co. No. 29; Ex. [B2]; mp. 230° C.

TABLE F-1-continued
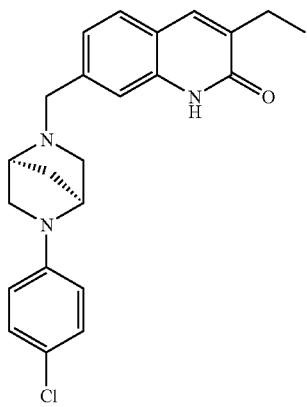 [SMILES: CCc1cc2ccc(CN3C[C@@H]4C[C@H]3CN4c3ccc(Cl)cc3)cc2[nH]c1=O]
Co. No. 28; Ex. [B2]; mp. 203° C.
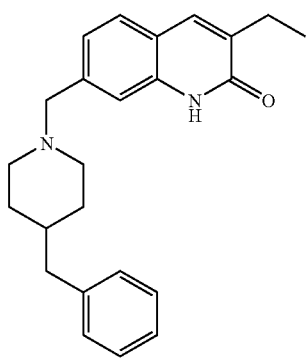 [SMILES: CCc1cc2ccc(CN3CCC(Cc4ccccc4)CC3)cc2[nH]c1=O]
Co. No. 31; Ex. [B3]; mp. 174° c
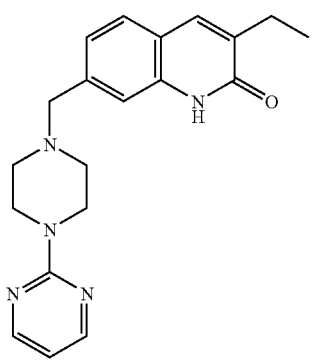 [SMILES: CCc1cc2ccc(CN3CCN(c4ncccn4)CC3)cc2[nH]c1=O]
Co. No. 30; Ex. [B2]; mp. 222° C.
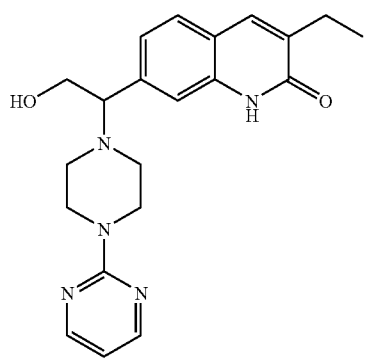 [SMILES: CCc1cc2ccc(C(CO)N3CCN(c4ncccn4)CC3)cc2[nH]c1=O]
Co. No. 33; Ex. [B4]
TABLE F-1-continued
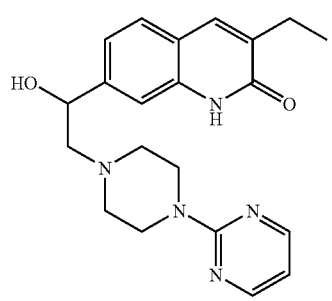 [SMILES: CCc1cc2ccc(C(O)CN3CCN(c4ncccn4)CC3)cc2[nH]c1=O]
Co. No. 32; Ex. [B4], mp. 226° C.
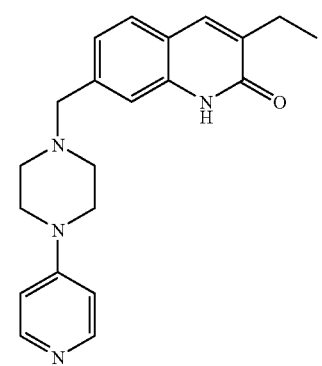 [SMILES: CCc1cc2ccc(CN3CCN(c4ccncc4)CC3)cc2[nH]c1=O]
Co. No. 35; Ex. [B15]
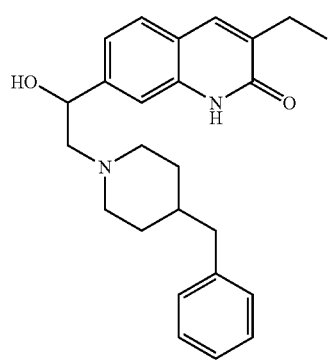 [SMILES: CCc1cc2ccc(C(O)CN3CCC(Cc4ccccc4)CC3)cc2[nH]c1=O]
Co. No. 34; Ex. [B4], mp. 224° C.
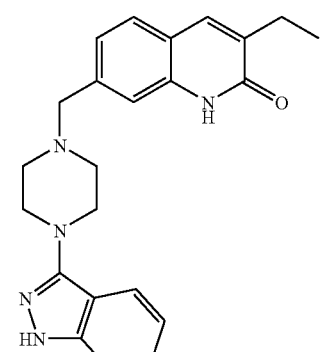
Co. No. 37; Ex. [B15]

TABLE F-1-continued
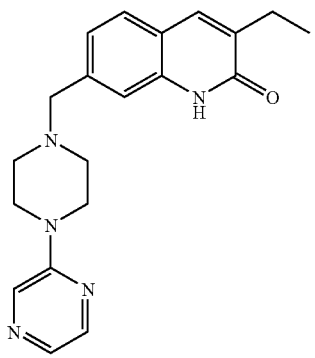 [SMILES: CCc1cc2ccc(CN3CCN(c4cnccn4)CC3)cc2[nH]c1=O]
Co. No. 36; Ex. [B15]
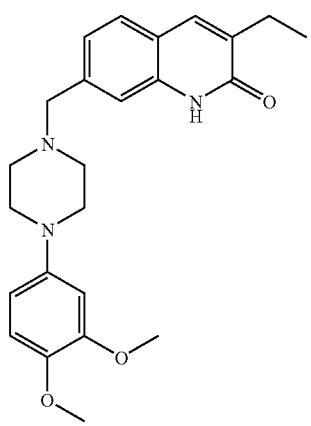 [SMILES: CCc1cc2ccc(CN3CCN(c4ccc(OC)c(OC)c4)CC3)cc2[nH]c1=O]
Co. No. 39; Ex. [B15]
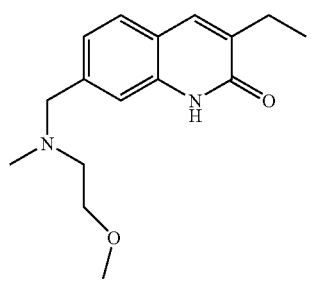 [SMILES: CCc1cc2ccc(CN(C)CCOC)cc2[nH]c1=O]
Co. No. 38; Ex. [B15]
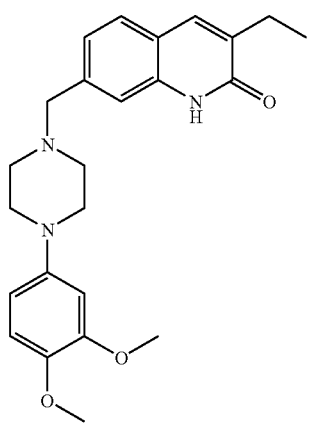 [SMILES: CCc1cc2ccc(CN3CCN(c4ccc(OC)c(OC)c4)CC3)cc2[nH]c1=O]
Co. No. 41; Ex. [B15].
TABLE F-1-continued
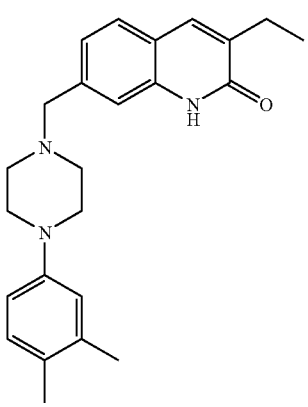 [SMILES: CCc1cc2ccc(CN3CCN(c4ccc(C)c(C)c4)CC3)cc2[nH]c1=O]
Co. No. 40; Ex. [B15]
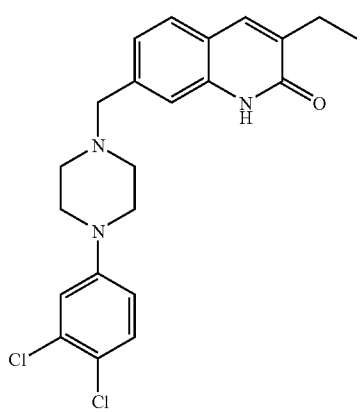 [SMILES: CCc1cc2ccc(CN3CCN(c4ccc(Cl)c(Cl)c4)CC3)cc2[nH]c1=O]
Co. No. 43; Ex. [B16]
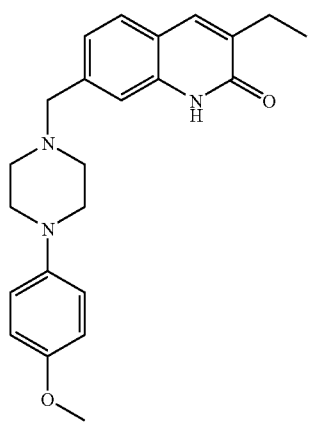 [SMILES: CCc1cc2ccc(CN3CCN(c4ccc(OC)cc4)CC3)cc2[nH]c1=O]
Co. No. 42; Ex. [B16]

TABLE F-1-continued
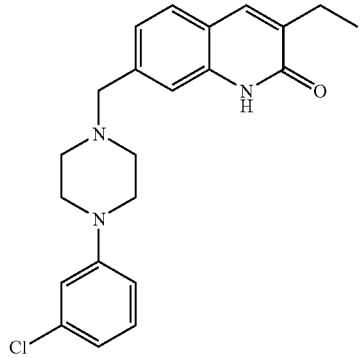 [SMILES: CCc1cc2ccc(CN3CCN(c4cccc(Cl)c4)CC3)cc2[nH]c1=O]
Co. No. 45; Ex. [B16]
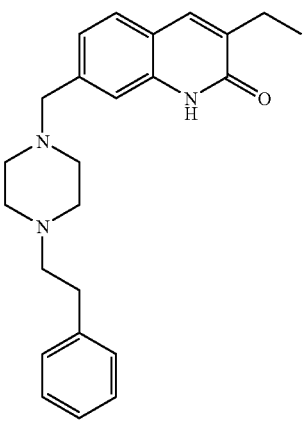 [SMILES: CCc1cc2ccc(CN3CCN(CCc4ccccc4)CC3)cc2[nH]c1=O]
Co. No. 44; Ex. [B16]
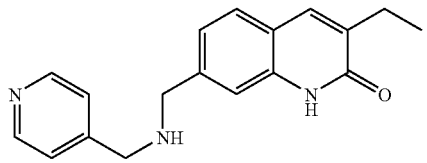 [SMILES: CCc1cc2ccc(CNCc3ccncc3)cc2[nH]c1=O]
Co. No. 47; Ex. [B17]
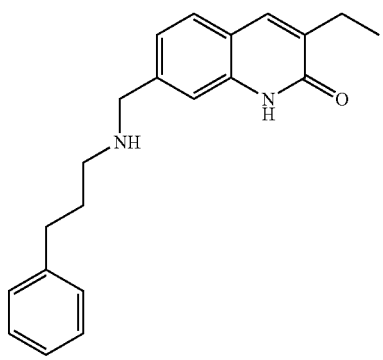 [SMILES: CCc1cc2ccc(CNCCCc3ccccc3)cc2[nH]c1=O]
Co. No. 46; Ex. [B17]
TABLE F-1-continued
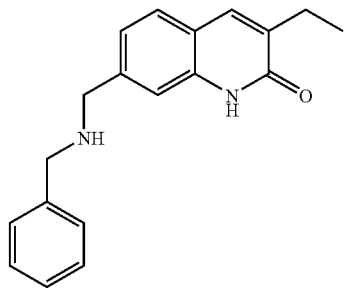 [SMILES: CCc1cc2ccc(CNCc3ccccc3)cc2[nH]c1=O]
Co. No. 49; Ex. [B17]
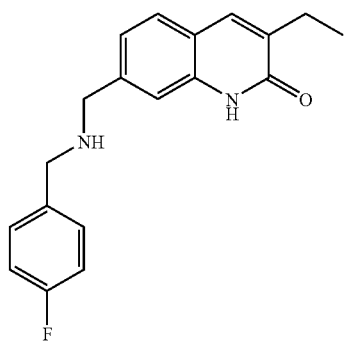 [SMILES: CCc1cc2ccc(CNCc3ccc(F)cc3)cc2[nH]c1=O]
Co. No. 48; Ex. [B17]
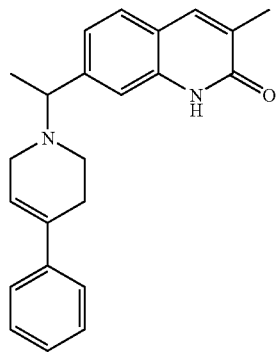
Co. No. 51; Ex. [B1]; mp. 224° C.
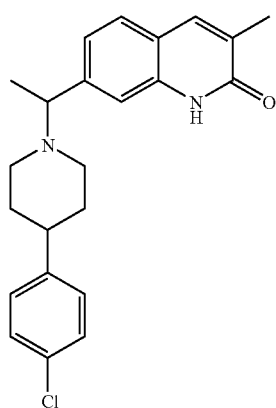 [SMILES: Cc1cc2ccc(C(C)N3CCC(c4ccc(Cl)cc4)CC3)cc2[nH]c1=O]
Co. No. 50; Ex. [B1]; mp. 223° C.

TABLE F-1-continued
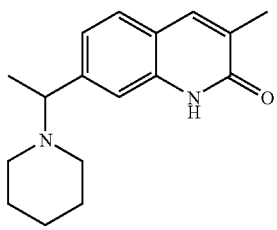 [SMILES: Cc1cc2ccc(C(C)N3CCCCC3)cc2[nH]c1=O]
Co. No. 53; Ex. [B1]; mp. 148° C.
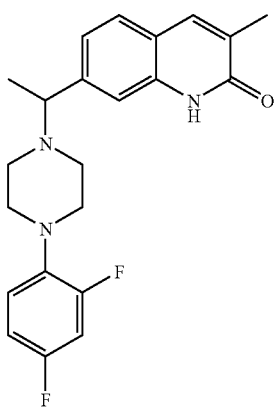 [SMILES: Cc1cc2ccc(C(C)N3CCN(c4ccc(F)cc4F)CC3)cc2[nH]c1=O]
Co. No. 52; Ex. [B1]; mp. 209° C.
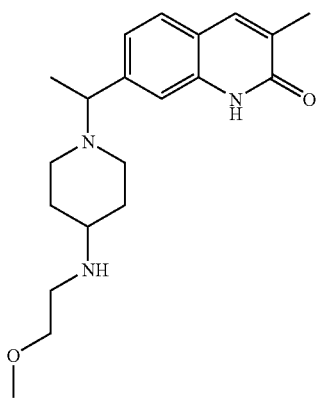 [SMILES: COCCNC1CCN(C(C)c2ccc3cc(C)c(=O)[nH]c3c2)CC1]
Co. No. 55; Ex. [B1]; mp. 114° C.
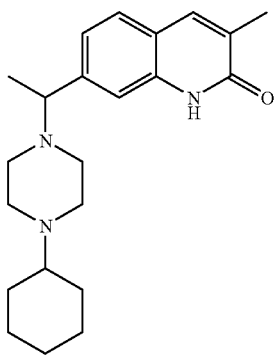 [SMILES: Cc1cc2ccc(C(C)N3CCN(C4CCCCC4)CC3)cc2[nH]c1=O]
Co. No. 54; Ex. [B1]; mp. 188° C.
TABLE F-1-continued
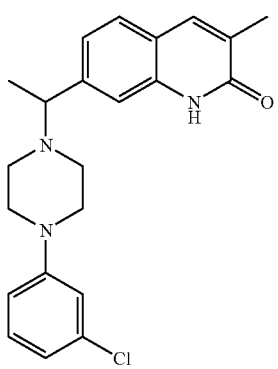 [SMILES: Cc1cc2ccc(C(C)N3CCN(c4cccc(Cl)c4)CC3)cc2[nH]c1=O]
Co. No. 58; Ex. [B3]; mp. 208.4° C.
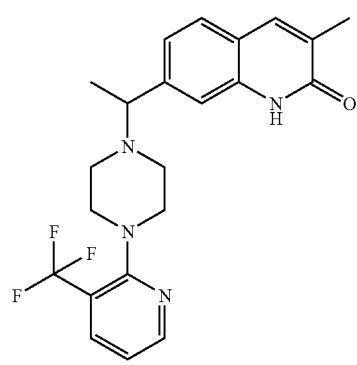 [SMILES: Cc1cc2ccc(C(C)N3CCN(c4ncccc4C(F)(F)F)CC3)cc2[nH]c1=O]
Co. No. 56; Ex. [B1]; mp. 79° C.
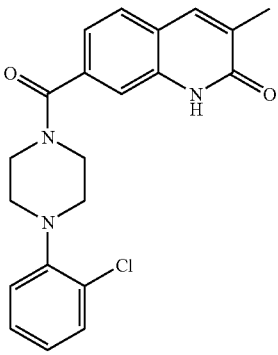 [SMILES: Cc1cc2ccc(C(=O)N3CCN(c4ccccc4Cl)CC3)cc2[nH]c1=O]
0.32 HCl •1.21 H$_2$O; Co. No. 60; Ex. [B3]; mp. 224° C.
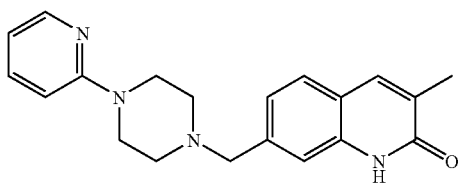 [SMILES: Cc1cc2ccc(CN3CCN(c4ccccn4)CC3)cc2[nH]c1=O]
Co. No. 57; Ex. [B3]; mp. >260° C.

TABLE F-1-continued
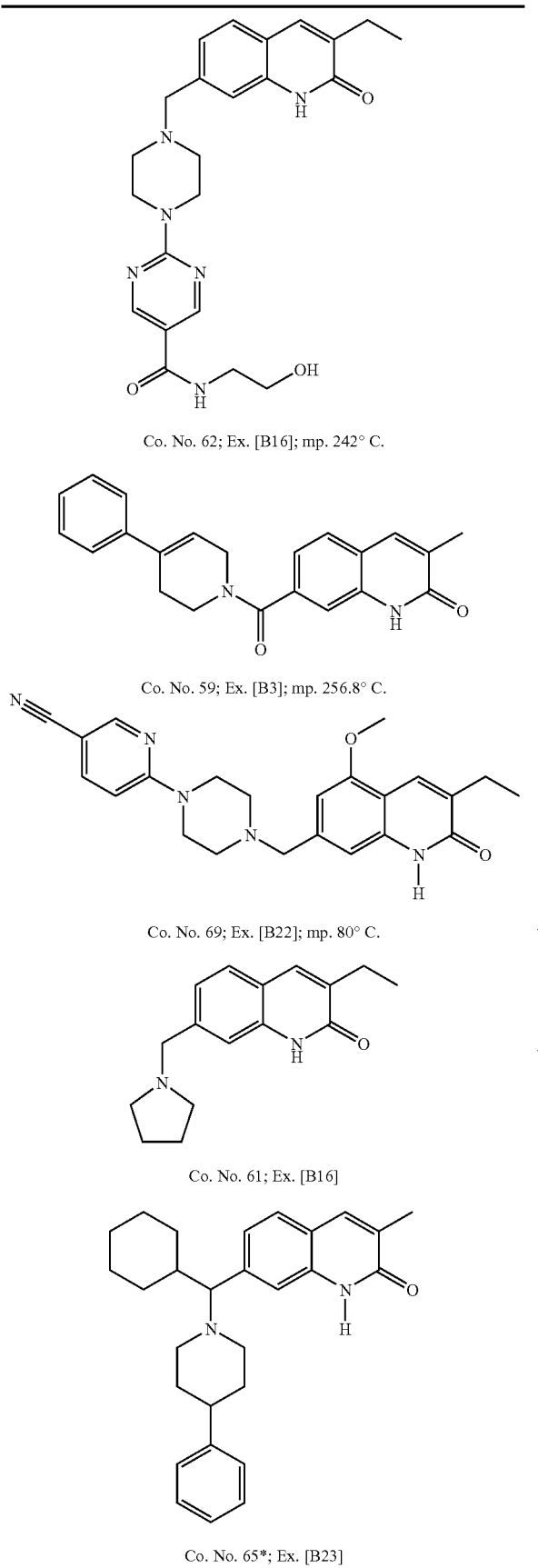
Co. No. 62; Ex. [B16]; mp. 242° C.
Co. No. 59; Ex. [B3]; mp. 256.8° C.
Co. No. 69; Ex. [B22]; mp. 80° C.
Co. No. 61; Ex. [B16]
Co. No. 65*; Ex. [B23]
TABLE F-1-continued
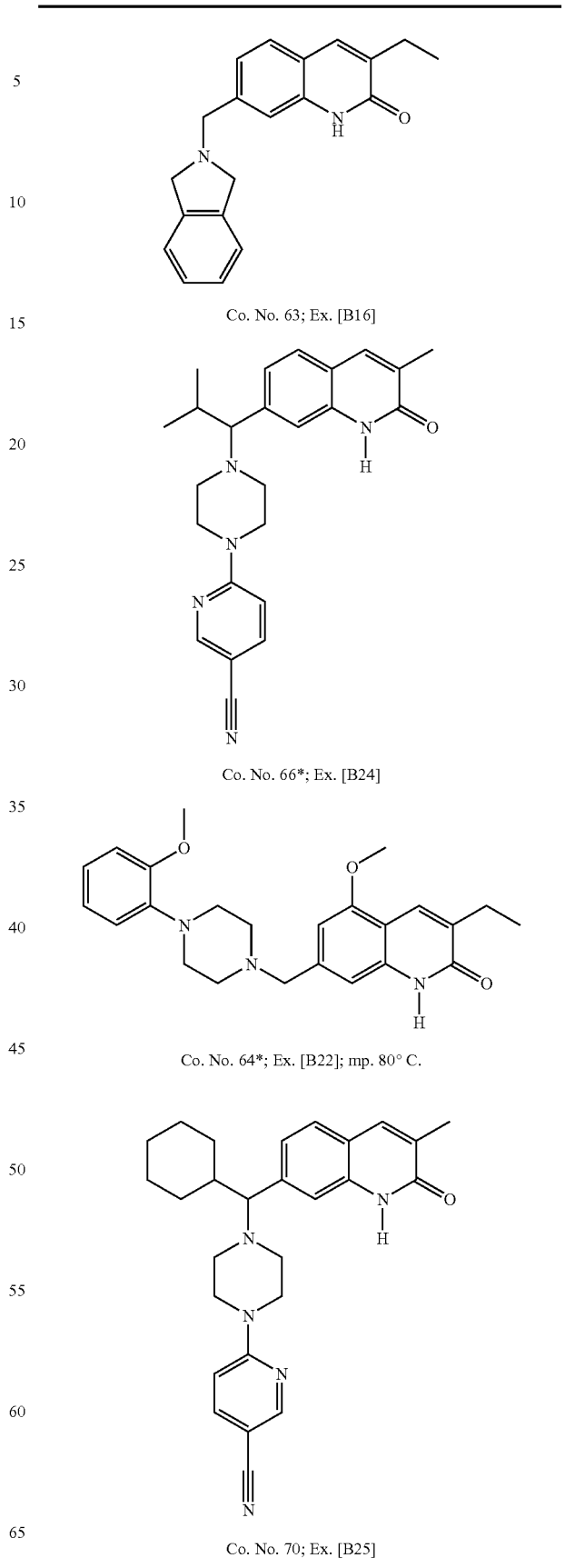
Co. No. 63; Ex. [B16]
Co. No. 66*; Ex. [B24]
Co. No. 64*; Ex. [B22]; mp. 80° C.
Co. No. 70; Ex. [B25]

TABLE F-1-continued
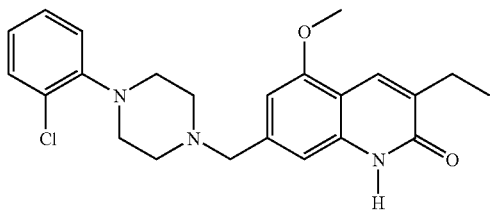
Co. No. 71; Ex. [B22]
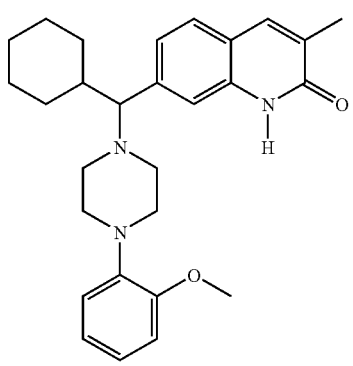
Co. No. 72; Ex. [B25]
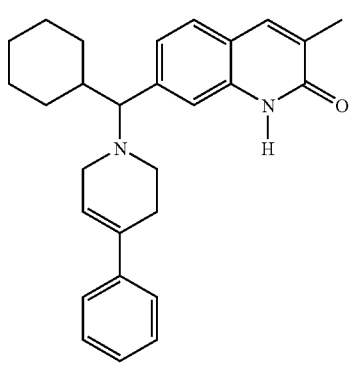
Co. No. 73; Ex. [B23]
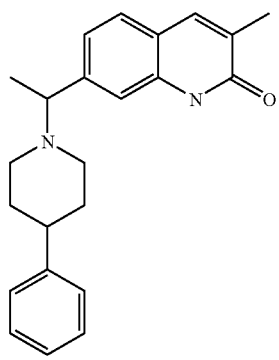 [SMILES: Cc1cc2ccc(C(C)N3CCC(c4ccccc4)CC3)cc2[nH]c1=O]
Co. No. 74; Ex. [B25]
TABLE F-1-continued
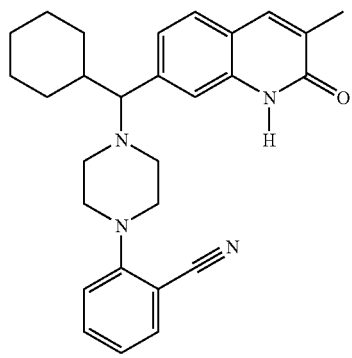 [SMILES: Cc1cc2ccc(C(C3CCCCC3)N3CCN(c4ccccc4C#N)CC3)cc2[nH]c1=O]
Co. No. 67*; Ex. [B25]
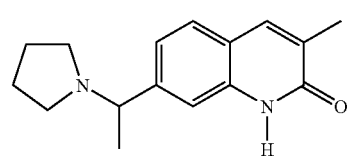 [SMILES: Cc1cc2ccc(C(C)N3CCCC3)cc2[nH]c1=O]
Co. No. 68*; Ex. [B26]; mp. 133° C.
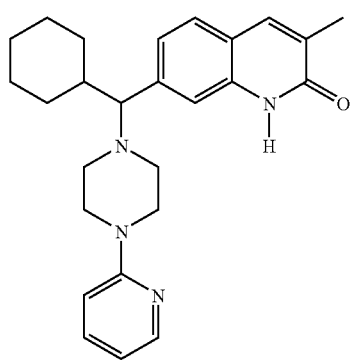
Co. No. 75; Ex. [B25]
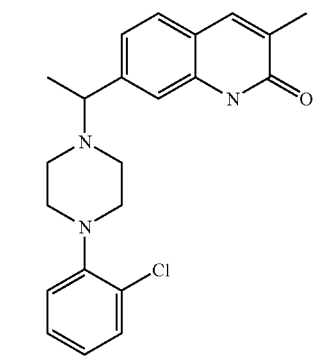 [SMILES: Cc1cc2ccc(C(C)N3CCN(c4ccccc4Cl)CC3)cc2[nH]c1=O]
Co. No. 76; Ex. [B25]

TABLE F-1-continued

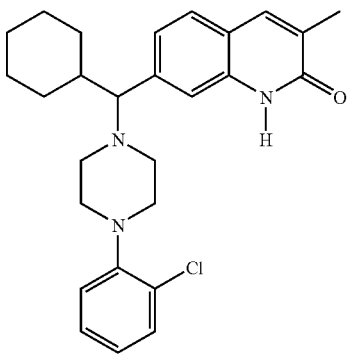 [SMILES: Cc1cc2ccc(C(C3CCCCC3)N3CCN(c4ccccc4Cl)CC3)cc2[nH]c1=O]

Co. No. 77; Ex. [B25]

Analytical Methods

LCMS

The mass of some compounds was recorded with LCMS (liquid chromatography mass spectrometry). The methods used are described below and the results are shown in Table-2 below.

Method 1

The HPLC measurement was performed using an Alliance HT 2795 (Waters) system comprising a quaternary pump with degasser, an autosampler, a diode-array detector (DAD) and a column as specified in the respective methods below, the column is hold at a temperature of 30° C. Flow from the column was split to a MS spectrometer. The MS detector was configured with an electrospray ionization source. The capillary needle voltage was 3 kV and the source temperature was maintained at 100° C. on the LCT (Time of Flight Zspray™ mass spectrometer from Waters). Nitrogen was used as the nebulizer gas. Data acquisition was performed with a Waters-Micromass MassLynx-Openlynx data system. Reversed phase HPLC was carried out on a Xterra-MS C18 column (5 µm, 4.6×150 mm) with a flow rate of 1.0 ml/min. Two mobile phases (mobile phase A: 100% 7 mM ammonium acetate; mobile phase B: 100% acetonitrile; were employed to run a gradient condition from 85% A, 15% B (hold for 3 minutes) to 20% A, 80% B in 5 minutes, hold at 20% A and 80% B for 6 minutes and reequilibrated with initial conditions for 3 minutes. An injection volume of 20 µl was used. Cone voltage was 20 V for positive ionization mode and 20 V for negative ionization mode. Mass spectra were acquired by scanning from 100 to 900 in 0.8 seconds using an interscan delay of 0.08 seconds.

Method 2

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system. Reversed phase UPLC was carried out on a Waters Acquity BEH (bridged ethylsiloxane/silica hybrid) C18 column (1.7 µm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 µl was used. Cone voltage was 20 V for positive and negative ionization mode. Mass spectra were acquired by scanning from 100 to 1000 in 0.2 seconds using an interscan delay of 0.1 seconds.

TABLE 2

LCMS parent peak (MH+) and retention time ($R_t$):

| Compound N° | LC/MS method | (MH+) | $R_t$ (min) |
|---|---|---|---|
| 61 | 1 | 257 | 5.2 |
| 63 | 1 | 305 | 8.7 |
| 18 | 1 | 382 | 9.69 |
| 42 | 1 | 378 | 8.68 |
| 45 | 1 | 382 | 9.74 |
| 43 | 1 | 416 | 10.24 |
| 21 | 1 | 345 | 9.41 |
| 44 | 1 | 376 | 8.2 |
| 19 | 1 | 316 | 4.07 |
| 49 | 1 | 293 | 6.53 |
| 47 | 1 | 294 | 4.33 |
| 46 | 1 | 321 | 6.94 |
| 48 | 1 | 311 | 6.66 |
| 39 | 1 | 362 | 9.37 |
| 40 | 1 | 376 | 9.57 |
| 41 | 1 | 408 | 8.24 |
| 35 | 1 | 349 | 6.04 |
| 36 | 1 | 350 | 7.67 |
| 22 | 1 | 417 | 9.51 |
| 17 | 1 | 374 | 7.06 |
| 37 | 1 | 388 | 6.9 |
| 38 | 1 | 275 | 4.1 |
| 33 | 1 | 380 | 6.36 |
| 12 | 1 | 394 | 6.33 |
| 5 | 1 | 303 | 6.43 |
| 4 | 1 | 303 | 6.5 |
| 56 | 2 | 417 | 3.86 |
| 52 | 2 | 384 | 3.88 |
| 20 | 2 | 373 | 3.58 |
| 23 | 2 | 364 | 3.38 |
| 65 | 2 | 415 | 5.44 |
| 66 | 2 | 402 | 3.84 |
| 67 | 2 | 441 | 4.79 |
| 70 | 2 | 442 | 4.51 |
| 71 | 2 | 412 | 4.29 |
| 72 | 2 | 446 | 5.01 |
| 73 | 2 | 413 | 5.12 |
| 74 | 2 | 347 | 3.68 |
| 75 | 2 | 417 | 4.59 |
| 76 | 2 | 382 | 4.09 |
| 77 | 2 | 449 | 5.36 |

C. Pharmacological Examples

C.1. In Vitro Scintillation Proximity Assay (SPA) for PARP-1 Inhibitory Activity Compounds of the present invention were tested in an in vitro assay based on SPA technology (proprietary to GE healthcare).

In principle, the assay relies upon the well established SPA technology for the detection of poly(ADP-ribosyl)ation of biotinylated target proteins, i.e histones. This ribosylation is induced using nicked DNA activated PARP-1 enzyme and [$^3$H]-nicotinamide adenine dinucleotide ([$^3$H]-NAD$^+$) as ADP-ribosyl donor.

Histones (type II-A, supplier: Sigma) were biotinylated using the biotinylation kit of Amersham and stored aliquoted at −20° C. A stock solution of 100 mg/ml SPA poly(vinyl toluene) (PVT) beads (supplier: Amersham) was made in PBS. A stock solution of 61.6 nM [$^3$H]-NAD$^+$ was made by adding [$^3$H]-NAD$^+$ (0.1 mCi/ml, supplier: Perkin Elmer) to incubation buffer (50 mM Tris/HCl, pH 8; 0.2 mM DTT; 4 mM MgCl$_2$). A solution of 4 mM NAD$^+$ (supplier: Sigma) was made. Human PARP-1 enzyme was obtained from Trevigen. Biotinylated histones and PVT-SPA beads were mixed and pre-incubated for 30 min. at room temperature. PARP-1 enzyme (concentration was lot dependent) was mixed with the nicked DNA and the mixture was pre-incubated for 30 min. at 4° C. Equal parts of this histones/PVT-SPA beads solution and PARP-1 enzyme/DNA solution were mixed and 75 µl of this mixture together with 1 µl of compound in DMSO and 25 µl of [$^3$H]-NAD$^+$ was added per well into a 96-well microtiterplate. The final concentrations in the incubation mixture were 2 µg/ml for the biotinylated histones, 2 mg/ml for the PVT-SPA beads, 0.25 µg/ml for the nicked DNA and between 0.1-0.2 µg/ml for the PARP-1 enzyme. After incubation of the mixture for 20 min. at room temperature, the reaction was terminated by adding 100 µl of 4 mM NAD$^+$ in water (final concentration 2 mM) and plates were mixed. The beads were sedimented by centrifugation (10 min, 800 rpm). and plates transferred to a TopCountNXT™ (Packard) for scintillation counting, values were expressed as counts per minute (cpm). For each experiment, controls (containing PARP-1 enzyme and DMSO without compound), a blank incubation (containing DMSO but no PARP-1 enzyme, no DNA or compound) and samples (containing PARP-1 enzyme, DNA and compound dissolved in DMSO) were run in parallel. All compounds tested were dissolved and eventually further diluted in DMSO. A dose-response curve was made wherein the compounds were tested at concentrations between 10$^{-5}$M and 3×10$^{-9}$M. In each test, the blank value was subtracted from both the control and the sample values. The control sample represented maximal PARP-1 enzyme activity. For each sample, the amount of cpm was expressed as a percentage of the mean cpm value of the controls. When appropriate, IC$_{50}$-values (concentration of the drug, needed to reduce the PARP-1 enzyme activity to 50% of the control) were computed using linear interpolation between the experimental points just above and below the 50% level. Herein the effects of test compounds are expressed as pIC$_{50}$ (the negative log value of the IC$_{50}$-value). As a reference compound, 4-amino-1,8-naphthalimide was included to validate the SPA assay. The tested compounds showed inhibitory activity at various concentrations (see Table-3).

C.2. In Vitro Scintillation Proximity Assay (SPA) for TANK-2 Inhibitory Activity Compounds of the present invention were tested in an in vitro assay based on SPA technology with Ni Flash plates (96 or 384 well).

In principle, the assay relies upon SPA technology for the detection of auto-poly(ADP-ribosyl)ation of TANK-2 protein using [$^3$H]-nicotinamide adenine dinucleotide ([$^3$H]-NAD$^+$) as ADP-ribosyl donor.

A stock solution of 100 nM [$^3$H]-NAD$^+$/NAD (0.1 mCi/ml, supplier: Perkin Elmer) and 0.25 mM NAD (Sigma) was made in assay buffer (60 mM Tris/HCl, pH 7.4; 0.9 mM DTT; 6 mM MgCl$_2$). The TANK-2 enzyme was produced as described in EP1238063. 60 µl of assay buffer, together with 1 µl of compound in DMSO, 20 µl of [$^3$H]-NAD$^+$/NAD and 20 µl of TANK-2 enzyme (final concentration 8 µg/ml) was added per well into a 96-well Ni-coated flash plate (Perkin Elmer). After incubation of the mixture for 120 min. at room temperature, the reaction was terminated by adding 60 µl of stopsolution (42.6 mg NAD in 6 ml H$_2$O). The plates were covered with a plate sealer and placed in a TopCountNX™ (Packard) for scintillation counting. Values were expressed as counts per minute (cpm). For each experiment, controls (containing TANK-2 enzyme and DMSO without compound), a blank incubation (containing DMSO but no TANK-2 enzyme or compound) and samples (containing TANK-2 enzyme and compound dissolved in DMSO) were run in parallel. All compounds tested were dissolved and eventually further diluted in DMSO. In first instance, compounds were tested at a concentration of 10$^{-5}$ M. When the compounds showed activity at 10$^{-5}$M, a dose-response curve was made wherein the compounds were tested at concentrations between 10$^{-5}$M and 3×10$^{-8}$M. In each test, the blank value was subtracted from both the control and the sample values. The control sample represented maximal TANK-2 enzyme activity. For each sample, the amount of cpm was expressed as a percentage of the mean cpm value of the controls. When appropriate, IC$_{50}$-values (concentration of the drug, needed to reduce the TANK-2 enzyme activity to 50% of the control) were computed using linear interpolation between the experimental points just above and below the 50% level. Herein the effects of test compounds are expressed as pIC$_{50}$ (the negative log value of the IC$_{50}$-value). As reference compounds, 3-aminobenzamide and 4-amino-1,8-naphtalimide were included to validate the SPA assay. Herein the assay was described using 96-well plates. In the assay using 384-well plates the same final concentrations were used and volumes were adapted. If 96-well plate results were available these results were incorporated in Table-3, otherwise the results from the 384-well plate assay were shown.

TABLE 3

| Compound No. | in vitro SPA assay PARP-1 pIC50 | in vitro SPA assay TANK-2 pIC50 |
| --- | --- | --- |
| 18 | 9.247 | 5.714 |
| 2 | 9.218 | 6.163 |
| 17 | 9.063 | 7.116 |
| 42 | 9.049 | 5.886 |
| 6 | 9.028 | 5.722 |
| 21 | 8.986 | 6.006 |
| 20 | 8.967 | 6.027 |
| 35 | 8.942 | 6.4 |
| 22 | 8.916 | 6.434 |
| 3 | 8.908 | 5.264 |
| 52 | 8.848 | 5.617 |
| 57 | 8.831 | 5.375 |
| 51 | 8.828 | 5.892 |
| 50 | 8.824 | 5.553 |
| 7 | 8.818 | <5 |
| 36 | 8.594 | 6.654 |
| 43 | 8.588 | 5.765 |
| 13 | 8.405 | 6.571 |
| 19 | 8.337 | 5.231 |
| 61 | 8.271 | 5.375 |
| 37 | 8.246 | 6.634 |
| 44 | 8.161 | 5.66 |
| 16 | 8.131 | 7.441 |
| 62 | 8.048 | 7.481 |
| 46 | 8.023 | 5.269 |
| 38 | 7.924 | 6.062 |
| 1 | 7.873 | 5.841 |
| 30 | 7.845 | 6.725 |
| 45 | 7.788 | 5.768 |
| 39 | 7.768 | 6.131 |
| 29 | 7.699 | 6.373 |
| 48 | 7.612 | 6.596 |
| 40 | 7.591 | 6.188 |
| 41 | 7.466 | 6.301 |
| 28 | 7.458 | 6.187 |
| 63 | 7.407 | 6.342 |

TABLE 3-continued

| Compound No. | in vitro SPA assay PARP-1 pIC50 | in vitro SPA assay TANK-2 pIC50 |
|---|---|---|
| 49 | 7.368 | 6.809 |
| 53 | 7.303 | <5 |
| 11 | 7.29 | 7.442 |
| 54 | 7.212 | <5 |
| 27 | 7.187 | 5.402 |
| 14 | 7.154 | 6.369 |
| 12 | 7.113 | 7.184 |
| 15 | 7.111 | 5.667 |
| 24 | 7.095 | 6 |
| 5 | 7.082 | 5.841 |
| 33 | 7.072 | 6.108 |
| 32 | 7.048 | 7.035 |
| 55 | 7.036 | <5 |
| 34 | 7.024 | 6.408 |
| 58 | 7.018 | 5.634 |
| 10 | 6.966 | 6.343 |
| 9 | 6.962 | 5.509 |
| 60 | 6.937 | <5 |
| 47 | 6.905 | 6.841 |
| 59 | 6.889 | 6.087 |
| 25 | 6.866 | 5.957 |
| 8 | 6.77 | 7.199 |
| 56 | 6.648 | 5.716 |
| 26 | 6.626 | 5.703 |
| 31 | 6.395 | 5.506 |
| 23 | 9.6 | <5 |
| 4 | 6.697 | 6.647 |
| 64 | 8.52 | 5.35 |
| 65 | 5.39 | <5 |
| 66 | 6.71 | 5.91 |
| 67 | 6.15 | <5 |
| 68 | 9.12 | 5.67 |
| 69 | — | 7.24 |
| 70 | 6.56 | 5.72 |
| 71 | 8.37 | 5.75 |
| 72 | 5 | 6.03 |
| 73 | 5.89 | 6.19 |
| 74 | 8.19 | 5.73 |
| 75 | 6.51 | <5 |
| 76 | 9.19 | 5.81 |
| 77 | 6.68 | 5.95 |

The invention claimed is:

1. A compound of formula (I):

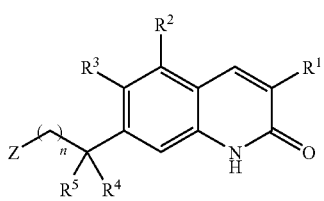

the N-oxide form, the pharmaceutically acceptable addition salt, the quaternary ammonium salt and the stereochemically isomeric form thereof, wherein n is 0, 1 or 2;

$R^1$ is $C_{1-3}$alkyl;

$R^2$ and $R^3$ are each independently selected from hydrogen, halogen, $C_{1-6}$alkyl, cyano, hydroxy, $C_{1-6}$alkyloxy, $C_{3-6}$cycloalkyloxy, cyano$C_{1-4}$alkyl, hydroxy$C_{1-4}$alkyloxy, $C_{1-4}$alkyloxy$C_{1-4}$alkyloxy, amino$C_{1-4}$alkyloxy, $C_{1-4}$alkylamino$C_{1-4}$alkyloxy, di($C_{1-4}$alkyl)amino$C_{1-4}$alkyloxy, aminocarbonyl or $C_{2-4}$alkynyl;

$R^4$ and $R^5$ are each independently selected from hydrogen, $C_{1-6}$alkyl, $C_{3-6}$cycloalkyl, hydroxy, $C_{1-6}$alkyloxy, $C_{1-6}$alkyloxymethyl or hydroxy$C_{1-6}$alkyl, or $R^4$ and $R^5$ together form =O;

Z is a group of formula —$NR^6R^7$ wherein $R^6$ is hydrogen or $C_{1-4}$alkyl;

$R^7$ is $C_{1-4}$alkyloxy$C_{1-4}$alkyl or a group of formula

—$(CH_2)_t$-$L^1$ (a-1)

wherein t is 0, 1, 2 or 3 and $L^1$ is phenyl or phenyl substituted with one or two substituents independently selected from hydrogen, halo, cyano, $C_{1-4}$alkyl, $C_{1-4}$alkyloxy, hydroxycarbonyl, $C_{1-4}$alkyloxycarbonyl or aminocarbonyl;

or $L^1$ is a heterocyclic ring system selected from:

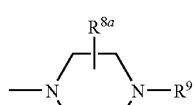 (b-1)

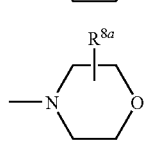 (b-2)

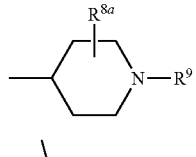 (b-3)

 (b-4)

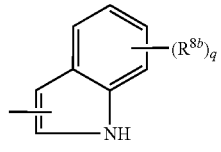 (b-5)

wherein $R^{8a}$ is selected from hydrogen, $C_{1-4}$alkyl, hydroxy$C_{1-4}$alkyl or aminocarbonyl;

q is 0, 1 or 2; and each $R^{8b}$ is independently selected from hydrogen, halogen, cyano, $C_{1-4}$alkyl, hydroxy$C_{1-4}$alkyl, $C_{1-4}$alkyloxy or aminocarbonyl; and $R^9$ is hydrogen, $C_{1-4}$alkyl, phenyl or a heterocyclic ring system selected from:

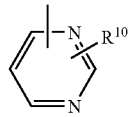 (c-1)

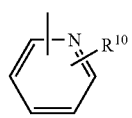 (c-2)

wherein $R^{10}$ is selected from hydrogen, halogen, cyano, $C_{1-4}$alkyl or $C_{1-4}$alkyloxy;

or Z is a heterocyclic ring system selected from:

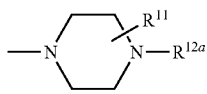 (d-1)

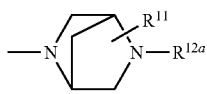 (d-2)

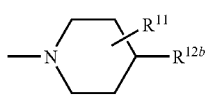 (d-3)

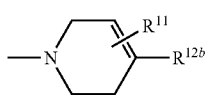 (d-4)

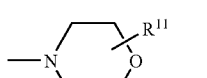 (d-5)

 (d-6)

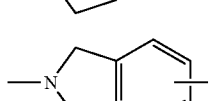 (d-7)

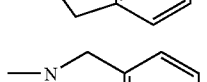 (d-8)

wherein $R^{11}$ is hydrogen, $C_{1-4}$alkyl, hydroxyl, cyano, hydroxy$C_{1-4}$alkyl or aminocarbonyl; and
$R^{12a}$ is hydrogen or $C_{1-4}$alkyloxy$C_{1-4}$alkyl;

or —X-$L^2$ (e-1)

$R^{12b}$ is hydrogen, $C_{1-4}$alkyloxy$C_{1-4}$alkyl or $C_{1-6}$alkyloxy$C_{1-6}$alkylamino;

or —X-$L^2$ (e-1)

X is —$(CH_2)_p$— in which p is 0, 1, 2 or 3;
$L^2$ is $C_{3-6}$cycloalkyl, phenyl or phenyl substituted with one or two substituents independently selected from halo, $C_{1-4}$alkyl, $C_{1-4}$alkyloxy, amino, cyano or trifluoromethyl; or $L^2$ is a heterocyclic ring system selected from:

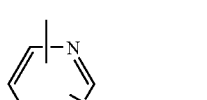 (f-1)

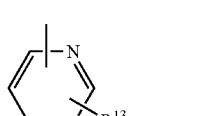 (f-2)

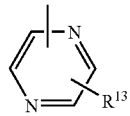 (f-3)

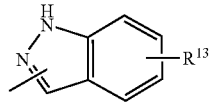 (f-4)

wherein $R^{13}$ is selected from hydrogen, halo, $C_{1-4}$alkyl, $C_{1-4}$alkyloxy, $C_{2-4}$alkynyl, aminocarbonyl, cyano, trifluoromethyl, amino, hydroxy$C_{1-4}$alkylaminocarbonyl, hydroxycarbonyl or $C_{1-4}$alkyloxycarbonyl.

2. A compound according to claim 1 wherein:
n is 0, 1 or 2;
$R^1$ is $C_{1-3}$alkyl;
$R^2$ and $R^3$ are each independently selected from hydrogen, halogen, $C_{1-6}$alkyl, cyano, hydroxy or $C_{1-6}$alkyloxy;
$R^4$ and $R^5$ are each independently selected from hydrogen, $C_{1-6}$alkyl, $C_{3-6}$cycloalkyl, hydroxy, $C_{1-6}$alkyloxy, $C_{1-6}$alkyloxymethyl or hydroxy$C_{1-6}$alkyl, or $R^4$ and $R^5$ together form =O;
Z is a group of formula —$NR^6R^7$ wherein
$R^6$ is hydrogen or $C_{1-4}$alkyl;
$R^7$ is $C_{1-4}$alkyloxy$C_{1-4}$alkyl or a group of formula —$(CH_2)_t$-$L^1$ (a-1)

wherein t is 0, 1, 2 or 3 and $L^1$ is phenyl or phenyl substituted with one or two substituents independently selected from hydrogen, halo, cyano, $C_{1-4}$alkyl or $C_{1-4}$alkyloxy;
or $L^1$ is a heterocyclic ring system selected from:

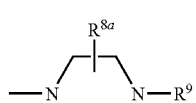 (b-1)

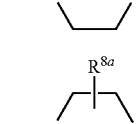 (b-2)

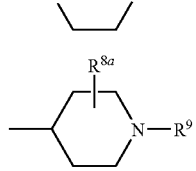 (b-3)

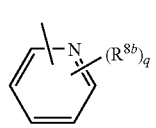 (b-4)

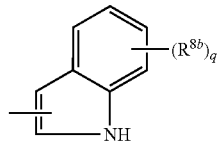 (b-5)

wherein $R^{8a}$ is selected from hydrogen, $C_{1-4}$alkyl, hydroxy$C_{1-4}$alkyl or aminocarbonyl;

q is 0 or 1; and each $R^{8b}$ is independently selected from hydrogen, halogen, cyano, hydroxy$C_{1-4}$alkyl, $C_{1-4}$alkyloxy or aminocarbonyl; and $R^9$ is hydrogen, $C_{1-4}$alkyl, phenyl or a heterocyclic ring system selected from:

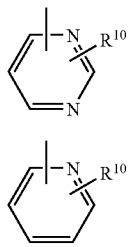

(c-1)

(c-2)

wherein $R^{10}$ is selected from hydrogen, halogen, cyano, $C_{1-4}$alkyl or $C_{1-4}$alkyloxy;

or Z is a heterocyclic ring system selected from:

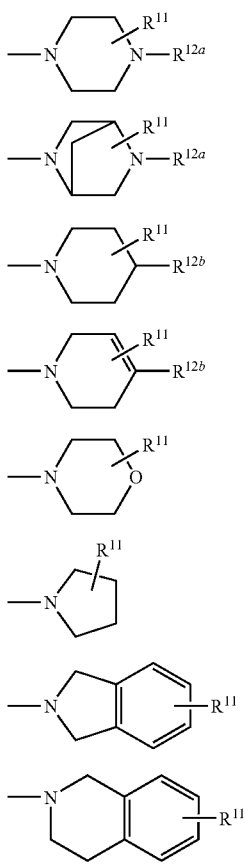

(d-1)

(d-2)

(d-3)

(d-4)

(d-5)

(d-6)

(d-7)

(d-8)

wherein $R^{11}$ is hydrogen or $C_{1-4}$alkyl; and
$R^{12a}$ is hydrogen or $C_{1-4}$alkyloxy$C_{1-4}$alkyl;

or —X-$L^2$ (e-1)

$R^{12b}$ is hydrogen, $C_{1-4}$alkyloxy$C_{1-4}$alkyl or $C_{1-6}$alkyloxy$C_{1-6}$alkylamino;

or —X-$L^2$ (e-1)

X is —(CH$_2$)$_p$— in which p is 0, 1, 2 or 3;

$L^2$ is phenyl or phenyl substituted with one or two substituents independently selected from halo, $C_{1-4}$alkyl, $C_{1-4}$alkyloxy, amino, cyano or trifluoromethyl; or $L^2$ is a heterocyclic ring system selected from:

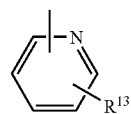

(f-1)

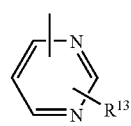

(f-2)

(f-3)

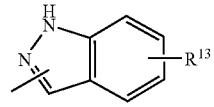

(f-4)

wherein $R^{13}$ is selected from hydrogen, halo, $C_{1-4}$alkyl, $C_{1-4}$alkyloxy, $C_{2-4}$alkynyl, aminocarbonyl, cyano, trifluoromethyl, amino, hydroxy$C_{1-4}$alkylaminocarbonyl, hydroxycarbonyl or $C_{1-4}$alkyloxycarbonyl.

3. A compound according to claim 1 wherein:
n is 0, 1 or 2;
$R^1$ is methyl or ethyl;
$R^2$ is selected from hydrogen, methyl, ethyl, cyano or methyloxy;
$R^3$ is hydrogen;
$R^4$ and $R^5$ are each independently selected from hydrogen, $C_{1-6}$alkyl, $C_{3-6}$cycloalkyl, hydroxy or hydroxy$C_{1-6}$alkyl, or $R^4$ and $R^5$ together form =O;
Z is a group of formula —NR$^6$R$^7$ wherein
$R^6$ is hydrogen or $C_{1-4}$alkyl;
$R^7$ is $C_{1-4}$alkyloxy$C_{1-4}$alkyl or a group of formula:

—(CH$_2$)$_t$-$L^1$ (a-1)

wherein t is 0, 1, 2 or 3 and $L^1$ is phenyl or phenyl substituted with one or two halo substituents;
or $L^1$ is a heterocyclic ring system selected from:

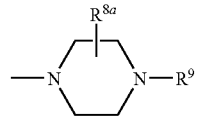

(b-1)

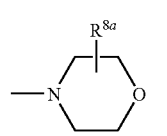

(b-2)

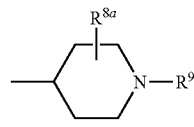

(b-3)

-continued

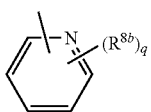 (b-4)

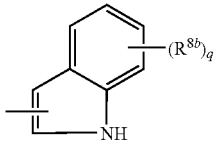 (b-5)

wherein R$^{8a}$ is hydrogen; q is 0; and
R$^9$ is hydrogen or the heterocyclic ring system (c-1):

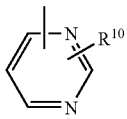 (c-1)

wherein R$^{10}$ is hydrogen;
or Z is a heterocyclic ring system selected from:

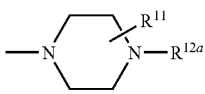 (d-1)

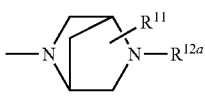 (d-2)

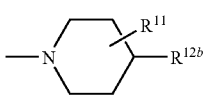 (d-3)

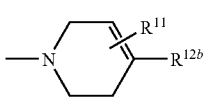 (d-4)

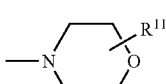 (d-5)

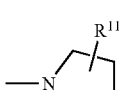 (d-6)

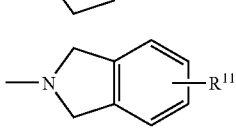 (d-7)

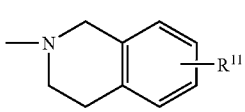 (d-8)

wherein R$^{11}$ is hydrogen; and
R$^{12a}$ is hydrogen or C$_{1-4}$alkyloxyC$_{1-4}$alkyl;

or —X-L$^2$ (e-1)

R$^{12b}$ is hydrogen or C$_{1-6}$alkyloxyC$_{1-6}$alkylamino;
or —X-L$^2$ (e-1)

X is —(CH$_2$)$_p$— in which p is 0, 1 or 2;
L$^2$ is phenyl or phenyl substituted with one or two substituents independently selected from halo, C$_{1-4}$alkyl, C$_{1-4}$alkyloxy or cyano; or L$^2$ is a heterocyclic ring system selected from:

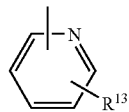 (f-1)

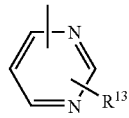 (f-2)

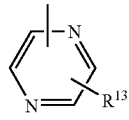 (f-3)

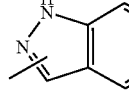 (f-4)

wherein R$^{13}$ is selected from hydrogen, chloro, aminocarbonyl, cyano, C$_{1-4}$alkyloxy, trifluoromethyl, hydroxyC$_{1-4}$alkylaminocarbonyl, hydroxycarbonyl or C$_{1-4}$alkyloxycarbonyl.

4. A compound according to claim 1 wherein:
n is 0;
R$^1$ is methyl or ethyl;
R$^2$ is hydrogen or methyloxy;
R$^3$ is hydrogen;
R$^4$ and R$^5$ are each hydrogen;
Z is a group of formula —NR$^6$R$^7$ wherein
R$^6$ is hydrogen or C$_{1-4}$alkyl;
R$^7$ is C$_{1-4}$alkyloxyC$_{1-4}$alkyl or a group of formula —(CH$_2$)$_t$-L$^1$ (a-1)

wherein t is 0, 1, 2 or 3 and L$^1$ is phenyl or phenyl substituted with one or two halo substituents; or L$^1$ is a heterocyclic ring system selected from:

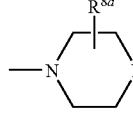 (b-1)

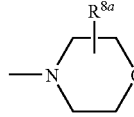 (b-2)

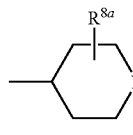 (b-3)

-continued (b-4)
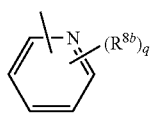

(b-5)
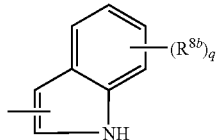

wherein $R^{8a}$ is hydrogen; q is 0; and
$R^9$ is hydrogen or the heterocyclic ring system (c-1):

(c-1)
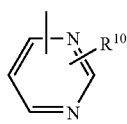

wherein $R^{16}$ is hydrogen.

5. A compound according to claim 1 wherein:
n is 0, 1 or 2;
$R^1$ is $C_{1-3}$alkyl;
$R^2$ is hydrogen or methyloxy;
$R^3$ is hydrogen;
$R^4$ and $R^5$ are each independently selected from hydrogen, $C_{1-6}$alkyl, hydroxy, or hydroxy$C_{1-6}$alkyl, or $R^4$ and $R^5$ together form =O;
Z is a heterocyclic ring system selected from:

(d-1)
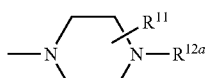

(d-2)
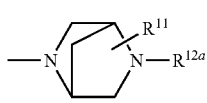

(d-3)
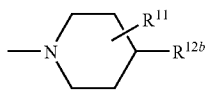

(d-4)
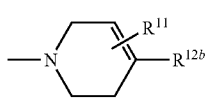

(d-5)
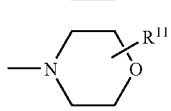

(d-6)
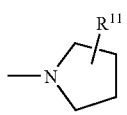

(d-7)
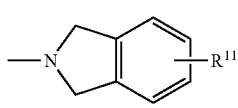

(d-8)
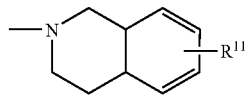

wherein $R^{11}$ is hydrogen;
$R^{12a}$ is hydrogen or $C_{1-4}$alkyloxy$C_{1-4}$alkyl;

or —X-$L^2$ (e-1)

X is —$(CH_2)_p$— in which p is 0 or 2;
$L^2$ is phenyl or phenyl substituted with one or two substituents independently selected from halo, $C_{1-4}$alkyl, $C_{1-4}$alkyloxy or cyano; or $L^2$ is a heterocyclic ring system selected from:

(f-1)
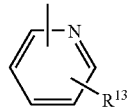

(f-2)
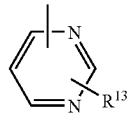

(f-3)
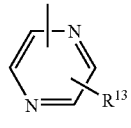

(f-4)
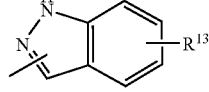

wherein $R^{13}$ is selected from hydrogen, aminocarbonyl, cyano, $C_{1-4}$alkyloxy, trifluoromethyl, hydroxy $C_{1-4}$alkylaminocarbonyl, hydroxycarbonyl or $C_{1-4}$alkyloxycarbonyl;
$R^{12b}$ is hydrogen or $C_{1-6}$alkyloxy$C_{1-6}$alkylamino;

or —X-$L^2$ (e-1)

X is —$(CH_2)_p$— in which p is 0 or 1;
$L^2$ is phenyl or phenyl substituted with one or two halo substituents; or $L^2$ is a heterocyclic ring system selected from:

(f-1)
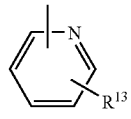

(f-2)
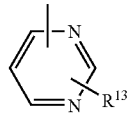

(f-3)

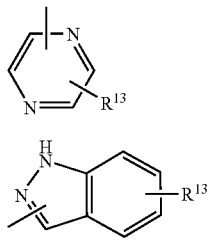

(f-4)

wherein R$^{13}$ is selected from hydrogen, chloro, aminocarbonyl, cyano, methyloxy, trifluoromethyl, hydroxyC$_{1-4}$alkylaminocarbonyl, hydroxycarbonyl or C$_{1-4}$alkyloxycarbonyl.

6. A compound according to claim 1 selected from Compounds 17, 18, 20, 21, 22 and 23 herein and the N-oxide forms, the pharmaceutically acceptable addition salts, the quaternary ammonium salts and the stereochemically isomeric forms thereof.

7. A pharmaceutical composition comprising a therapeutically effective amount of at least one compound according to claim 1-together with a pharmaceutically acceptable carrier.

8. A method for inhibiting PARP comprising administering an effective amount of a compound according to claim 1 to the subject.

9. A method for inhibiting PARP comprising administering an effective amount of a compound according to claim 2 to the subject.

10. A method for inhibiting PARP comprising administering an effective amount of a compound according to claim 3 to the subject.

11. A method for inhibiting PARP comprising administering an effective amount of a compound according to claim 4 to the subject.

12. A method for inhibiting PARP comprising administering an effective amount of a compound according to claim 5 to the subject.

13. A method for inhibiting PARP comprising administering an effective amount of a compound according to claim 6 to the subject.

14. The method for increasing the sensitivity of cells to chemotherapy or ionizing radiation in a subject in need of such therapy, said method comprising administering an effective amount of a compound according to claim 1 to the subject.

* * * * *

UNITED STATES PATENT AND TRADEMARK OFFICE
CERTIFICATE OF CORRECTION

PATENT NO. : 8,404,713 B2  Page 1 of 1
APPLICATION NO. : 12/681790
DATED : March 26, 2013
INVENTOR(S) : Angibaud et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 355 days.

Signed and Sealed this
First Day of September, 2015

Michelle K. Lee
*Director of the United States Patent and Trademark Office*